US009308087B2

(12) United States Patent
Lane et al.

(10) Patent No.: US 9,308,087 B2
(45) Date of Patent: Apr. 12, 2016

(54) SEQUENTIALLY DEPLOYED TRANSCATHETER MITRAL VALVE PROSTHESIS

(71) Applicants: Randy Matthew Lane, Langley (CA); Colin A. Nyuli, Vancoucer (CA); Alexei J. Marko, Vancouver (CA); Krista L. Neale, Vancouver (CA)

(72) Inventors: Randy Matthew Lane, Langley (CA); Colin A. Nyuli, Vancouver (CA); Alexei J. Marko, Vancouver (CA); Krista L. Neale, Vancouver (CA)

(73) Assignee: NEOVASC TIARA INC. (CA)

( * ) Notice: Subject to any disclaimer, the term of this patent is extended or adjusted under 35 U.S.C. 154(b) by 637 days.

(21) Appl. No.: 13/679,920

(22) Filed: Nov. 16, 2012

(65) Prior Publication Data
US 2013/0211508 A1    Aug. 15, 2013

Related U.S. Application Data

(60) Provisional application No. 61/563,156, filed on Nov. 23, 2011.

(51) Int. Cl.
*A61F 2/24*    (2006.01)
(52) U.S. Cl.
CPC ............... *A61F 2/243* (2013.01); *A61F 2/2403* (2013.01); *A61F 2/2412* (2013.01);
(Continued)

(58) Field of Classification Search
CPC .......... A61F 2/24; A61F 2/2418; A61F 2/243
USPC ....................................... 623/2.14, 2.17–2.19
See application file for complete search history.

(56) References Cited

U.S. PATENT DOCUMENTS 3,548,417 A * 12/1970 Kischer et al. ............... 623/2.17
3,739,402 A    6/1973 Kahn et al.
(Continued)

FOREIGN PATENT DOCUMENTS

DE    102006052564 B3    12/2007
GB        1264471 A     2/1972
(Continued)

OTHER PUBLICATIONS

Bavaria. CardiAQ Valve Technologies (CVT) discloses successful results of acute in vivo study of its novel transcatheter mitral valve implantation (TMVI) system. Enhanced Online News. Sep. 28, 2009. Accessed: Mar. 8, 2012. http://eon.businesswire.com/news/eon/20090928005120/en/CardiAQ-Valve-Technologies/Heart/heart-failure.
(Continued)

*Primary Examiner* — Kathleen Holwerda
(74) *Attorney, Agent, or Firm* — Wilson Sonsini Goodrich & Rosati

(57) ABSTRACT

A sequentially deployed prosthetic cardiac valve includes a self-expanding frame having an atrial skirt, a ventricular skirt, and an annular region disposed therebetween. A first anterior tab is disposed on an anterior portion of the frame. A posterior tab is on a posterior portion of the self-expanding frame. The frame may be designed so that any portion may expand sequentially in any desired order. For example, a portion of the first anterior tab and a portion of the posterior tab may partially self-expand first. Next, the first anterior tab may fully self-expand before the posterior tab fully self-expands. The posterior tab may fully self-expand next followed by the ventricular skirt, or the ventricular skirt may self-expand next followed by full expansion of the posterior tab.

32 Claims, 42 Drawing Sheets

(52) U.S. Cl.
CPC ............ *A61F 2/2418* (2013.01); *A61F 2/2427* (2013.01); *A61F 2220/005* (2013.01); *A61F 2220/0016* (2013.01); *A61F 2220/0058* (2013.01); *A61F 2220/0075* (2013.01); *A61F 2230/005* (2013.01); *A61F 2230/0054* (2013.01)

(56) References Cited

U.S. PATENT DOCUMENTS

| | | |
|---|---|---|
| 4,079,468 A | 3/1978 | Liotta et al. |
| 4,204,283 A | 5/1980 | Bellhouse et al. |
| 4,339,831 A | 7/1982 | Johnson |
| 4,340,977 A | 7/1982 | Brownlee et al. |
| 4,470,157 A | 9/1984 | Love |
| 4,490,859 A | 1/1985 | Black et al. |
| 4,865,600 A | 9/1989 | Carpentier et al. |
| 5,415,667 A | 5/1995 | Frater |
| 5,669,919 A | 9/1997 | Sanders et al. |
| 5,868,782 A | 2/1999 | Frantzen |
| 5,928,281 A | 7/1999 | Huynh et al. |
| 6,042,606 A | 3/2000 | Frantzen |
| 6,074,417 A | 6/2000 | Peredo |
| 6,086,612 A | 7/2000 | Jansen |
| 6,113,631 A | 9/2000 | Jansen |
| 6,312,465 B1 | 11/2001 | Griffin et al. |
| 6,358,277 B1 | 3/2002 | Duran |
| 6,458,153 B1 | 10/2002 | Bailey et al. |
| 6,610,088 B1 | 8/2003 | Gabbay |
| 6,629,534 B1 | 10/2003 | St. Goar et al. |
| 6,652,578 B2 | 11/2003 | Bailey et al. |
| 6,764,505 B1 | 7/2004 | Hossainy et al. |
| 6,875,231 B2 | 4/2005 | Anduiza et al. |
| 6,929,660 B1 | 8/2005 | Ainsworth et al. |
| 7,018,406 B2 | 3/2006 | Seguin et al. |
| 7,186,265 B2 | 3/2007 | Sharkawy et al. |
| 7,329,278 B2 | 2/2008 | Seguin et al. |
| 7,338,520 B2 | 3/2008 | Bailey et al. |
| 7,435,257 B2 | 10/2008 | Lashinski et al. |
| 7,442,204 B2 | 10/2008 | Schwammenthal et al. |
| 7,455,689 B2 | 11/2008 | Johnson |
| 7,524,330 B2 | 4/2009 | Berreklouw |
| 7,637,945 B2 | 12/2009 | Solem et al. |
| 7,637,946 B2 | 12/2009 | Solem et al. |
| 7,799,072 B2 | 9/2010 | Greenberg |
| 7,914,569 B2 | 3/2011 | Nguyen et al. |
| 7,914,575 B2 | 3/2011 | Guyenot et al. |
| 7,972,377 B2 | 7/2011 | Lane |
| 8,092,520 B2 | 1/2012 | Quadri |
| 8,226,710 B2 | 7/2012 | Nguyen et al. |
| 8,337,541 B2 | 12/2012 | Quadri et al. |
| 8,398,708 B2 | 3/2013 | Meiri et al. |
| 8,403,983 B2 | 3/2013 | Quadri et al. |
| 8,408,214 B2 | 4/2013 | Spenser |
| 8,414,644 B2 | 4/2013 | Quadri et al. |
| 8,449,599 B2 | 5/2013 | Chau et al. |
| 8,652,203 B2 | 2/2014 | Quadri et al. |
| 8,795,356 B2 | 8/2014 | Quadri et al. |
| 2001/0007956 A1 | 7/2001 | Letac et al. |
| 2002/0032481 A1 | 3/2002 | Gabbay |
| 2003/0105517 A1 | 6/2003 | White et al. |
| 2003/0114913 A1 | 6/2003 | Spenser et al. |
| 2003/0176914 A1 | 9/2003 | Rabkin et al. |
| 2004/0093060 A1 | 5/2004 | Seguin et al. |
| 2004/0102842 A1 | 5/2004 | Jansen |
| 2004/0117009 A1 | 6/2004 | Cali et al. |
| 2004/0181238 A1 | 9/2004 | Zarbatany et al. |
| 2004/0193261 A1 | 9/2004 | Berreklouw |
| 2004/0215325 A1 | 10/2004 | Penn et al. |
| 2004/0225353 A1 | 11/2004 | McGuckin et al. |
| 2004/0236411 A1 | 11/2004 | Sarac et al. |
| 2004/0243230 A1 | 12/2004 | Navia et al. |
| 2004/0260390 A1* | 12/2004 | Sarac et al. ............... 623/1.24 |
| 2005/0075727 A1 | 4/2005 | Wheatley |
| 2005/0107872 A1 | 5/2005 | Mensah et al. |
| 2005/0137686 A1 | 6/2005 | Salahieh et al. |
| 2005/0137690 A1 | 6/2005 | Salahieh et al. |
| 2005/0159811 A1 | 7/2005 | Lane |
| 2005/0182486 A1 | 8/2005 | Gabbay |
| 2005/0234546 A1* | 10/2005 | Nugent et al. ............... 623/2.11 |
| 2006/0020247 A1 | 1/2006 | Kagan et al. |
| 2006/0020327 A1 | 1/2006 | Lashinski et al. |
| 2006/0020334 A1 | 1/2006 | Lashinski et al. |
| 2006/0058872 A1 | 3/2006 | Salahieh et al. |
| 2006/0095115 A1 | 5/2006 | Bladillah et al. |
| 2006/0149360 A1 | 7/2006 | Schwammenthal et al. |
| 2006/0195183 A1 | 8/2006 | Navia et al. |
| 2006/0241745 A1 | 10/2006 | Solem |
| 2006/0259135 A1* | 11/2006 | Navia et al. ............... 623/2.11 |
| 2006/0259136 A1 | 11/2006 | Nguyen et al. |
| 2006/0293698 A1 | 12/2006 | Douk |
| 2006/0293745 A1 | 12/2006 | Carpentier et al. |
| 2007/0016286 A1 | 1/2007 | Herrmann et al. |
| 2007/0043435 A1 | 2/2007 | Seguin et al. |
| 2007/0050020 A1 | 3/2007 | Spence |
| 2007/0050021 A1 | 3/2007 | Johnson |
| 2007/0142906 A1 | 6/2007 | Figulla et al. |
| 2007/0255394 A1 | 11/2007 | Ryan |
| 2007/0293940 A1 | 12/2007 | Schaeffer et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0082164 A1 | 4/2008 | Friedman |
| 2008/0097571 A1 | 4/2008 | Denison et al. |
| 2008/0147179 A1 | 6/2008 | Cai et al. |
| 2008/0177381 A1 | 7/2008 | Navia et al. |
| 2008/0183273 A1 | 7/2008 | Mesana et al. |
| 2008/0221672 A1 | 9/2008 | Lamphere et al. |
| 2008/0228201 A1 | 9/2008 | Zarbatany et al. |
| 2008/0228254 A1 | 9/2008 | Ryan |
| 2008/0243245 A1 | 10/2008 | Thambar et al. |
| 2008/0255660 A1 | 10/2008 | Guyenot et al. |
| 2009/0005863 A1 | 1/2009 | Goetz et al. |
| 2009/0012602 A1 | 1/2009 | Quadri |
| 2009/0062908 A1 | 3/2009 | Bonhoeffer et al. |
| 2009/0082844 A1 | 3/2009 | Zacharias et al. |
| 2009/0138079 A1 | 5/2009 | Tuval et al. |
| 2009/0171447 A1 | 7/2009 | Von Segesser et al. |
| 2009/0171456 A1 | 7/2009 | Kveen et al. |
| 2009/0188964 A1 | 7/2009 | Orlov |
| 2009/0216312 A1* | 8/2009 | Straubinger et al. ......... 623/1.16 |
| 2009/0216314 A1 | 8/2009 | Quadri |
| 2009/0259306 A1 | 10/2009 | Rowe |
| 2009/0276040 A1 | 11/2009 | Rowe et al. |
| 2009/0281618 A1 | 11/2009 | Hill et al. |
| 2009/0287296 A1 | 11/2009 | Manasse |
| 2009/0287299 A1 | 11/2009 | Tabor et al. |
| 2009/0292350 A1 | 11/2009 | Eberhardt et al. |
| 2009/0306768 A1 | 12/2009 | Quadri |
| 2009/0318871 A1 | 12/2009 | Zarbatany et al. |
| 2010/0036479 A1 | 2/2010 | Hill et al. |
| 2010/0082094 A1 | 4/2010 | Quadri et al. |
| 2010/0094411 A1 | 4/2010 | Tuval et al. |
| 2010/0131054 A1 | 5/2010 | Tuval et al. |
| 2010/0168839 A1 | 7/2010 | Braido et al. |
| 2010/0191326 A1 | 7/2010 | Alkhatib |
| 2010/0217382 A1 | 8/2010 | Chau et al. |
| 2010/0249894 A1 | 9/2010 | Oba et al. |
| 2010/0268332 A1 | 10/2010 | Tuval et al. |
| 2010/0298931 A1 | 11/2010 | Quadri et al. |
| 2010/0305685 A1 | 12/2010 | Millwee et al. |
| 2011/0004296 A1 | 1/2011 | Lutter et al. |
| 2011/0015731 A1 | 1/2011 | Carpentier et al. |
| 2011/0022157 A1 | 1/2011 | Essinger et al. |
| 2011/0137397 A1* | 6/2011 | Chau et al. ............... 623/1.11 |
| 2011/0178597 A9 | 7/2011 | Navia et al. |
| 2011/0202128 A1 | 8/2011 | Duffy |
| 2011/0208290 A1 | 8/2011 | Straubinger et al. |
| 2011/0208297 A1 | 8/2011 | Tuval et al. |
| 2011/0208298 A1* | 8/2011 | Tuval et al. ............... 623/2.17 |
| 2011/0224785 A1 | 9/2011 | Hacohen |
| 2011/0264196 A1 | 10/2011 | Savage et al. |
| 2011/0313515 A1 | 12/2011 | Quadri et al. |

(56) References Cited

U.S. PATENT DOCUMENTS

| | | |
|---|---|---|
| 2011/0319989 A1 | 12/2011 | Lane et al. |
| 2012/0041550 A1 | 2/2012 | Salahieh et al. |
| 2012/0053681 A1 | 3/2012 | Alkhatib et al. |
| 2012/0078353 A1 | 3/2012 | Quadri et al. |
| 2012/0101571 A1 | 4/2012 | Thambar et al. |
| 2012/0101572 A1 | 4/2012 | Kovalsky et al. |
| 2012/0179239 A1 | 7/2012 | Quadri |
| 2012/0215303 A1 | 8/2012 | Quadri et al. |
| 2012/0271398 A1 | 10/2012 | Essinger et al. |
| 2012/0303116 A1 | 11/2012 | Gorman, III et al. |
| 2013/0053950 A1 | 2/2013 | Rowe et al. |
| 2013/0110227 A1 | 5/2013 | Quadri et al. |
| 2013/0131788 A1 | 5/2013 | Quadri et al. |
| 2013/0131793 A1 | 5/2013 | Quadri et al. |
| 2013/0138203 A1 | 5/2013 | Quadri et al. |
| 2013/0138207 A1 | 5/2013 | Quadri et al. |
| 2013/0144378 A1 | 6/2013 | Quadri et al. |
| 2013/0144380 A1 | 6/2013 | Quadri et al. |
| 2013/0144381 A1 | 6/2013 | Quadri et al. |
| 2013/0184813 A1 | 7/2013 | Quadri et al. |
| 2013/0304200 A1 | 11/2013 | McLean et al. |
| 2013/0310928 A1 | 11/2013 | Morriss et al. |
| 2014/0039611 A1 | 2/2014 | Lane et al. |
| 2014/0172085 A1 | 6/2014 | Quadri et al. |
| 2014/0172086 A1 | 6/2014 | Quadri et al. |
| 2014/0222136 A1 | 8/2014 | Geist et al. |
| 2014/0277390 A1 | 9/2014 | Ratz et al. |
| 2014/0277422 A1 | 9/2014 | Ratz et al. |
| 2014/0277427 A1 | 9/2014 | Ratz et al. |
| 2015/0216655 A1 | 8/2015 | Lane et al. |
| 2015/0257878 A1 | 9/2015 | Lane et al. |

FOREIGN PATENT DOCUMENTS

| | | |
|---|---|---|
| GB | 1315844 A | 5/1973 |
| WO | WO 02/36048 A1 | 5/2002 |
| WO | WO 2006/097931 A2 | 9/2006 |
| WO | WO 2006/113906 A1 | 10/2006 |
| WO | WO-2007058857 A2 | 5/2007 |
| WO | WO 2006/097931 A3 | 7/2007 |
| WO | WO 2007/097983 A2 | 8/2007 |
| WO | WO 2007/122459 A2 | 11/2007 |
| WO | WO 2007/122459 A3 | 1/2008 |
| WO | WO 2008/013915 A2 | 1/2008 |
| WO | WO-2008005535 A2 | 1/2008 |
| WO | WO 2007/097983 A3 | 3/2008 |
| WO | WO 2008/013915 A3 | 7/2008 |
| WO | WO 2008/103722 A2 | 8/2008 |
| WO | WO 2008/103722 A3 | 10/2008 |
| WO | WO 2008/125153 A1 | 10/2008 |
| WO | WO 2009/033469 A1 | 3/2009 |
| WO | WO-2009033469 A1 | 3/2009 |
| WO | WO 2009/053497 A1 | 4/2009 |
| WO | WO-2009053497 A1 | 4/2009 |
| WO | WO 2009/108615 A1 | 9/2009 |
| WO | WO 2009/134701 A2 | 11/2009 |
| WO | WO 2010/004546 A1 | 1/2010 |
| WO | WO 2009/134701 A3 | 2/2010 |
| WO | WO 2010/037141 A1 | 4/2010 |
| WO | WO-2010057262 A1 | 5/2010 |
| WO | WO 2011/072084 A2 | 6/2011 |
| WO | WO 2011/137531 A1 | 11/2011 |
| WO | WO-2012035279 A1 | 3/2012 |

OTHER PUBLICATIONS

Bavaria. CardiAQ Valve Technologies. TCT Company Overview. Transcatheter Cardiovascular Therapeutics Conference. San Francisco, CA. Sep. 21-25, 2009.
CardiAQ Valve Technologies. Percutaneous mitral valve replacement. Start-Up. Jun. 2009; 14(6):48-49.
Carpentier-Edwards. Why compromise in the mitral position? Edwards Lifesciences. 2004.
Fitzgerald. Tomorrow's technology: percutaneous mitral valve replacement, chordal shortening and beyond. Transcatheter Valve Therapies (TVT) Conference. Seattle, WA. Jun. 7, 2010.
Mack. Advantages and limitations of surgical mitral valve replacement; lessons for the transcatheter approach. Jun. 7, 2010. Texas Cardiovascular Innovative Ventures (TCIV) Conference. Dallas, TX. Dec. 8, 2010.
Medical Devices Today. CardiAQ Valve Technologies. START-UP—Jul. 17, 2009. Accessed: Mar. 8, 2012. http:/www.medicaldevicestoday.com/2009/07/medical-device-start-up-cardiaq-valve-technologies-percutaneous-mitral-valve-replacement.html.
Ostrovsky. Transcatheter mitral valve implantation technology from CardiAQ. Posted Jan. 15, 2010. Accessed Jun. 27, 2012 from http://medgadget.com/2010/01/transcatheter_mitral_valve_implantation_technology_fr_om_cardiaq.html.
Ruiz. Overview of novel transcatheter valve technologies. Glimpse into the future. New transcatheter mitral valve treatment. Euro PCR. Paris, France. May 27, 2010.
European search report and written opinion dated Mar. 18, 2015 for EP Application No. 12851477.5.
International search report and written opinion dated Mar. 8, 2013 for PCT/CA2012/001060.
International search report and written opinion dated Sep. 27, 2011 for PCT/CA2011/000662.
Office action dated Jun. 4, 2013 for U.S. Appl. No. 13/096,572.
Al-Attar. Next generation surgical aortic biological prostheses: sutureless valves. European Society of Cardiology. Dec. 21, 2011; 10(14):1-3.
Banai, et al. Tiara: a novel catheter-based mitrel valve bioprosthesis: initial experiments and short-term pre-clinical results. J Am Coll Cardiol. Oct. 9, 2012;60(15):1430-1. doi:10.1016/j.jacc.2012.05.047. Epub Sep. 12, 2012.
Berreklouw, et al. Sutureless mitrel valve replacement with bioprostheses and Nitinol attachment rings: feasibility in acute pig experiments. J Thorac Cardiovasc Surg. Aug. 14, 2011;14(2):390-5. e1. doi: 10. 1016/j.jcvs.2010.12.018. Epub Feb. 4, 2011.
Boudjemline, et al. Steps toward the percutaneous replacement of artrioventricular valves an experimental study. J Am Coll Cardiol. Jul. 19, 2005;46(2):360-5.
Brinkman, et al. Transcatheter cardiac valve interventions. Surg Clin North Am. Aug. 2009;89(4):951-66, x. doi: 10.1016/j.suc.2009.06.004.
CardiAQ Valve Technologies to pursue first-in-man studies of its transcatheter mitral valve system. Cardiac Interventions Today. Jan. 12, 2010.
Chiam, et al. Percutaneus transcatheter aortic valve implantation: assessing results, judging outcomes, and planning trials: the interventionalist perspective. JACC Cardiovasc Interv. Aug. 2008;1(4):341-50. doi: 10.1016/j.jcin.2008.03.018.
Condado, et al. Percutaneous treatment of heart valves. Rev Esp Cardiol. Dec. 2006;59(12):1225-31.
CoreValve USA. An advanced TAVR design. Medtronic.com. Accessed Jan. 27, 2015.
De Backer, et al. Percutaneous transcatheter mitral valve replacement: an overview of devices in preclinical and early clinical evaluation. Circ Cardiovasc Interv. Jun. 2014;7(3):400-9. doi: 10.1161/CIRCINTERVENTIONS. 114.001607.
Edwards Lifesciences 2005 annual report. Accessed Jan. 27, 2015.
Fanning, et al. Transcatheter aoritc valve implantation(TAVI): valve design and evolution. Int J Cardiol. Oct. 3, 2013;168(3):1823-31.doi: 10.1016/j.ijcard.2013.07.117. Epub Aug. 20, 2013.
Gillespie, et al. Sutureless mitral valve replacement: initial steps toward a percutaneous procedure. Ann Thorac Surg. Aug. 2013;96(2):670-4. doi:10.1016/j.athoracsur.2013.02.065.
Grube, et al. Percutaneous implantation of the CoreValve self-expanding valve prosthesis in high-risk patients with aortic valve disease: the Siegburg first-in-man study. Circulation. Oct. 10, 2006;114(15):1616-24. Epub Oct. 2, 2006.
Harmon, et al. Effect of acute myocardial infarction on the angle between the mitral and aortic valve plane. Am J Cardiol. Aug. 1, 1999;84(3):342-4, A8.
Herrman. Transcatheter mitral valve implantation. Cardiac Interventions Today. Aug./Sep. 2009; 81-85.

(56) References Cited

OTHER PUBLICATIONS

Ionasec, et al. Personalized modeling and assessment of the aortic-mitral coupling from 4D TEE and CT. Med Image Comput Assist Interv. 2009;12(Pt 2):767-75.
Karimi, et al. Percutaneous Valve Therapies. SIS 2007 Year book. Chapter 11. 11 pages.
Kumar, et al. Design considerations and quantitative assessment for the development of percutaneous mitral valve stent. Med Eng Phys. Jul. 2014;36(7):882-8. doi: 10.1016/j.medengphy.2014.03.010. Epub Apr. 16, 2014.
Lauten; et al., "Experimental evaluation of the JenaClip transcatheter aortic valve.", Sep. 1, 2009, 74(3), 514-9.
Leon, et al. Transcatheter aortic valve replacement in patients with critical aortic stenosis: rationale, device descriptions, early clinical experiences, and perspectives. Semin Thorac Cardiovasc Surg. 2006 Summer;18(2):165-74.
Lozonschi, et al. Transapical mitral valved stent implantation. Ann Thorac Surg. Sep. 2008;86(3):745-8. doi: 10.1016/j.athroacsur.2008.05.039.
Lutter, et al. Off-pump transapical mitral valve replacement. Eur J Cardiothorac Surg. Jul. 2009;36(1):124-8; discussion 128. doi: 10.1016/j.ejcts.2009.02.027. Epub Apr. 25, 2009.
Lutter, et al. Transapical mitral valve implantation: the Lutter valve. Heart Lung Vessel. 2013;5(4):201-6.
Ma, et al. Double-crowned valved stents for off-pump mitral valve replacement. Eur J Cardiothroac Surg. Aug. 2008;(2):194-8; discussion 198-9.
Maisano, et al. Mitral transcatheter technologies. Rambam Maimonides Med J. Jul. 25, 2013;4(3):e0015. doi: 10.5041/RMMJ.10115. Print Jul. 2013.
Navia, et al. Sutureless implantation a expandable mitral stent-valve prosthesis in acute animal model. TCT728. JACC. Nov. 8, 2011. vol. 58, No. 20 Suppl B. B194.
Orton. Mitralseal: hybrid transvatheter mitral valve replacement. Colorado State University. 20111; 311-312. https://www.acvs.org/files/proceedings/2011/data/papers/102.pdf.
Piazza, et al. Anatomy of the aortic valvar complex and its implications for transcatheter implantation of the aortic valve. Circ Cardiovasc Interv. Aug. 2008;1(1):74-81. doi: 10.1161/CIRCINTERVENTIONS.108.780858.
Pluth, et al. Aortic and mitral valve replacement with cloth-covered Braunwald-Cutter prosthesis. A three-year follow-up. Ann Thorac Surg. Sep. 1975;20(3):329-48.
Preston-Maher, et al. A Technical Review of Minimally Invasive Mitral Valve Replacements. Cardiovasc Eng Technol. 2015;6(2):174-184. Epub Nov. 25, 2014.
Quadri, et al. CVT is developing a non-surgical approach to replacing mitral valves that may be the alternative to open-chest surgery. CardiAQ Valve Technologies. May 8, 2009.
Ribiero, et al. Balloon-expandable prostheses for transvatheter aortic valve replacement. Prog Cardiovascular Dis, May-Jun. 2014;56(6):582-95, doi: 10.1016/j.pcad.2014.02.001. Epub Mar. 1, 2014.
Seidel, et al. A mitral valve prosthesis and a study of thrombosis on heart valves in dogs. J Surg Res. May 1962;2:168-75.
Shuto, et al. Percutaneous transvenous Melody valve-in-ring procedure for mitral valve replacement. J Am Coll Cardiol. Dec. 6, 2011;58(24):2475-80. doi: 10.1016/j.jacc.2011.09.021.
Sondergaard, et al. First-in-human CardiAQ transcatheter mitral valve implantation via transapical approach. TCT-811. JACC. Sep. 13, 2014. vol. 64, No. 11 Suppl B. B237.
Spencer, et al. Surgical treatment of valvular heart disease. Part V. Prosthetic replacement of the mitral valve. American Heart Journal. Oct. 1968; 76(4):576-580.
Spillner, et al. New Sutureless 'atrial mitral-valve prosthesis' for minimally invasive mitral valve therapy. Textile Research Journal. 2010:1-7.
TAVR. Engager system. Precise Valve positioning. Accessed Jan. 28, 2015.
The JeanValve—the prosthesis. JenaValve Technology. Accessed Jan. 28, 2015.
Timek, et al. Aorto-mitral annular dynamics. Ann Thorac Surg. Dec. 2003;76(6):1994-50.
Tsang, et al. Changes in aortic-mitral coupling with severe aortic stenosis. JACC. Mar. 9, 2010; vol. 55. Issue 1A.
Veronesi, et al. A study of functional anatomy of aortic-mitral valve coupling using 3D matrix transesophageal echocardiography. Circ Cardiovasc Imaging. Jan. 2009;2(1):24-31. doi: 10.1161/CIRCIMAGING.108.78597. Epub Dec. 2, 2008.
Vu, et al. Novel sutureless mitral valve implantation method involving a bayonet insertion and release mechanism: a proof of concept in pigs. J Thorac Cardiovasc Surg. Apr. 2012;143(4):985-8. doi: 10.1016/j.jcvs.2012.01.037. Epub Feb. 11, 2012.
Walther, et al. Transapical approach for sutureless stent-fixed aortic valve implantation: experimental results. Eur J Cardiothorac Surg. May 2006;29(5):703-8. Epub Apr. 5, 2006.
Webb, et al. Transcatheter aortic valve implantation: the evolution of prostheses, delivery systems and approaches. Arch Cardiovasc Dis. Mar. 2012;105(3):153-9. doi: 10.1016/j.acvd.2012.02.001. Epub Mar. 16, 2012.
European search report and opinion dated Dec. 10, 2013 for EP Application No. 11777065.1.
Ratz. CardiAQ Valve Technologies. Innovations in heartvalve therapy. In3 San Francisco. Jun. 18, 2008. PowerPoint presentation in 19 slides.
Office action dated Aug. 12, 2015 for U.S. Appl. No. 14/685,418.
Office action dated Aug. 14, 2015 for U.S. Appl. No. 14/692,605.
Notice of allowance dated Nov. 5, 2015 for U.S. Appl. No. 14/692,605.
Office action dated Sep. 18, 2015 for U.S. Appl. No. 14/046,606.
Notice of allowance dated Dec. 2, 2015 for U.S. Appl. No. 14/685,418.

* cited by examiner

SEQUENTIALLY DEPLOYED TRANSCATHETER MITRAL VALVE PROSTHESIS

CROSS-REFERENCE

The present application is a non-provisional of, and claims the benefit of U.S. Provisional Patent Application No. 61/563,156 filed Nov. 23, 2011; the entire contents of which are incorporated herein by reference.

The present application is related to U.S. patent application Ser. No. 13/096,572 filed Apr. 28, 2011, the entire contents of which are incorporated herein by reference.

BACKGROUND OF THE INVENTION

1. Field of the Invention

The present invention generally relates to medical devices and methods, and more particularly relates to the treatment of valve insufficiency, such as mitral insufficiency, also referred to as mitral regurgitation. The use of prosthetic valves delivered by traditional surgical implantation methods, or by a less invasive percutaneous catheter or by minimally invasive transapical methods are one possible treatment for valvar insufficiency (also referred to as regurgitation).

The heart of vertebrate animals is divided into four chambers, and is equipped with four valves (the mitral, aortic, pulmonary and tricuspid valves) that ensure that blood pumped by the heart flows in a forward direction through the cardiovascular system. The mitral valve of a healthy heart prevents the backflow of blood from the left ventricle into the left atrium of the heart, and comprises two flexible leaflets (anterior and posterior) that close when the left ventricle contracts. The leaflets are attached to a fibrous annulus, and their free edges are tethered by subvalvular chordae tendineae to papillary muscles in the left ventricle to prevent them from prolapsing into the left atrium during the contraction of the left ventricle.

Various cardiac diseases or degenerative changes may cause dysfunction in any of these portions of the mitral valve apparatus, causing the mitral valve to become abnormally narrowed or dilated, or to allow blood to leak (i.e. regurgitate) from the left ventricle back into the left atrium. Any such impairments compromise cardiac sufficiency, and can be debilitating or life threatening.

Numerous surgical methods and devices have accordingly been developed to treat mitral valve dysfunction, including open-heart surgical techniques for replacing, repairing or re-shaping the native mitral valve apparatus, and the surgical implantation of various prosthetic devices such as annuloplasty rings to modify the anatomy of the native mitral valve. More recently, less invasive transcatheter techniques for the delivery of replacement mitral valve assemblies have been developed. In such techniques, a prosthetic valve is generally mounted in a crimped state on the end of a flexible catheter and advanced through a blood vessel or the body of the patient until the valve reaches the implantation site. The prosthetic valve is then expanded to its functional size at the site of the defective native valve.

While these devices and methods are promising treatments for valvar insufficiency, they can be difficult to deliver, expensive to manufacture, or may not be indicated for all patients. Therefore, it would be desirable to provide improved devices and methods for the treatment of valvar insufficiency such as mitral insufficiency. At least some of these objectives will be met by the devices and methods disclosed below.

2. Description of the Background Art

By way of example, PCT international patent number PCT/US2008/054410 (published as PCT international publication no. WO2008/103722), the disclosure of which is hereby incorporated by reference, describes a transcatheter mitral valve prosthesis that comprises a resilient ring, a plurality of leaflet membranes mounted with respect to the ring so as to permit blood flow therethrough in one direction, and a plurality of tissue-engaging positioning elements movably mounted with respect to the ring and dimensioned to grip the anatomical structure of the heart valve annulus, heart valve leaflets, and/or heart wall. Each of the positioning elements defines respective proximal, intermediate, and distal tissue engaging regions cooperatively configured and dimensioned to simultaneously engage separate corresponding areas of the tissue of an anatomical structure, and may include respective first, second, and third elongate tissue-piercing elements. The valve prosthesis may also include a skirt mounted with respect to the resilient ring for sealing a periphery of the valve prosthesis against a reverse flow of blood around the valve prosthesis.

PCT international patent number PCT/US2009/041754 (published as PCT international publication no. WO2009/134701), the disclosure of which is hereby incorporated by reference, describes a prosthetic mitral valve assembly that comprises an anchor or outer support frame with a flared upper end and a tapered portion to fit the contours of the native mitral valve, and a tissue-based one-way valve mounted therein. The assembly is adapted to expand radially outwardly and into contact with the native heart tissue to create a pressure fit, and further includes tension members anchoring the leaflets of the valve assembly to a suitable location on the heart to function as prosthetic chordae tendineae.

Also known are prosthetic mitral valve assemblies that utilize a claw structure for attachment of the prosthesis to the heart (see, for example, U.S. patent publication no. US2007/0016286 to Hermann et al., the disclosure of which is hereby incorporated by reference), as are prosthetic mitral valve assemblies that rely on the application of axial rather than radial clamping forces to facilitate the self-positioning and self-anchoring of the prosthesis with respect to the native anatomical structure.

Another method which has been proposed as a treatment of mitral valve regurgitation is the surgical bow tie method, which recently has been adapted into a minimally invasive catheter based treatment where an implant is used to clip the valve leaflets together. This procedure is more fully disclosed in the scientific and patent literature, such as in U.S. Pat. No. 6,629,534 to St. Goar et al., the entire contents of which are incorporated herein by reference.

Other relevant publications include U.S. patent publication no. 2011/0015731 to Carpentier et al. and WO2011/137531 to Lane et al. While some of these devices and methods are promising, there still is a need for improved devices and methods that will further allow more accurate positioning of a prosthetic valve and that will also more securely anchor the valve in place. At least some of these objectives will be met by the exemplary embodiments disclosed herein.

SUMMARY OF THE INVENTION

The present invention generally relates to medical devices and methods, and more particularly prosthetic valves used to treat mitral regurgitation. While the present disclosure focuses on the use of a prosthetic valve for treating mitral regurgitation, this is not intended to be limiting. The prosthetic valves disclosed herein may also be used to treat other body valves including other heart valves or venous valves. Exemplary heart valves include the aortic valve, the tricuspid valve, or the pulmonary valve.

In a first aspect of the present invention, a method of delivering an implantable prosthetic valve to a patient's heart which has a mitral valve with an anterior leaflet and a posterior leaflet, comprises providing a prosthetic valve, wherein the prosthetic valve comprises an expandable frame having a first end, a second end opposite the first end, a first anterior tab on an anterior portion of the expandable frame, a posterior tab on a posterior portion of the expandable frame, and a ventricular skirt adjacent the first end of the expandable frame. The prosthetic valve has an expanded configuration for engaging the heart and a collapsed configuration. The prosthetic valve is delivered in the collapsed configuration to the patient's heart adjacent the mitral valve, and the first anterior tab is expanded radially outward such that a tip portion of the first anterior tab engages a first fibrous trigone on a first side of the anterior leaflet of the mitral valve. The anterior chordae tendineae adjacent the anterior leaflet are disposed between the first anterior tab and an outer anterior surface of the ventricular skirt. After radially expanding the first anterior tab, the posterior tab is radially expanded outward such that the posterior leaflet of the mitral valve and adjacent posterior chordae tendinae are disposed between the posterior tab and an outer posterior surface of the ventricular skirt. After radially expanding the posterior tab, the ventricular skirt is radially expanded outward thereby engaging the anterior and posterior leaflets. The anterior leaflet and the adjacent anterior chordae tendinae are captured between the first anterior tab and the outer anterior surface of the ventricular skirt. The posterior leaflet and the adjacent posterior chordae tendinae are captured between the posterior tab and the posterior outer surface of the ventricular skirt.

In another aspect of the present invention, a method of delivering an implantable prosthetic valve to a patient's heart having a mitral valve with an anterior leaflet and a posterior leaflet, comprises providing a prosthetic valve, wherein the prosthetic valve comprises an expandable frame having a first end, a second end opposite the first end, a first anterior tab on an anterior portion of the expandable frame, a posterior tab on a posterior portion of the expandable frame, and a ventricular skirt adjacent the first end of the expandable frame. The prosthetic valve has an expanded configuration for engaging the heart and a collapsed configuration. The prosthetic valve is delivered in the collapsed configuration to the patient's heart adjacent the mitral valve. The first anterior tab is expanded radially outward such that a tip portion of the first anterior tab engages a first fibrous trigone on a first side of the anterior leaflet of the mitral valve. The anterior leaflet and adjacent anterior chordae tendineae are disposed between the first anterior tab and an outer anterior surface of the ventricular skirt. After radially expanding the first anterior tab, the ventricular skirt is radially expanded outward thereby engaging the anterior leaflet such that the anterior leaflet and the adjacent anterior chordae tendinae are captured between the first anterior tab and the outer anterior surface of the ventricular skirt. After radially expanding the ventricular skirt, the posterior tab is radially expanded outward such that the posterior leaflet of the mitral valve and adjacent posterior chordae tendineae are disposed and captured between the posterior tab and an outer posterior surface of the ventricular skirt.

The method may further comprise providing a delivery catheter, wherein the prosthetic valve is releasably coupled thereto. Delivering the prosthetic valve may comprise transapical delivery of the prosthetic valve from a region outside the heart to the left ventricle of the heart, or the prosthetic valve may be delivered transseptally from the right atrium to the left atrium of the heart. Delivering the prosthetic valve may comprise positioning the prosthetic valve across the mitral valve so that the first end of the expandable frame is inferior to a portion of the mitral valve and the second end of the expandable frame is superior to a portion of the mitral valve.

Expanding the first anterior tab may comprise retracting a constraining sheath from the first anterior tab so that the first anterior tab is free to self-expand radially outward. The prosthetic valve may further comprise a second anterior tab on the anterior portion of the expandable frame, and the method may further comprise expanding the second anterior tab radially outward such that a tip portion of the second anterior tab engages a second fibrous trigone on a second side of the anterior leaflet opposite the first side of the anterior leaflet. The anterior leaflet and adjacent anterior chordae tendineae may be disposed between the second anterior tab and an outer surface of the ventricular skirt. The second anterior tab may expand radially outward concurrently with expansion of the first anterior tab. Prior to engaging the first fibrous trigone or the second fibrous trigone with the respective first or second anterior tab, and prior to disposing the anterior leaflet and the adjacent chordae tendineae between the first or second anterior tab and the outer surface of the ventricular skirt, the method may comprise partially expanding the first or the second anterior tab radially outward such that the first or the second anterior tab is transverse to a longitudinal axis of the prosthetic valve. Expanding the second anterior tab may comprise retracting a constraining sheath from the second anterior tab so that the second anterior tab is free to self-expand radially outward.

In some embodiments, prior to disposing the posterior leaflet of the mitral valve and the adjacent posterior chordae tendineae between the posterior tab and the outer posterior surface of the ventricular skirt, the method may comprise partially expanding the posterior tab radially outward such that the posterior tab is transverse to a longitudinal axis of the prosthetic valve. After the anterior leaflet and the adjacent anterior chordae tendineae are disposed between the first anterior tab and the outer anterior surface of the ventricular skirt, the method may comprise partially expanding the posterior tab radially outward such that the posterior tab is transverse to a longitudinal axis of the prosthetic valve, and wherein the posterior tab is partially expanded without disposing the posterior leaflet of the mitral valve and the adjacent posterior chordae tendinae between the posterior tab and the outer posterior surface of the ventricular skirt.

Radially expanding the ventricular skirt may comprise retracting a constraining sheath from the ventricular skirt so that the ventricular skirt is free to self-expand radially outward. The ventricular skirt may comprise a plurality of barbs, and expanding the ventricular skirt may comprise anchoring the plurality of barbs into heart tissue. The prosthetic valve may further comprise a plurality of commissures, and expanding the ventricular skirt may displace the anterior and posterior mitral valve leaflets radially outward thereby preventing interference between the commissures and both of the anterior and posterior leaflets. Expanding the ventricular skirt may displace the anterior and posterior valve leaflets radially outward without contacting an inner wall of the left ventricle, and without obstructing the left ventricular outflow tract. Expanding the ventricular skirt may expand the ventricular skirt asymmetrically such that an anterior portion of the ventricular skirt is substantially flat, and a posterior portion of the ventricular skirt is cylindrically shaped.

The method may further comprise reducing or eliminating mitral regurgitation. In some embodiments, the prosthetic valve may carry a therapeutic agent, and the method may further comprise eluting the therapeutic agent from the prosthetic valve into adjacent tissue. The prosthetic valve may also comprise an alignment element. A second fibrous trigone is disposed on a second side of the anterior leaflet opposite the first side of the anterior leaflet, and the method may further comprise aligning the alignment element with an aortic root and disposing the alignment element between the first and second fibrous trigones. Aligning the alignment element may comprise rotating the prosthetic valve.

The prosthetic valve may further comprise a plurality of commissures with a covering disposed thereover whereby a plurality of prosthetic valve leaflets are formed, and the method may further comprise releasing the plurality of prosthetic valve leaflets from a delivery catheter. The plurality of prosthetic valve leaflets may form a tricuspid valve that has an open configuration and a closed configuration. The plurality of prosthetic valve leaflets may be disposed away from one another in the open configuration thereby permitting antegrade blood flow therethrough, and the plurality of prosthetic valve leaflets may engage one another in the closed configuration thereby substantially preventing retrograde blood flow therethrough.

The prosthetic valve may further comprise an atrial skirt, and the method may further comprise expanding the atrial skirt radially outward so as to lie over a superior surface of the mitral valve, and engaging the atrial skirt against the superior surface of the mitral valve. Expanding the atrial skirt may comprise retracting a constraining sheath from the atrial skirt so that the atrial skirt is free to self-expand radially outward. The prosthetic valve may be moved upstream or downstream relative to the mitral valve to ensure that the atrial skirt engages the superior surface of the mitral valve. Engaging the atrial skirt against the superior surface may seal the atrial skirt against the superior surface of the mitral valve to prevent or substantially prevent blood flow therebetween.

The prosthetic valve may further comprise an annular region, and the method may further comprise expanding the annular region radially outward so as to conform with an annulus of the mitral valve, and engaging the annular region with the mitral valve annulus. Expanding the annular region may comprise retracting a constraining sheath from the annular region so that the annular region is free to self-expand radially outward. Expanding the annular region may comprise asymmetrically expanding the annular region such that an anterior portion of the annular region is substantially flat, and a posterior portion of the annular region is cylindrically shaped.

In another aspect of the present invention, a sequentially deployed prosthetic cardiac valve comprises a self-expanding frame having a first end, a second end opposite the first end, an atrial region near the second end, and a ventricular region near the first end. The self-expanding frame has an expanded configuration and a collapsed configuration. The expanded configuration is adapted to engage heart tissue, and the collapsed configuration is adapted to be delivered to a patient's heart. The prosthetic valve also includes a self-expanding atrial skirt disposed in the atrial region, a self-expanding ventricular skirt disposed in the ventricular region and a self-expanding annular region disposed between the atrial region and the ventricular region. A first self-expanding anterior tab is disposed on an anterior portion of the self-expanding frame in the ventricular region. A self-expanding posterior tab is disposed on a posterior portion of the self-expanding frame in the ventricular region. A portion of the first self-expanding anterior tab and a portion of the self-expanding posterior tab partially self-expand radially outward when a constraint is removed therefrom. The first anterior tab fully self-expands radially outward before the posterior tab fully self-expands radially outward when the constraint is removed therefrom. The posterior tab fully self-expands radially outward before ventricular skirt self-expands when the constraint is removed therefrom, and the ventricular skirt fully expands last.

In another aspect of the present invention, a sequentially deployed prosthetic cardiac valve comprises a self-expanding frame having a first end, a second end opposite the first end, an atrial region near the second end, and a ventricular region near the first end. The self-expanding frame has an expanded configuration and a collapsed configuration. The expanded configuration is adapted to engage heart tissue, and the collapsed configuration is adapted to be delivered to a patient's heart. The prosthetic cardiac valve also comprises a self-expanding atrial skirt disposed in the atrial region, a self-expanding ventricular skirt disposed in the ventricular region, and a self-expanding annular region disposed between the atrial region and the ventricular region. A first self-expanding anterior tab is disposed on an anterior portion of the self-expanding frame in the ventricular region. A self-expanding posterior tab is disposed on a posterior portion of the self-expanding frame in the ventricular region. A portion of the first self-expanding anterior tab and a portion of the self-expanding posterior tab partially self-expand radially outward when a constraint is removed therefrom. The first anterior tab self-expands radially outward before the ventricular skirt self-expands radially outward when the constraint is removed therefrom. The ventricular skirt self-expands radially outward before the posterior tab finishes self-expanding, and the posterior tab finishes self-expanding after the ventricular skirt self-expands.

At least a portion of the atrial skirt may be covered with tissue or a synthetic material. The atrial skirt may have a collapsed configuration and an expanded configuration. The collapsed configuration may be adapted for delivery to a patient's heart, and the expanded configuration may be radially expanded relative to the collapsed configuration and may be adapted to lie over a superior surface of the patient's native mitral valve, thereby anchoring the atrial skirt against a portion of the left atrium. The atrial skirt may comprise one or more radiopaque markers and may comprise a plurality of axially oriented struts connected together with a connector element thereby forming interconnected struts into a series of peaks and valleys. After self-expansion of the atrial skirt, the atrial skirt may form a flanged region adjacent the second end of the self-expanding frame. Also after self-expansion, the atrial skirt may have an asymmetrically D-shaped cross-section having a substantially flat anterior portion, and a cylindrically shaped posterior portion. The prosthetic valve may further comprise an alignment element coupled to an anterior portion of the atrial skirt, and the alignment element may be aligned with an aortic root of a patient's heart and may be disposed between two fibrous trigones of an anterior leaflet of the patient's mitral valve.

At least a portion of the annular region may be covered with tissue or a synthetic material. The annular region may have a collapsed configuration and an expanded configuration. The collapsed configuration may be adapted for delivery to the patient's heart, and the expanded configuration may be radially expanded relative to the collapsed configuration and may be adapted to conform with and adapted to engage an annulus of a patient's native mitral valve. After self-expanding, the annular region may have an asymmetrically D-shaped cross-section having a substantially flat anterior portion, and a cylindrically shaped posterior portion. The annular region may comprise a plurality of axially oriented struts connected together with a connector element, and the plurality of interconnected struts may form a series of peaks and valleys. One or more of the plurality of axially oriented struts may comprise one or more suture holes extending therethrough, and the suture holes may be sized to receive a suture.

At least a portion of the ventricular skirt may be covered with tissue or a synthetic material. After self-expanding, the ventricular skirt may comprise an asymmetrically D-shaped cross-section having a substantially flat anterior portion, and a cylindrically shaped posterior portion. The ventricular skirt may have a collapsed configuration and an expanded configuration. The collapsed configuration may be adapted for delivery to the patient's heart, and the expanded configuration may be radially expanded relative to the collapsed configuration and may be adapted to displace native mitral valve leaflets radially outward.

The first anterior tab may have a tip portion adapted to engage a first fibrous trigone on a first side of an anterior leaflet of a patient's mitral valve, and the first anterior tab may also be adapted to capture the anterior leaflet and adjacent chordae tendineae between the first anterior tab and an outer anterior surface of the ventricular skirt. The prosthetic cardiac valve may further comprise a second self-expanding anterior tab disposed on the anterior portion of the self-expanding frame in the ventricular region. The second anterior tab may have a tip portion adapted to engage a second fibrous trigone on a second side of the anterior leaflet of the patient's mitral valve opposite the first side of the anterior leaflet. The second anterior tab may be adapted to capture the anterior leaflet and adjacent chordae tendineae between the second anterior tab and the outer surface of the ventricular skirt. The first or the second anterior tabs may have a cover disposed thereover that increases the contact area between the tab and the cardiac tissue. The cover may include a fabric disposed over a polymer tab that is coupled to the first or second tab. The posterior tab may be adapted to being anchored over a posterior leaflet of the patient's mitral valve, such that the posterior tab is seated between the posterior leaflet and a ventricular wall of a patient's heart. The posterior tab may comprise a plurality of struts, and adjacent struts may be coupled together to form a plurality of expandable hinged joints. Upon radial expansion of the posterior tab, the plurality of struts may move away from one another thereby opening the hinged joints forming an elongate horizontal section which allows engagement and anchoring of the posterior tab with the sub-annular region between the posterior leaflet and the ventricular wall. Thus, the elongate horizontal section contacts a larger region of the sub-annular region as compared with a posterior tab that only has a tapered tip formed from a single hinge between struts. The ventricular skirt may further comprise a plurality of barbs coupled thereto. The plurality of barbs may be adapted to anchor the ventricular skirt into heart tissue. The ventricular skirt may also comprise a plurality of struts connected together with a connector element, and the plurality of interconnected struts may form a series of peaks and valleys. One or more of the struts may comprise one or more suture holes extending therethrough, the suture holes sized to receive a suture.

The prosthetic cardiac valve may further comprise a plurality of prosthetic valve leaflets. Each of the leaflets may have a first end and a free end, and the first end may be coupled with the self-expanding frame and the free end may be opposite of the first end. The prosthetic valve leaflets may have an open configuration in which the free ends of the prosthetic valve leaflets are disposed away from one another to allow antegrade blood flow therepast. The prosthetic valve leaflets may have a closed configuration in which the free ends of the prosthetic valve leaflets engage one another and substantially prevent retrograde blood flow therepast. The plurality of prosthetic valve leaflets may form a tricuspid valve. At least a portion of one or more prosthetic valve leaflets may comprise tissue or a synthetic material. One or more of the prosthetic valve leaflets may comprise a commissure post having a commissure tab, and the commissure tab may be adapted to be releasably engaged with a delivery device. The prosthetic cardiac valve may carry a therapeutic agent that is adapted to being eluted therefrom.

In still another aspect of the present invention, a delivery system for delivering a prosthetic cardiac valve to a patient's heart having a mitral valve with an anterior leaflet and a posterior leaflet, comprises a prosthetic cardiac valve, an inner guidewire shaft having a lumen extending therethrough, where the lumen is sized to slidably receive a guidewire, and a distal tissue penetrating tip coupled to a distal portion of the inner guidewire shaft. The distal tip is adapted to pass through and expand tissue in the heart, and a continuous flared region couples the inner guidewire shaft with the distal tip. The continuous flared region is configured to support the prosthetic cardiac valve thereby reducing or eliminating unwanted bending of the prosthetic cardiac valve. The delivery system also comprises a hub shaft concentrically disposed over the inner guidewire shaft. The prosthetic cardiac valve is releasably coupled to a distal portion of the hub shaft. A bell shaft is slidably and concentrically disposed over the hub shaft, and an outer sheath is slidably and concentrically disposed over the bell shaft. The prosthetic cardiac valve is housed in the outer sheath in a radially collapsed configuration. The delivery system also has a handle near a proximal end of the delivery system. The handle comprises an actuator mechanism adapted to advance and retract the bell shaft and the sheath. Proximal retraction of the outer sheath relative to the bell shaft may remove a constraint from the prosthetic cardiac valve thereby allowing the prosthetic cardiac valve to self-expand into engagement with the patient's mitral valve. The prosthetic cardiac valve may comprise a plurality of commissure posts, and the commissure posts may be releasably coupled with a distal portion of the hub shaft. Proximal retraction of the bell shaft relative to the hub shaft allows the commissure posts to uncouple from the hub shaft. The actuator mechanism may comprise a rotatable wheel.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Specific embodiments of the disclosed device, delivery system, and method will now be described with reference to the drawings. Nothing in this detailed description is intended to imply that any particular component, feature, or step is essential to the invention.

Figure 1:
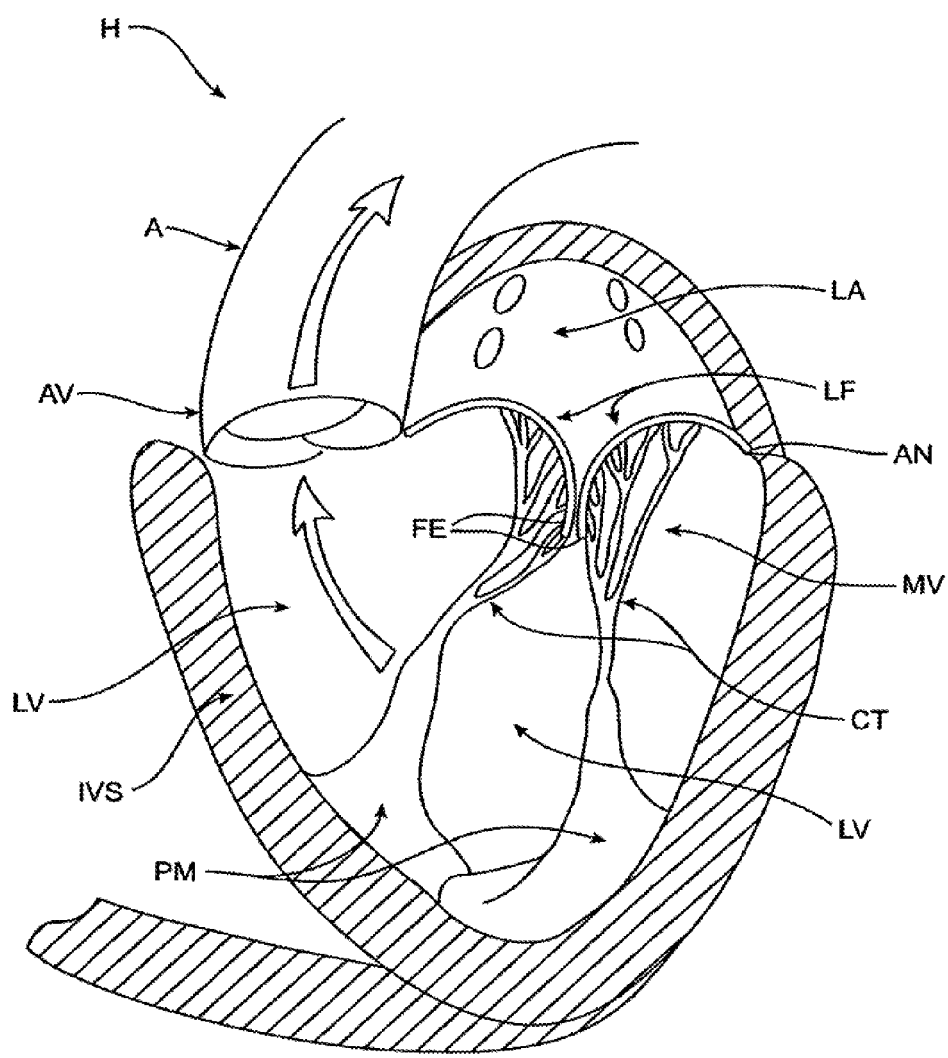
FIG. 1 is a schematic illustration of the left ventricle of a heart showing blood flow during systole with arrows.

Cardiac Anatomy. The left ventricle LV of a normal heart H in systole is illustrated in FIG. 1. The left ventricle LV is contracting and blood flows outwardly through the aortic valve AV, a tricuspid valve in the direction of the arrows. Back flow of blood or "regurgitation" through the mitral valve MV is prevented since the mitral valve is configured as a "check valve" which prevents back flow when pressure in the left ventricle is higher than that in the left atrium LA. The mitral valve MV comprises a pair of leaflets having free edges FE which meet evenly to close, as illustrated in FIG. 1. The opposite ends of the leaflets LF are attached to the surrounding heart structure along an annular region referred to as the annulus AN. The free edges FE of the leaflets LF are secured to the lower portions of the left ventricle LV through chordae tendineae CT (also referred to herein as the chordae) which include a plurality of branching tendons secured over the lower surfaces of each of the valve leaflets LF. The chordae CT in turn, are attached to the papillary muscles PM which extend upwardly from the lower portions of the left ventricle and interventricular septum IVS.

Figure 2:
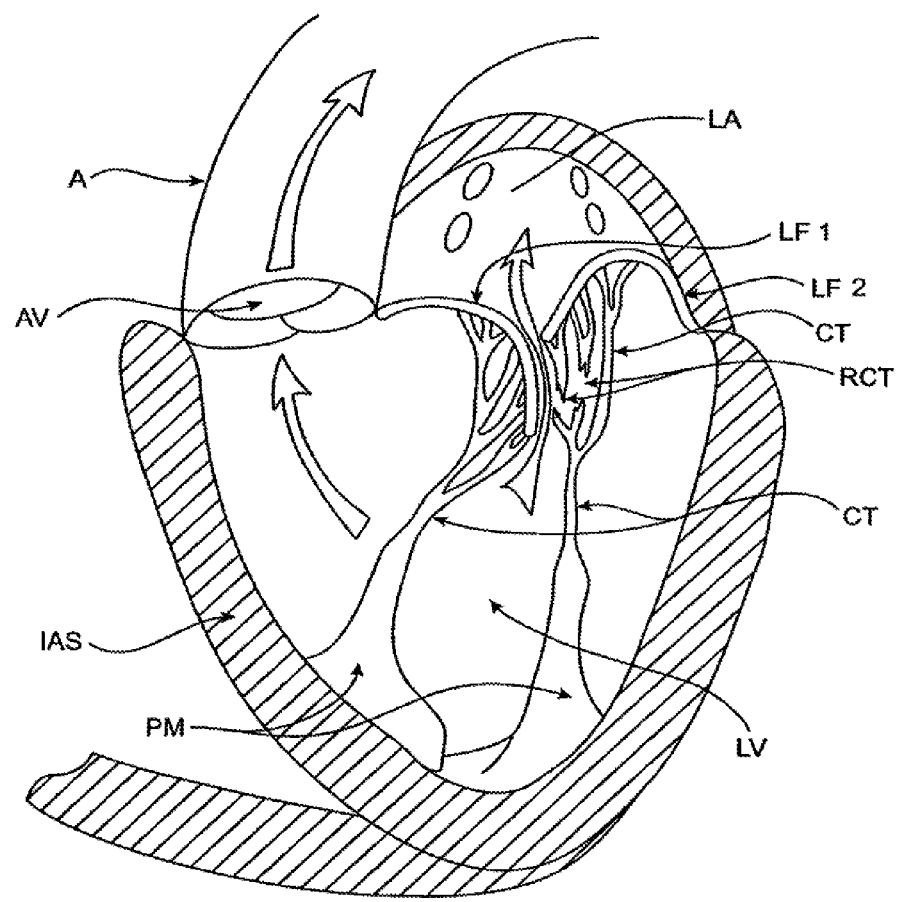
FIG. 2 is a schematic illustration of the left ventricle of a heart having prolapsed leaflets in the mitral valve.
Figure 3:
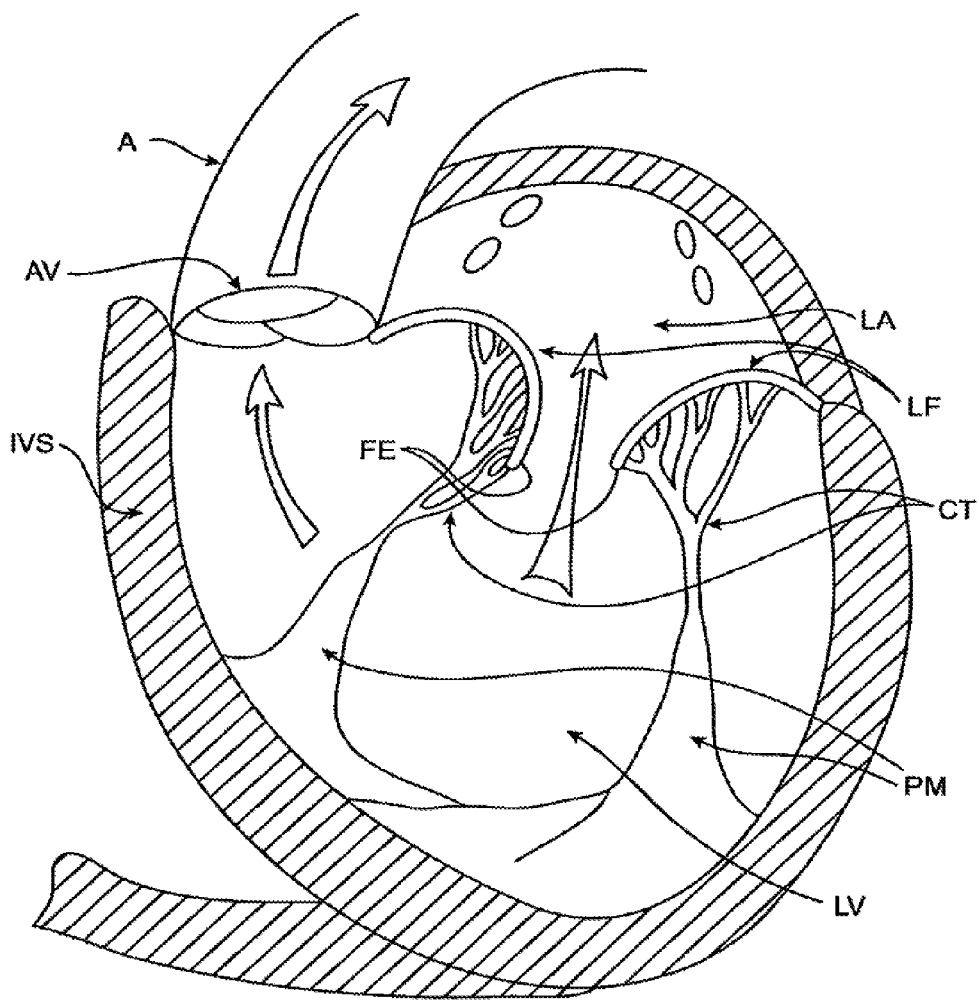
FIG. 3 is a schematic illustration of a heart in a patient suffering from cardiomyopathy where the heart is dilated and the leaflets do not meet.
Figure 4:
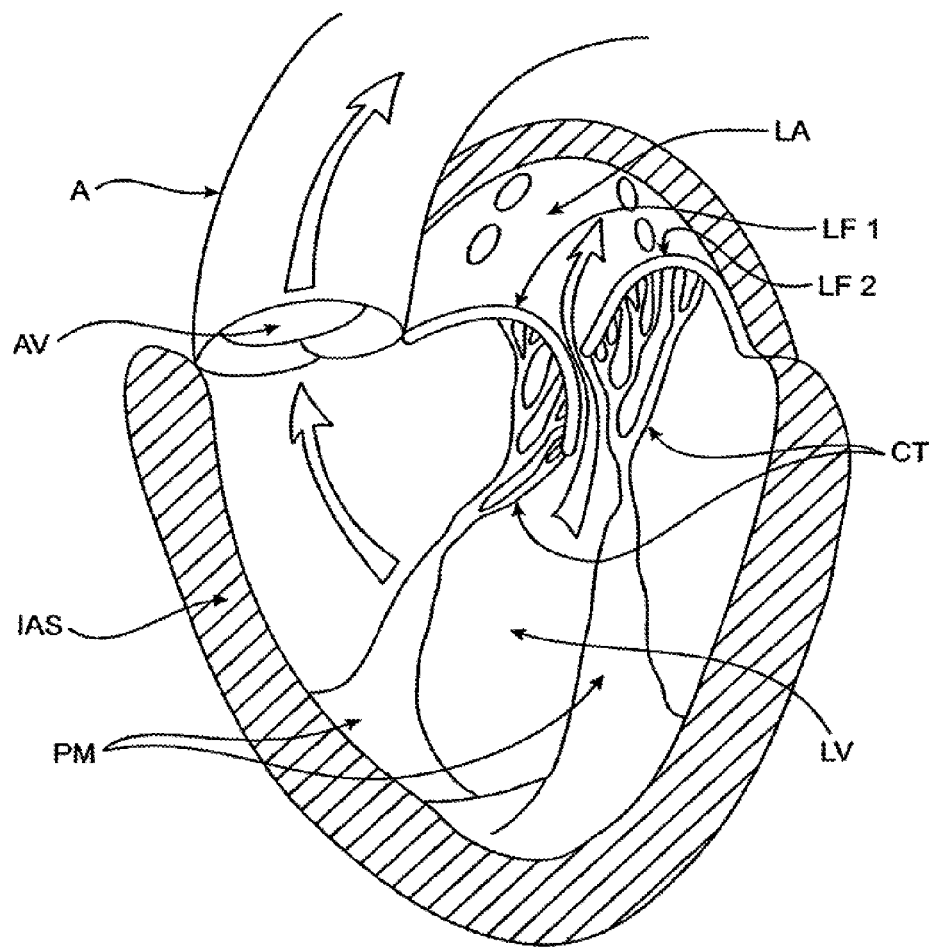
FIG. 4 illustrates mitral valve regurgitation in the left ventricle of a heart having impaired papillary muscles.

Referring now to FIGS. 2-4, a number of structural defects in the heart can cause mitral valve regurgitation. Ruptured chordae RCT, as shown in FIG. 2, can cause a valve leaflet LF2 to prolapse since inadequate tension is transmitted to the leaflet via the chordae. While the other leaflet LF1 maintains a normal profile, the two valve leaflets do not properly meet and leakage from the left ventricle LV into the left atrium LA will occur, as shown by the arrow.

Figure 3A:
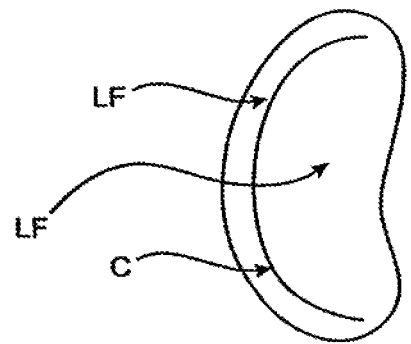
FIG. 3A shows normal closure of the valve leaflets.
Figure 3B:
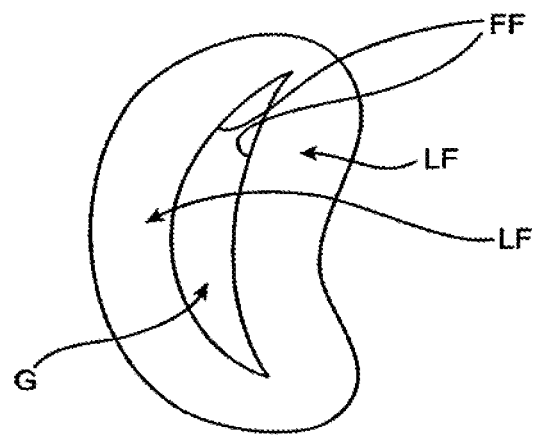
FIG. 3B shows abnormal closure of the valve leaflets.

Regurgitation also occurs in the patients suffering from cardiomyopathy where the heart is dilated and the increased size prevents the valve leaflets LF from meeting properly, as shown in FIG. 3. The enlargement of the heart causes the mitral annulus to become enlarged, making it impossible for the free edges FE to meet during systole. The free edges of the anterior and posterior leaflets normally meet along a line of coaptation C as shown in FIG. 3A, but a significant gap G can be left in patients suffering from cardiomyopathy, as shown in FIG. 3B.

Mitral valve regurgitation can also occur in patients who have suffered ischemic heart disease where the functioning of the papillary muscles PM is impaired, as illustrated in FIG. 4. As the left ventricle LV contracts during systole, the papillary muscles PM do not contract sufficiently to effect proper closure. The leaflets LF1 and LF2 then prolapse, as illustrated. Leakage again occurs from the left ventricle LV to the left atrium LA, as shown by the arrow.

Figure 5A:
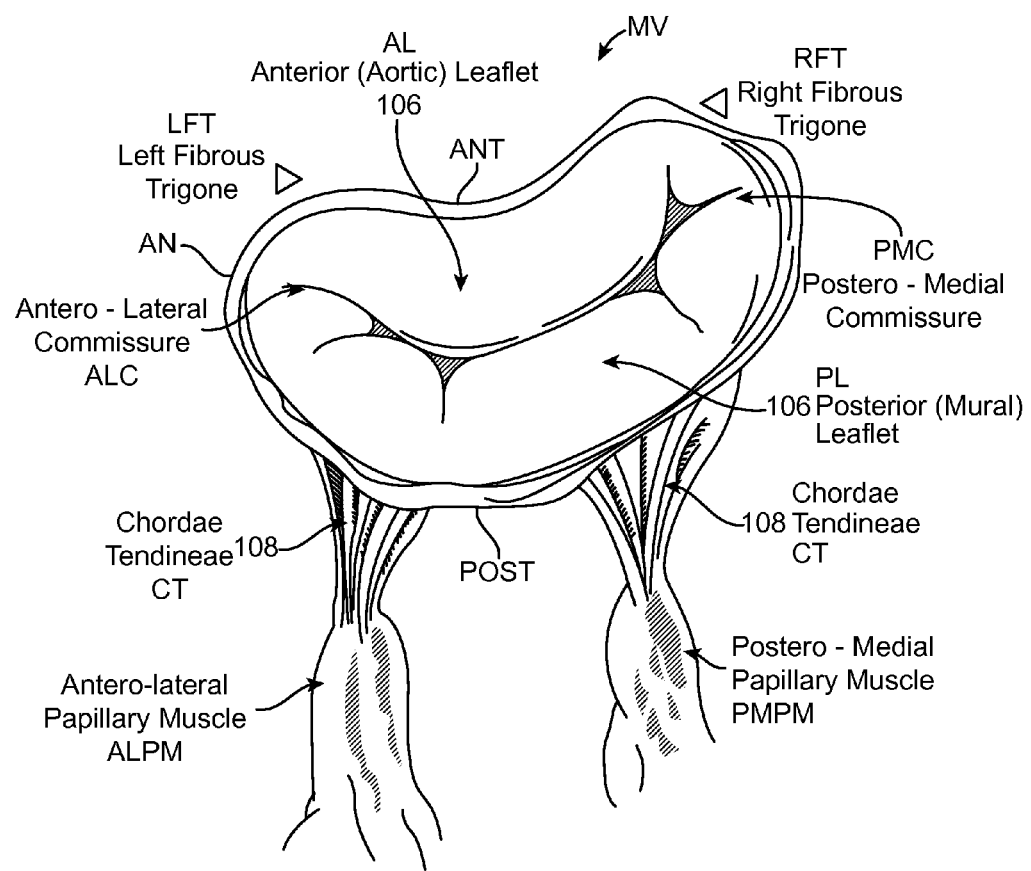
FIGS. 5A-5B illustrate anatomy of the mitral valve.
Figure 5B:
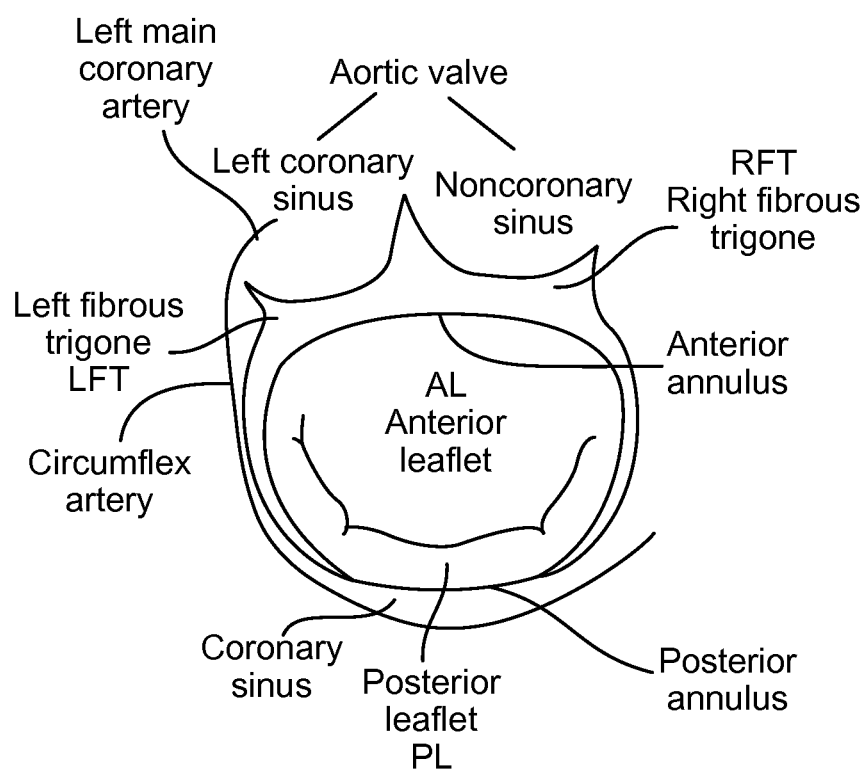

FIG. 5A more clearly illustrates the anatomy of a mitral valve MV which is a bicuspid valve having an anterior side ANT and a posterior side POST. The valve includes an anterior (aortic) leaflet AL and a posterior (mural) leaflet PL. Chordae tendineae CT couple the valve leaflets AL, PL with the antero-lateral papillary muscle ALPM and the postero-medial papillary muscle PMPM. The valve leaflets AL, PL join one another along a line referred to as the antero-lateral commissure ALC and the posterior-medial commissure PMC. The annulus AN circumscribes the valve leaflets, and two regions adjacent an anterior portion of the annulus, on opposite sides of the anterior leaflet are referred to as the left fibrous trigone LFT and also the right fibrous trigone RFT. These areas are indicted generally by the solid triangles. FIG. 5B more clearly illustrates the left and right fibrous trigones, LFT, RFT.

While various surgical techniques as well as implantable devices have been proposed and appear to be promising treatments for mitral regurgitation, surgical approaches can require a lengthy recovery period, and implantable devices have varying clinical results. Therefore, there still is a need for improved devices and methods for treating mitral regurgitation. While the embodiments disclosed herein are directed to an implantable prosthetic mitral valve for treating mitral regurgitation, one of skill in the art will appreciate that this is not intended to be limiting, and the device and methods disclosed herein may also be used to treat other cardiac valves such as the tricuspid valve, aortic valve, pulmonary valve, etc, as well as other valves in the body such as venous valves.

Prosthetic Valve. Prosthetic valves have been surgically implanted in the heart as a treatment for mitral regurgitation. Some of these valves have been valves harvested from animals such as porcine valves, and others have been prosthetic mechanical valves with or without a tissue covering. More recently, minimally invasive catheter technology has been used to deliver prosthetic valves to the heart. These valves typically include an anchor for securing the valve to the patient's heart, and a valve mechanism, either a mechanical valve, a valve with animal tissue, or combinations thereof. The prosthetic valve once implanted, takes over for the malfunctioning native valve, thereby reducing or eliminating valvar insufficiency. While some of these valves appear promising, there still is a need for improved valves. Positioning and anchoring the prosthetic valve in the native anatomy remains a challenge. The following specification discloses exemplary embodiments of a prosthetic valve, a delivery system for the prosthetic valve, and methods of delivering the valve that overcome some of the challenges associated with existing prosthetic valves.

Figure 6:
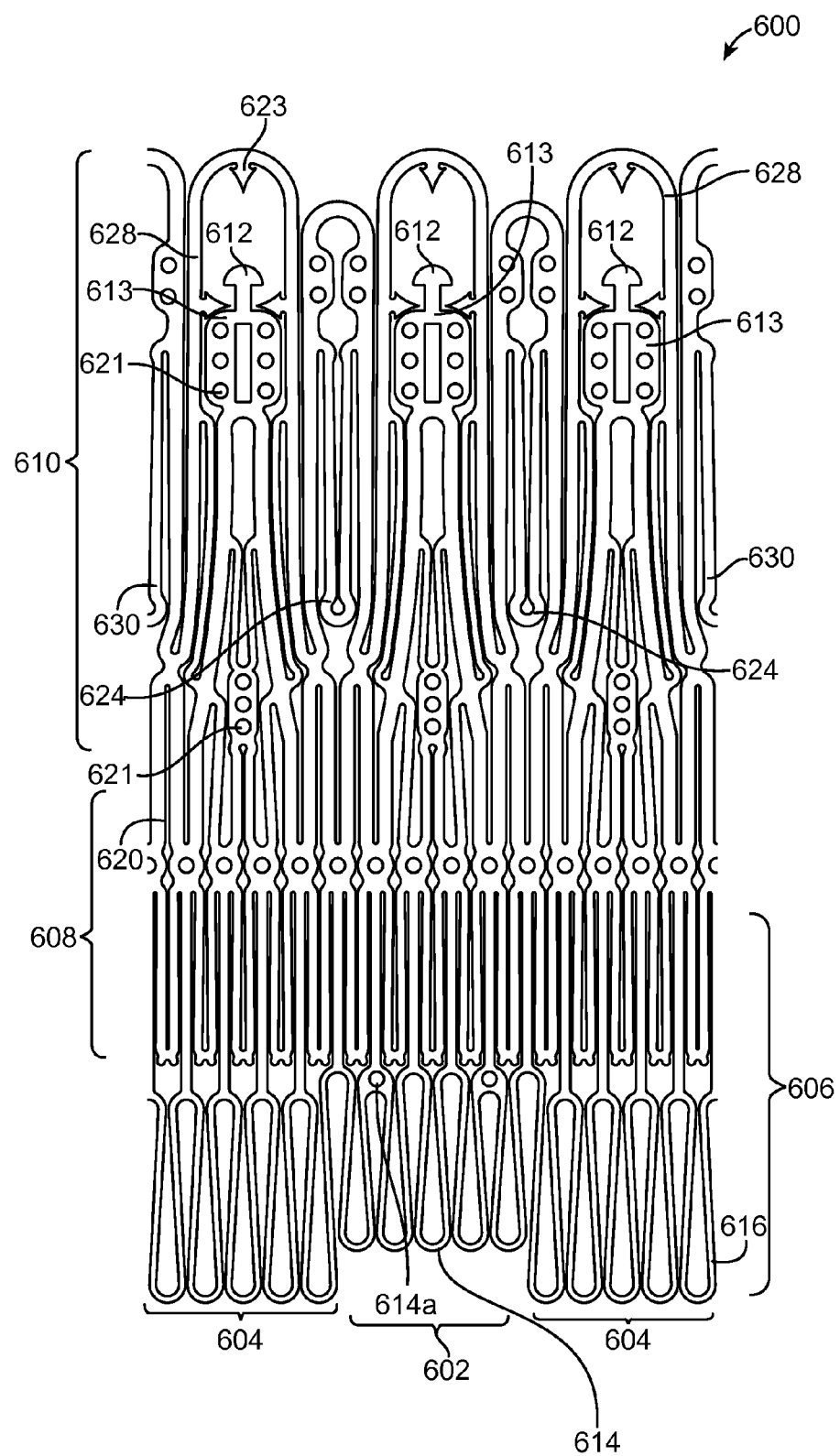
FIG. 6 illustrates an exemplary embodiment of an uncovered frame in a prosthetic cardiac valve, with the frame flattened out and unrolled.

FIG. 6 illustrates an exemplary embodiment of a prosthetic cardiac valve in the collapsed configuration. Coverings from the frame (e.g. fabric or tissue) has been removed to permit observation of the underlying frame 600. The frame has been unrolled and flattened out. The prosthetic valve frame 600 has an atrial region 606, an annular region 608, and a ventricular region 610. The frame 600 is formed from a plurality of interconnected struts that form a series of peaks and valleys which can expand and contract relative to one another thereby permitting the frame to be loaded onto a delivery catheter in a collapsed configuration, and then radially expanded at a target treatment site for implantation. Preferred embodiments are self-expanding and may be fabricated using superelastic nitinol or other self-expanding materials. Shape memory alloys that spring open above a transition temperature may also be used, and expandable members may also be used to expand the frame when plastic deformation (e.g. balloon expansion) is required to open the frame.

Atrial region 606 has a skirt 616 which includes a plurality of interconnected struts that form a series of peaks and valleys. In this region, the struts are skewed relative to one another and thus the resulting cell pattern has an enlarged end and the opposite end tapers to a smaller end. In preferred embodiments, the anterior portion of the atrial skirt does not have a flanged region like the posterior portion, thus the anterior portion 602 of the atrial region may have shorter struts than the posterior region 604. Thus the peaks and valleys in the anterior portion are axially offset from those in the remaining posterior portion of the atrial region. This may be advantageous as it prevents the struts in the anterior portion of the atrial skirt from protruding upwards potentially impinging against the left atrium and causing perforations. Additionally, the shortened struts and offset peaks and valleys form an alignment element 614 that can assist the physician with visualization of delivery of the prosthetic valve to the mitral valve and also with alignment of the prosthetic valve prior to expansion of the prosthetic valve. Optional radiopaque markers 614a are disposed on either side of the offset peaks and valleys and further help with visualization during implantation of the valve. The atrial region preferably self-expands to either a cylindrical shape, or it may have a D-shaped cross-section where the anterior portion 602 is substantially flat, and the posterior portion 604 is cylindrically shaped. This allows the atrial skirt to conform to the anatomy of the native mitral valve, thereby preventing obstruction of the left ventricular outflow tract. Additionally, the atrial skirt may also be formed so that upon expansion, the skirt flares outward and forms a flange that can rest against a superior surface of the mitral valve. The flanged region is preferably along the posterior portion of the atrial skirt, and the anterior portion of the atrial skirt remains flangeless. Or, the flange may extend entirely around the atrial skirt. The atrial region is connected to the adjacent annular region 608 with connecting struts which are preferably linear and substantially parallel to the longitudinal axis of the frame.

The annular region 608 is also comprised of a plurality of axially oriented and interconnected struts that form peaks and valleys that allow radial expansion. The struts are preferably parallel with one another and parallel with the longitudinal axis of the frame. The annular region may also be self-expanding and expand into a cylindrical shape, or more preferably the annular region may expand to have a D-shaped cross-section as described above with respect to the atrial region. Thus, the annular region may similarly have a flat anterior portion, and a cylindrically shaped posterior portion. Upon delivery, the annular region is aligned with and expanded into engagement with the mitral valve annulus. Connector struts join the annular region with the ventricular region 610.

The ventricular region 610 also includes a plurality of interconnected struts that form peaks and valleys. Additionally, the struts in the ventricular region form the leaflet commissures 613 which are covered with fabric, pericardial tissue, or other materials to form the prosthetic valve leaflets. Holes in the commissures allow suture to be attached thereto. Struts in the ventricular region also form a ventricular skirt 628 which expands outward to engage the anterior and posterior mitral valve leaflets, and struts in the ventricular region also form the anterior tabs 624 and the posterior tab 630. The anterior tabs are designed to capture the anterior mitral valve leaflet between an inner surface of the anterior tab and outer surface of the ventricular skirt. Any adjacent chordae tendineae may also be captured therebetween. Also, the tip of the anterior tab engages the fibrous trigone on an anterior portion of the mitral valve, one on the left and one on the right side. The posterior tab similarly captures the posterior mitral valve leaflet between an inner surface of the posterior tab and an outer surface of the ventricular skirt, along with any adjacent chordae tendineae. This will be described in more detail below.

By controlling strut length or axial position of the anterior or posterior tabs along the frame, deployment of the tabs may be controlled. Thus in this exemplary embodiment, because the length of the struts in the anterior tabs and posterior tabs 624, 630 as well as their relative position along the frame are the same as one another, when a constraining sheath is retracted away from the tabs, the anterior and posterior tabs will partially spring outward together. As the constraining sheath is further retracted, the remainder of the anterior tabs will self-expand radially outward. Further retraction of the constraining sheath then allows the remainder of the posterior tab to finish it's radial expansion, and finally the ventricular skirt will radially expand outward. While strut lengths and axial position of the posterior tab and the ventricular skirt are similar, internal struts connect the ventricular skirt with the commissures, and this delays expansion of the ventricular skirt slightly, thus the posterior tab finishes expansion before the ventricular skirt. Using this sequence of deploying the prosthetic valve may allow the valve to more accurately be delivered and also more securely anchored into position.

Suture holes 621 are disposed along the struts of the annular region as well as the ventricular region to allow attachment of a cover such as pericardium or a polymer such as Dacron or ePTFE. The suture holes may also be disposed along any other part of the frame. Barbs 623 are disposed along the ventricular skirt 628 to help anchor the prosthetic valve to adjacent tissue. Commissure tabs or tabs 612 are disposed on the tips of the commissures 613 and may be used to releasably couple the commissures with a delivery system as will be described below. This allows the frame to expand first, and then the commissures may be released from the delivery system afterwards. One of skill in the art will appreciate that a number of strut geometries may be used, and additionally that strut dimensions such as length, width, thickness, etc. may be adjusted in order to provide the prosthesis with the desired mechanical properties such as stiffness, radial crush strength, commissure deflection, etc. Therefore, the illustrated geometry is not intended to be limiting.

The frame may be formed by electrical discharge machining (EDM), laser cutting, photochemical etching, or other techniques known in the art. Hypodermic tubing or flat sheets may be used to form the frame. Once the frame has been cut and formed into a cylinder (if required), it may be radially expanded into a desired geometry and heat treated using known processes to set the shape. Thus, the prosthetic valve may be loaded onto a delivery catheter in a collapsed configuration and constrained in the collapsed configuration with a constraining sheath. Removal of the constraining sheath will allow the prosthesis to self-expand into its unbiased pre-set shape. In other embodiments, an expandable member such as a balloon may be used to radially expand the prosthesis into its preferred expanded configuration.

Figure 7:
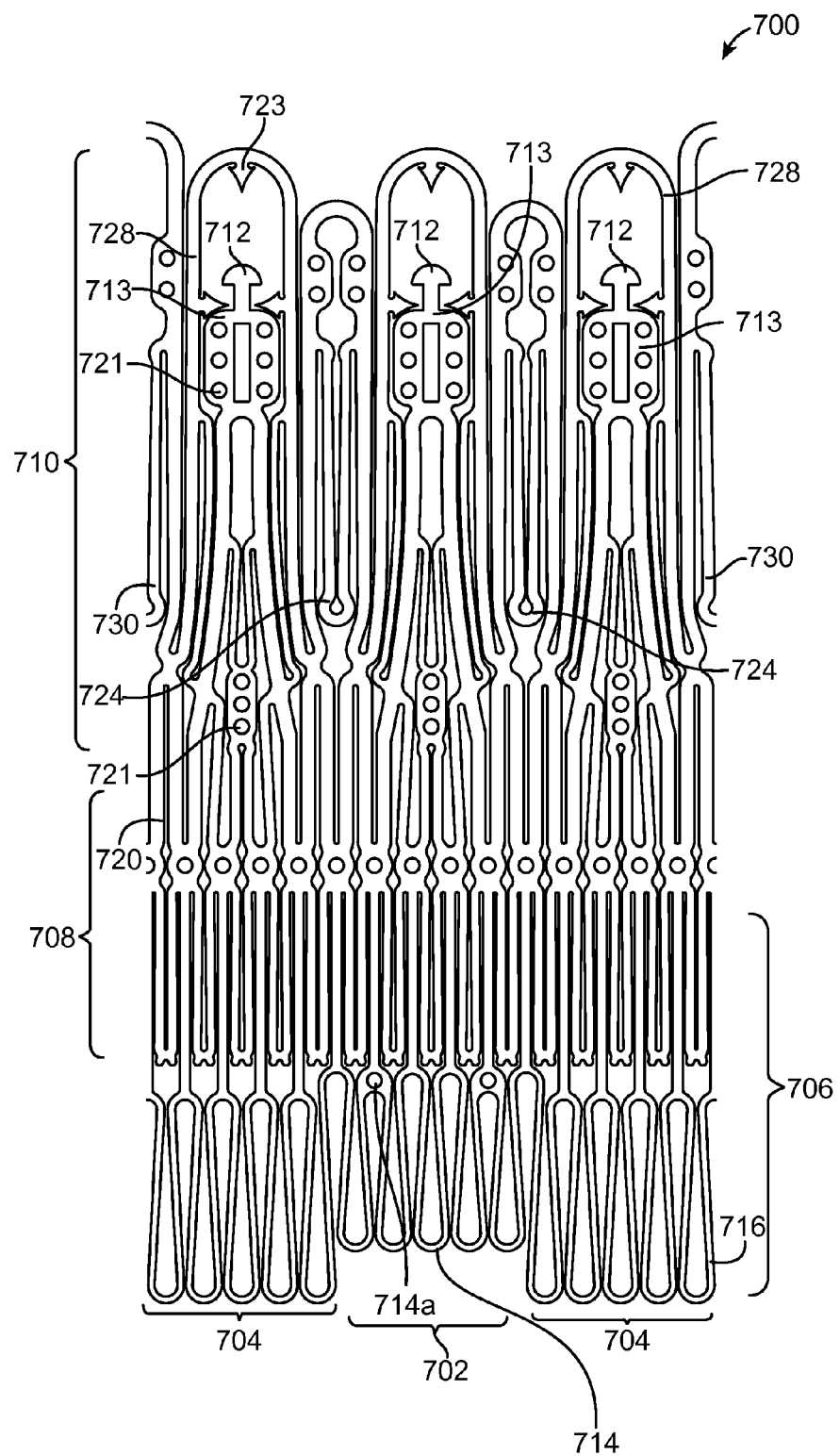
FIG. 7 illustrates another exemplary embodiment of an uncovered frame in a prosthetic cardiac valve, with the frame flattened out and unrolled.

FIG. 7 illustrates another exemplary embodiment of a prosthetic cardiac valve in the collapsed configuration, and similar to the previous embodiment with the major difference being the strut lengths in the anterior tabs, posterior tab, and ventricular skirt. Varying the strut lengths allow the sequence of expansion of the anterior and posterior tabs and ventricular skirt to be controlled. Coverings from the frame (e.g. fabric or tissue) has been removed to permit observation of the underlying frame 700. The frame has been unrolled and flattened out. The prosthetic valve frame 700 has an atrial region 706, an annular region 708, and a ventricular region 710. The frame 700 is formed from a plurality of interconnected struts that form a series of peaks and valleys which can expand and contract relative to one another thereby permitting the frame to be loaded onto a delivery catheter in a collapsed configuration, and then radially expanded at a target treatment site for implantation. Preferred embodiments are self-expanding and may be fabricated using superelastic nitinol or other self-expanding materials. Shape memory alloys that spring open above a transition temperature may also be used, and expandable members may also be used to expand the frame when plastic deformation (e.g. balloon expansion) is required to open the frame.

Atrial region 706 has a skirt 716 which includes a plurality of interconnected struts that form a series of peaks and valleys. In this region, the struts are skewed relative to one another and thus the resulting cell pattern has an enlarged end and the opposite end tapers to a smaller end. An anterior portion 702 of the atrial region has shorter struts than the posterior region 704. Thus the peaks and valleys in the anterior portion are axially offset from those in the remaining posterior portion of the atrial region. This allows creation of an alignment element 714 to help the physician deliver the prosthetic valve to the mitral valve and align the prosthetic valve prior to expansion of the prosthetic valve. Other aspects of the atrial region 706 are similar to those of the atrial region 606 in FIG. 6. Optional radiopaque markers 714a are disposed on either side of the offset peaks and valleys and help with visualization during implantation of the valve. The atrial region preferably self-expands to either a cylindrical shape, or it may have a D-shaped cross-section where the anterior portion 702 is substantially flat, and the posterior portion 704 is cylindrically shaped. This allows the atrial skirt to conform to the anatomy of the native mitral valve, thereby preventing obstruction of the left ventricular outflow tract. Additionally, the atrial skirt may also be formed so that upon expansion, the skirt flares outward and forms a flange that can rest against a superior surface of the mitral valve. The flanged region is preferably along the posterior portion of the atrial skirt, and the anterior portion of the atrial skirt remains flangeless. Or, the flange may extend entirely around the atrial skirt. The atrial region is connected to the adjacent annular region 708 with connecting struts which are preferably linear and substantially parallel to the longitudinal axis of the frame.

The annular region 708 is also comprised of a plurality of axially oriented and interconnected struts that form peaks and valleys that allow radial expansion. The struts are preferably parallel with one another and parallel with the longitudinal axis of the frame. The annular region may also be self-expanding and expand into a cylindrical shape, or more preferably the annular region may expand to have a D-shaped cross-section as described above with respect to the atrial region. Thus, the annular region may similarly have a flat anterior portion, and a cylindrically shaped posterior portion. Upon delivery, the annular region is aligned with and expanded into engagement with the mitral valve annulus. Connector struts join the annular region with the ventricular region 710.

The ventricular region 710 also includes a plurality of interconnected struts that form peaks and valleys. Additionally, the struts in the ventricular region form the leaflet commissures 713 which are covered with fabric, pericardial tissue, or other materials to form the prosthetic valve leaflets. Holes in the commissures allow suture to be attached thereto. Struts in the ventricular region also form a ventricular skirt 728 which expands outward to engage the anterior and posterior mitral valve leaflets, and struts in the ventricular region also form the anterior tabs 724 and the posterior tab 730. The anterior tabs are designed to capture the anterior mitral valve leaflet between an inner surface of the anterior tab and outer surface of the ventricular skirt. Any adjacent chordae tendineae may also be captured therebetween. Also, the tip of the anterior tab engages the fibrous trigone on an anterior portion of the mitral valve, one on the left and one on the right side. The posterior tab similar captures the posterior mitral valve leaflet between an inner surface of the posterior tab and an outer surface of the ventricular skirt, along with any adjacent chordae tendineae. This will be described in more detail below.

By controlling strut length or axial position of the anterior or posterior tabs along the frame, deployment of the tabs may be controlled. Thus in this exemplary embodiment, because the length of the struts in the anterior tabs and posterior tabs 724, 730 as well as their relative position along the frame are the same as one another, when a constraining sheath is retracted away from the tabs, the anterior and posterior tabs will partially spring outward together. As the constraining sheath is further retracted, the remainder of the anterior tabs will self-expand radially outward because they are the shortest relative to the struts in the ventricular skirt and the posterior tab. Further retraction of the constraining sheath then allows the ventricular skirt to radially expand, and finally further retraction of the sheath allows the remainder of the posterior tab to finish it's radial expansion. Using this sequence of deploying the prosthetic valve may allow the valve to more accurately be delivered and also more securely anchored into position.

Suture holes 721 are disposed along the struts of the annular region as well as the ventricular region to allow attachment of a cover such as pericardium or a polymer such as Dacron or ePTFE. The suture holes may also be disposed along any other part of the frame. Barbs 723 are disposed along the ventricular skirt 728 to help anchor the prosthetic valve to adjacent tissue. Commissure tabs or tabs 712 are disposed on the tips of the commissures 713 and may be used to releasably couple the commissures with a delivery system as will be described below. This allows the frame to expand first, and then the commissures may be released from the delivery system afterwards. One of skill in the art will appreciate that a number of strut geometries may be used, and additionally that strut dimensions such as length, width, thickness, etc. may be adjusted in order to provide the prosthesis with the desired mechanical properties such as stiffness, radial crush strength, commissure deflection, etc. Therefore, the illustrated geometry is not intended to be limiting. The frame may be formed similarly as described above with respect to FIG. 6.

Figure 8:
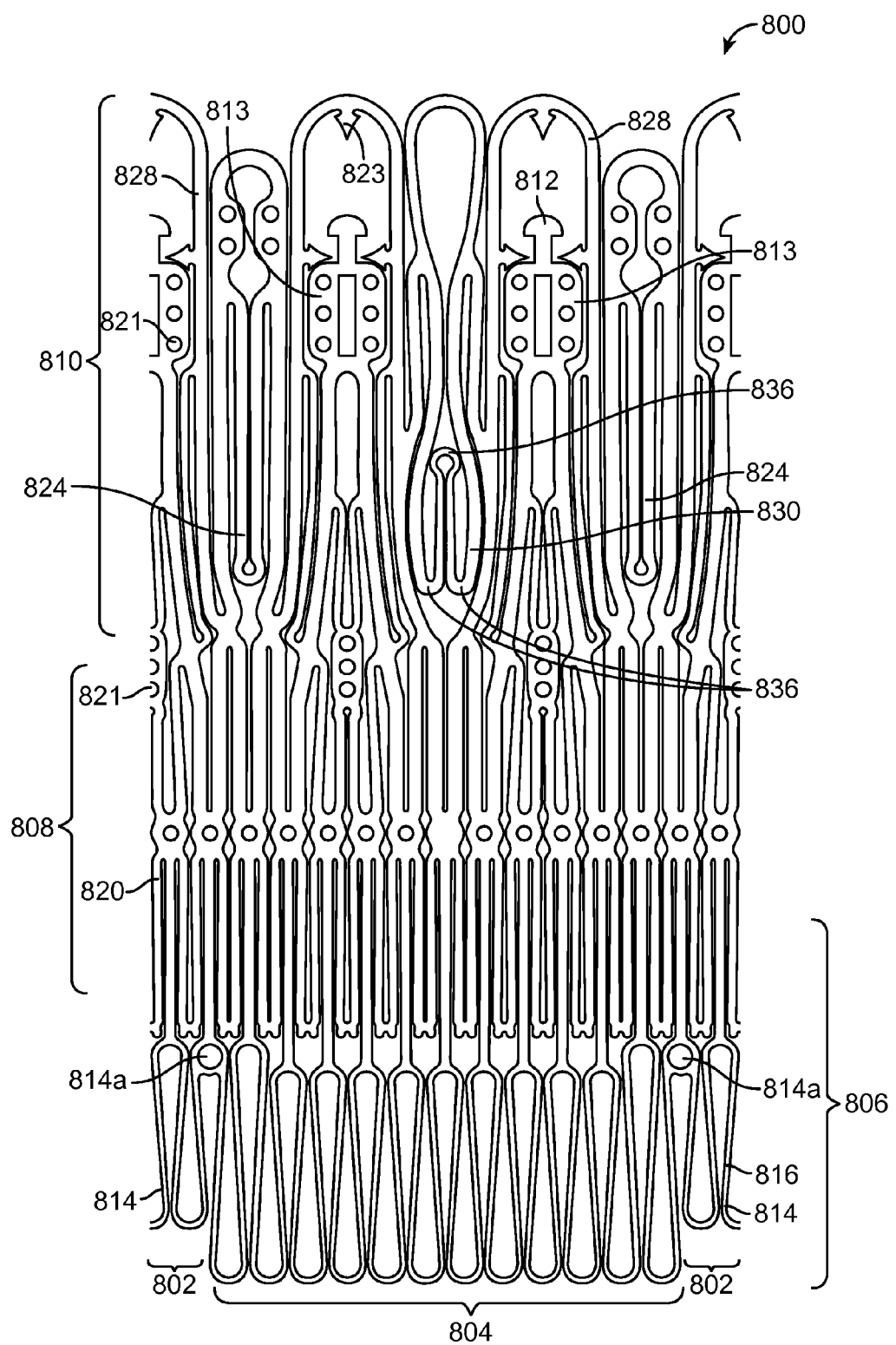
FIG. 8 illustrates still another exemplary embodiment of an uncovered frame in a prosthetic cardiac valve, with the frame flattened out and unrolled.

FIG. 8 illustrates another exemplary embodiment of a prosthetic cardiac valve in the collapsed configuration, and is similar to the previous embodiments, with the major difference being that the posterior tab is designed to expand to form an elongate horizontal section which allows engagement and anchoring of the posterior tab with the sub-annular region between the posterior leaflet and the ventricular wall. Thus, the elongate horizontal section contacts a larger region of the sub-annular region as compared with a posterior tab that only has a tapered tip formed from a single hinge between struts. This provides enhanced anchoring of the prosthetic valve. In this exemplary embodiment, the anterior tabs will completely self-expand first, followed by the posterior tab and then the ventricular skirt. However, in some situations external factors such as the delivery system, anatomy, etc. may alter the sequence of expansion, and therefore this is not intended to be limiting. Coverings from the frame (e.g. fabric or tissue) have been removed to permit observation of the underlying frame 800. The frame has been unrolled and flattened out. The prosthetic valve frame 800 has an atrial region 806, an annular region 808, and a ventricular region 810. The frame 800 is formed from a plurality of interconnected struts that form a series of peaks and valleys which can expand and contract relative to one another thereby permitting the frame to be loaded onto a delivery catheter in a collapsed configuration, and then radially expanded at a target treatment site for implantation. Preferred embodiments are self-expanding and may be fabricated using superelastic nitinol or other self-expanding materials. Shape memory alloys that spring open above a transition temperature may also be used, and expandable members may also be used to expand the frame when plastic deformation (e.g. balloon expansion) is required to open the frame.

Atrial region 806 has a skirt 816 which includes a plurality of interconnected struts that form a series of peaks and valleys. In this region, the struts are skewed relative to one another and thus the resulting cell pattern has an enlarged end and the opposite end tapers to a smaller end. An anterior portion 802 of the atrial region has shorter struts than the posterior region 804. Thus the peaks and valleys in the anterior portion are axially offset from those in the remaining posterior portion of the atrial region. This allows creation of an alignment element 814 to help the physician deliver the prosthetic valve to the mitral valve and align the prosthetic valve prior to expansion of the prosthetic valve. Other aspects of the atrial region 806 are similar to those of the atrial region 606 in FIG. 6. Optional radiopaque markers 814a are disposed on either side of the offset peaks and valleys and help with visualization during implantation of the valve. The atrial region preferably self-expands to either a cylindrical shape, or it may have a D-shaped cross-section where the anterior portion 802 is substantially flat, and the posterior portion 804 is cylindrically shaped. This allows the atrial skirt to conform to the anatomy of the native mitral valve, thereby preventing obstruction of the left ventricular outflow tract. Additionally, the atrial skirt may also be formed so that upon expansion, the skirt flares outward and forms a flange that can rest against a superior surface of the mitral valve. The flanged region is preferably along the posterior portion of the atrial skirt, and the anterior portion of the atrial skirt remains flangeless. Or, the flange may extend entirely around the atrial skirt. The atrial region is connected to the adjacent annular region 808 with connecting struts which are preferably linear and substantially parallel to the longitudinal axis of the frame.

The annular region 808 is also comprised of a plurality of axially oriented and interconnected struts that form peaks and valleys that allow radial expansion. The struts are preferably parallel with one another and parallel with the longitudinal axis of the frame. The annular region may also be self-expanding and expand into a cylindrical shape, or more preferably the annular region may expand to have a D-shaped cross-section as described above with respect to the atrial region. Thus, the annular region may similarly have a flat anterior portion, and a cylindrically shaped posterior portion. Upon delivery, the annular region is aligned with and expanded into engagement with the mitral valve annulus. Connector struts join the annular region with the ventricular region 810.

The ventricular region 810 also includes a plurality of interconnected struts that form peaks and valleys. Additionally, the struts in the ventricular region form the leaflet commissures 813 which are covered with fabric, pericardial tissue, or other materials to form the prosthetic valve leaflets. Holes in the commissures allow suture to be attached thereto. Struts in the ventricular region also form a ventricular skirt 828 which expands outward to engage the anterior and posterior mitral valve leaflets, and struts in the ventricular region also form the anterior tabs 824 and the posterior tab 830. The anterior tabs are designed to capture the anterior mitral valve leaflet between an inner surface of the anterior tab and outer surface of the ventricular skirt. Any adjacent chordae tendineae may also be captured therebetween. Also, the tip of the anterior tab engages the fibrous trigone on an anterior portion of the mitral valve, one on the left and one on the right side. The posterior tab similarly captures the posterior mitral valve leaflet between an inner surface of the posterior tab and an outer surface of the ventricular skirt, along with any adjacent chordae tendineae. This will be described in more detail below. The posterior tab is similar to the posterior tabs described above in FIGS. 6-7, except that in this embodiment, the posterior tab comprises four interconnected struts as opposed to two interconnected struts. Thus, in this embodiment the plurality of interconnected struts form three hinged regions 836 along the tab. Upon expansion of the posterior tab, the hinged regions will also expand, thereby forming an elongate horizontal section which allows engagement and anchoring of the posterior tab with the sub-annular region between the posterior leaflet and the ventricular wall. This may help position and anchor the prosthetic valve better than posterior tabs which only have a smaller footprint or a single tapered tip for engagement with the posterior portion of the mitral valve. The posterior tab in this embodiment, may be substituted with any of the other posterior tabs described in this specification.

By controlling strut length or axial position of the anterior or posterior tabs along the frame, deployment of the tabs may be controlled. Thus in this exemplary embodiment, because the length of the struts in the anterior tabs and posterior tabs 824, 830 as well as their relative position along the frame are the same as one another, when a constraining sheath is retracted away from the tabs, the anterior and posterior tabs will partially spring outward together. As the constraining sheath is further retracted, the remainder of the anterior tabs will self-expand radially outward because they are the shortest relative to the struts in the ventricular skirt and the posterior tab. Further retraction of the constraining sheath then allows the remainder of the posterior tab to finish self-expanding, followed by self-expansion of the ventricular skirt. Using this sequence of deploying the prosthetic valve may allow the valve to more accurately be delivered and also more securely anchored into position.

Suture holes 821 are disposed along the struts of the annular region as well as the ventricular region to allow attachment of a cover such as pericardium or a polymer such as Dacron or ePTFE. The suture holes may also be disposed along any other part of the frame. Barbs 823 are disposed along the ventricular skirt 828 to help anchor the prosthetic valve to adjacent tissue. Commissure tabs or tabs 812 are disposed on the tips of the commissures 813 and may be used to releasably couple the commissures with a delivery system as will be described below. This allows the frame to expand first, and then the commissures may be released from the delivery system afterwards. One of skill in the art will appreciate that a number of strut geometries may be used, and additionally strut dimensions such as length, width, thickness, etc. may be adjusted in order to provide the prosthesis with the desired mechanical properties such as stiffness, radial crush strength, commissure deflection, etc. Therefore, the illustrated geometry is not intended to be limiting. The frame may be formed similarly as described above.

Figure 9A:
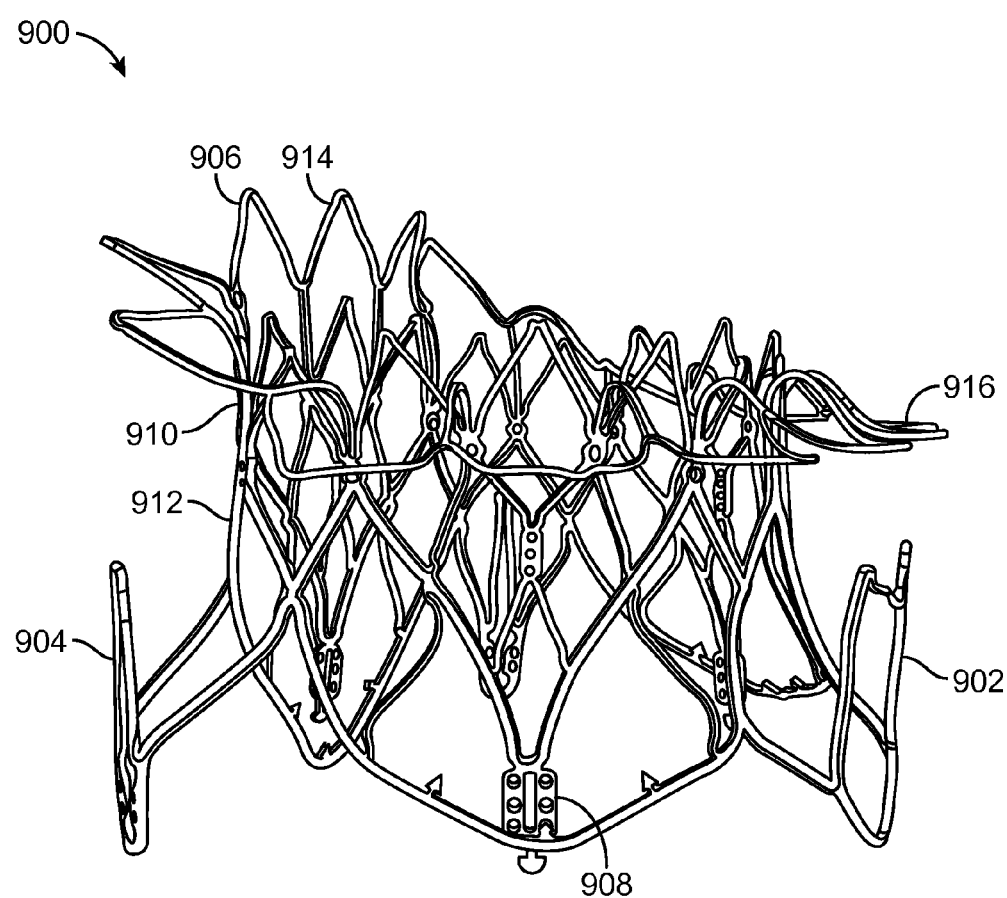
FIG. 9A illustrates a perspective view of an uncovered frame in a prosthetic cardiac valve after it has expanded.
Figure 9B:
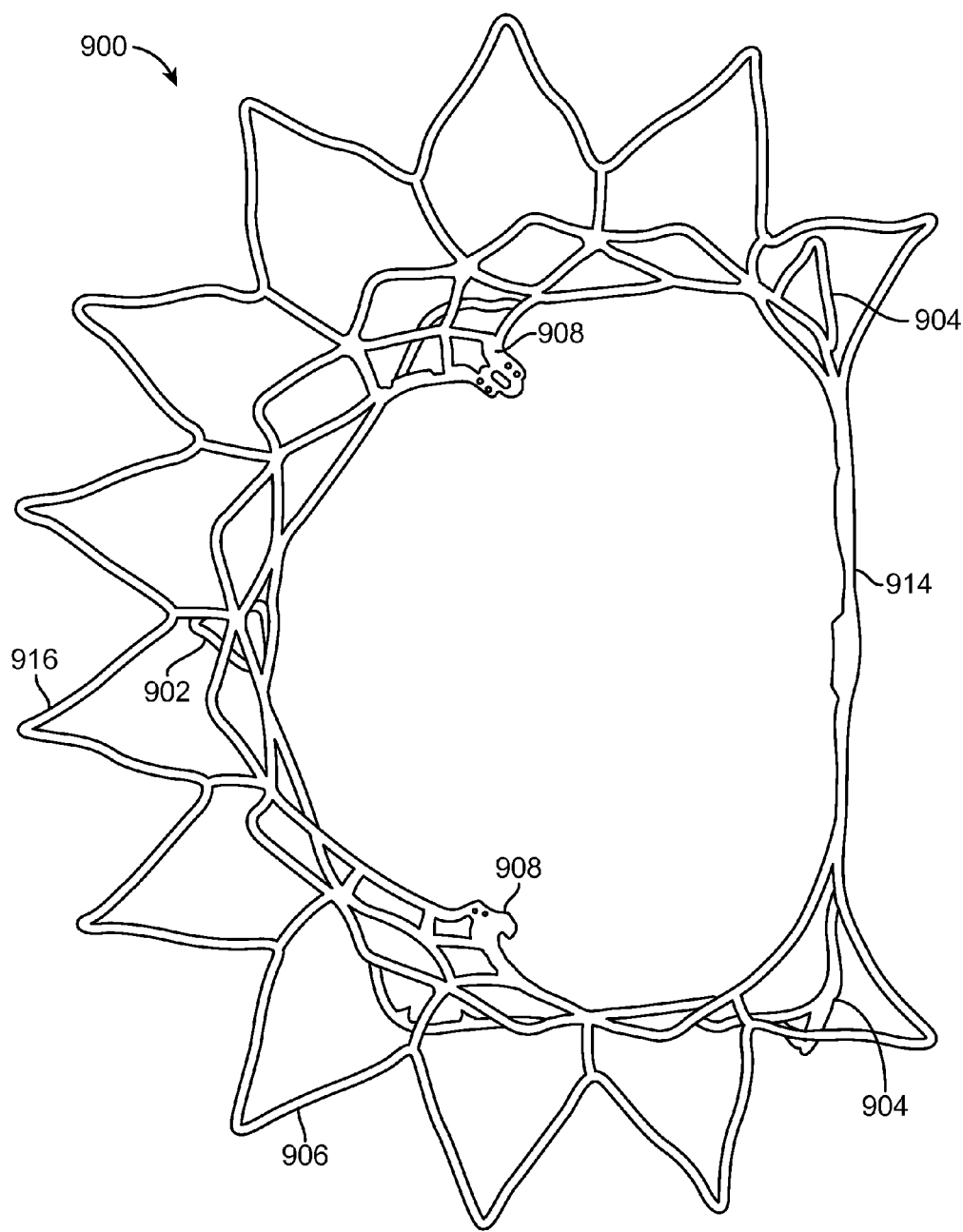
FIG. 9B illustrates a top view of the embodiment in FIG. 9A.

FIG. 9A illustrates the frame 900 of a prosthetic cardiac valve after it has expanded. Any of the frame embodiments described above may take this form as each of the above frames have similar geometry but they expand in different order. The frame includes the atrial skirt 906 with anterior portion 914 and posterior portion 916. A flanged region is formed around the posterior portion and the anterior portion remains flangeless. Additionally, the anterior portion is generally flat, while the posterior portion is cylindrically shaped, thereby forming a D-shaped cross-section which accommodates the mitral valve anatomy. FIG. 9B is a top view of the embodiment in FIG. 9A and more clearly illustrates the D-shaped cross-section.

The frame also includes the annular region 910 and ventricular skirt 912. Anterior tabs 904 (only one visible in this view) is fully expanded such that a space exists between the inner surface of the anterior tab and an outer surface of the ventricular skirt. This allows the anterior leaflet and adjacent chordae to be captured therebetween. Similarly, the posterior tab 902 is also fully deployed, with a similar space between the inner surface of the posterior tab 902 and an outer surface of the ventricular skirt. This allows the posterior leaflet and adjacent chordae tendineae to be captured therebetween. The commissure posts 908 are also visible and are disposed in the inner channel formed by the frame. The commissure posts are used to form the prosthetic mitral valve leaflets. The overall shape of the expanded frame is D-shaped, with the anterior portion flat and the posterior portion cylindrically shaped.

Figure 10:
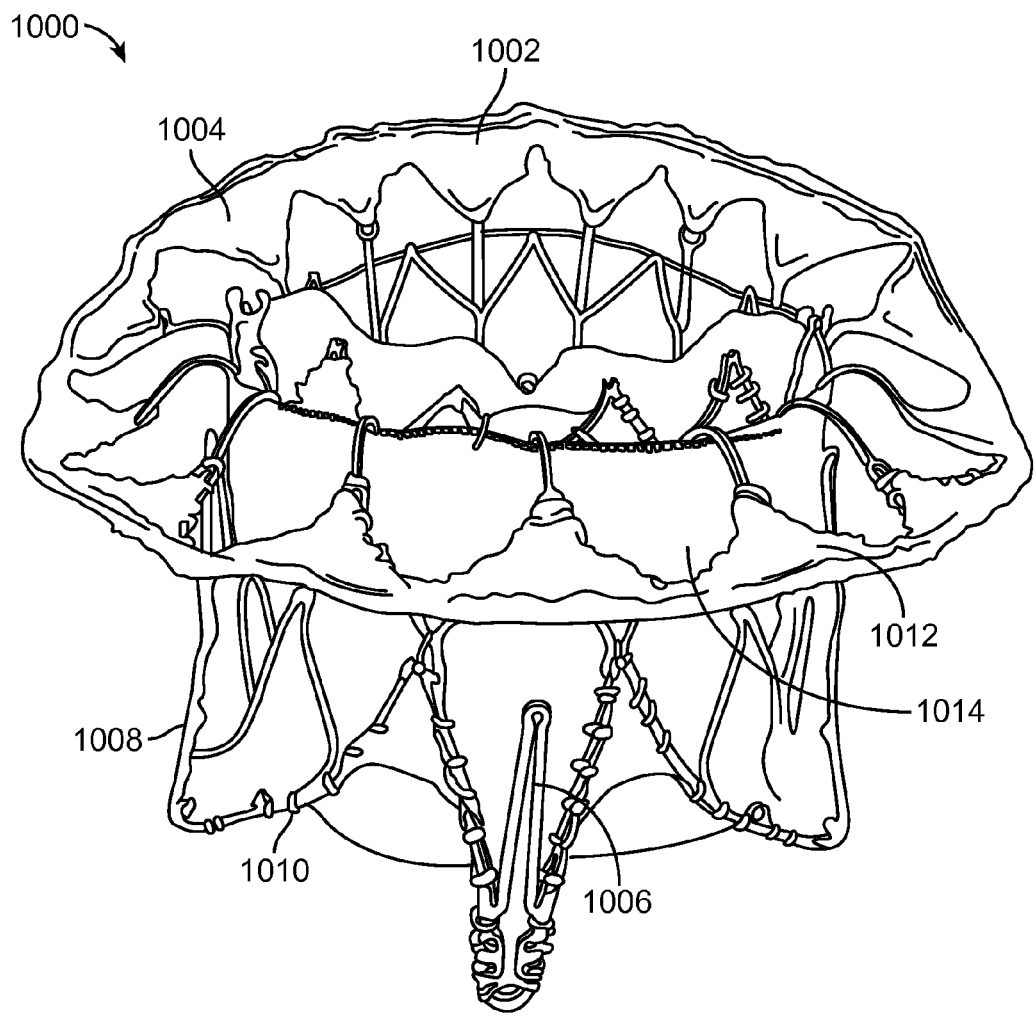
FIG. 10 illustrates the frame of FIG. 9A with the covering thereby forming a prosthetic cardiac valve.

FIG. 10 illustrates the expanded frame covered with a cover 1002 such as pericardial tissue or a polymer such as ePTFE or a fabric like Dacron attached to the frame, thereby forming the prosthetic cardiac valve 1000. The atrial skirt may be entirely covered by a material, or in preferred embodiments, the covering is only disposed between adjacent struts 1012 in adjacent cells in the flanged portion of the atrial skirt. The area 1014 between adjacent struts within the same cell remain uncovered. This allows blood flow to remain substantially uninterrupted while the prosthetic valve is being implanted. Suture 1010 may be used to attach the cover to the frame. In this view, only the posterior tab 1006 is visible on the posterior portion of the prosthetic valve along with ventricular skirt 1008 and atrial skirt 1004.

Delivery System. FIGS. 11A-11D illustrate an exemplary embodiment of a delivery system that may be used to deliver any of the prosthetic cardiac valves disclosed in this specification. While the delivery system is designed to preferably deliver the prosthetic cardiac valve transapically, one of skill in the art will appreciate that it may also be modified so that the prosthetic valve may be delivered via a catheter transluminally, such using a transseptal route. One of skill in the art will appreciate that using a transseptal route may require the relative motion of the various shafts to be modified in order to accommodate the position of the delivery system relative to the mitral valve.

Figure 11A:
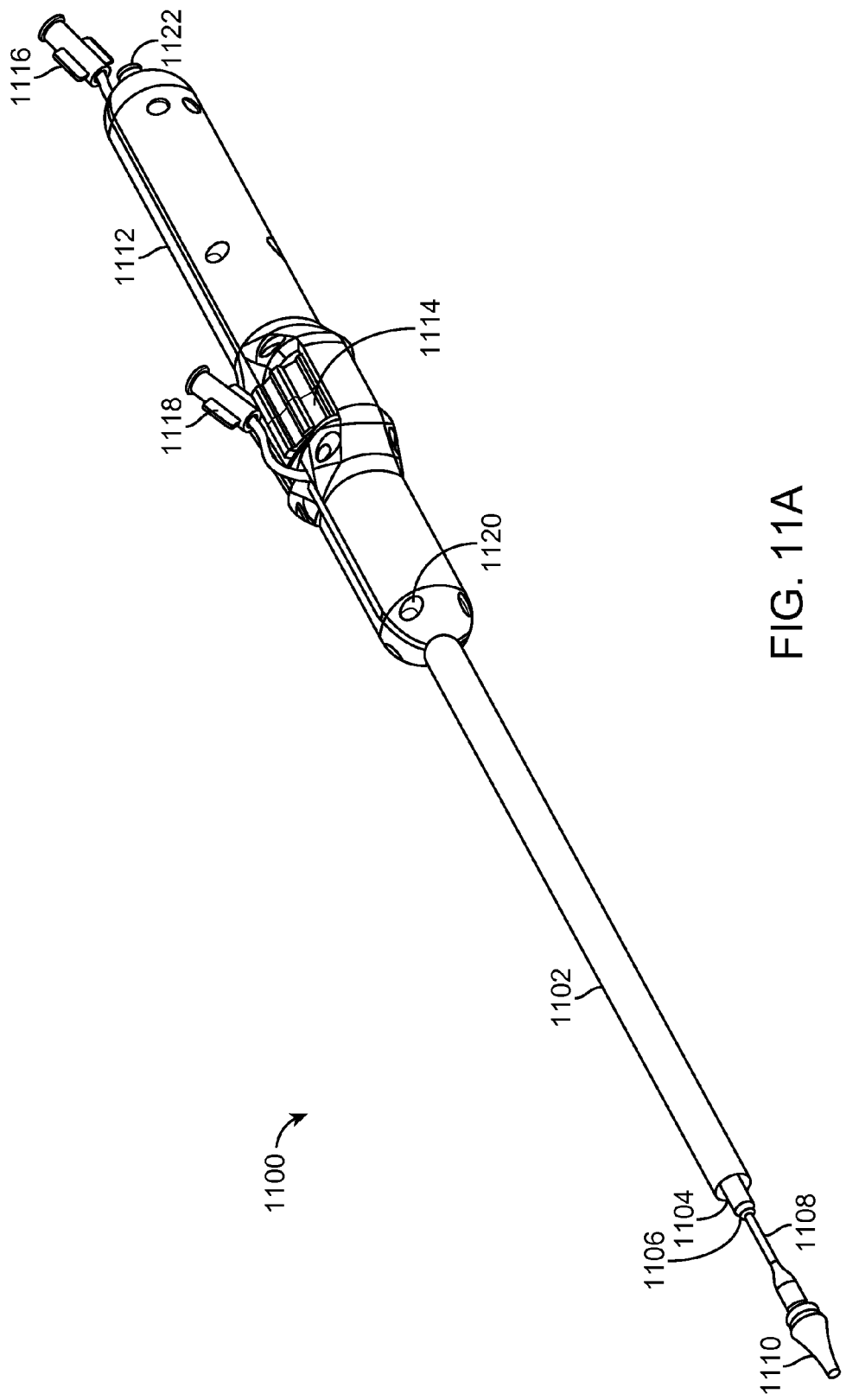
FIGS. 11A-11D illustrate an exemplary embodiment of a delivery system used to transapically deliver a prosthetic cardiac valve.
Figure 11B:
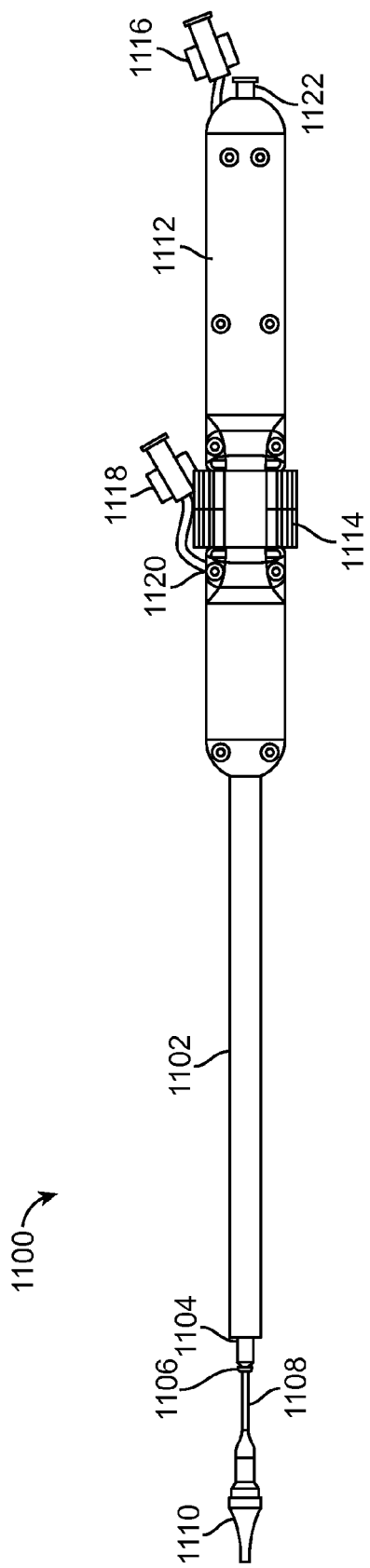

FIG. 11A illustrates a perspective view of delivery system 1100. The delivery system 1100 includes a handle 1112 near a proximal end of the delivery system and a distal tissue penetrating tip 1110. Four elongate shafts are included in the delivery system and include an outer sheath catheter shaft 1102, a bell catheter shaft 1104 which is slidably disposed in the outer sheath catheter shaft 1102, a hub catheter shaft 1106 which remains stationary relative to the other shafts, but the bell catheter shaft slides relative to the hub shaft, and finally an inner guidewire catheter shaft 1108 which is also fixed relative to the other shafts and has a lumen sized to receive a guidewire which passes therethrough and exits the distal tissue penetrating tip. An actuator mechanism 1114 is used to control movement of the various shafts as will be explained in greater detail below, and flush lines 1116, 1118 with luer connectors are used to flush the annular regions between adjacent shafts. Flush line 1118 is used to flush the annular space between the outer sheath catheter shaft 1102 and the bell catheter shaft 1104. Flush line 1116 is used to flush the annular space between the bell catheter 1104 and the hub catheter 1106. The inner guidewire catheter shaft 1108 is stationary relative to the hub catheter 1106 therefore the annular space may be sealed with an o-ring or other material. Luer connector 1122 allows flushing of the guidewire lumen and a hemostatic valve such as a Tuohy-Borst may be coupled to the luer connector to allow a guidewire to be advanced through the guidewire catheter shaft while maintaining hemostasis. Screws 1120 keep the handle housing coupled together. FIG. 11B illustrates a side view of the delivery system 1100.

Figure 11C:
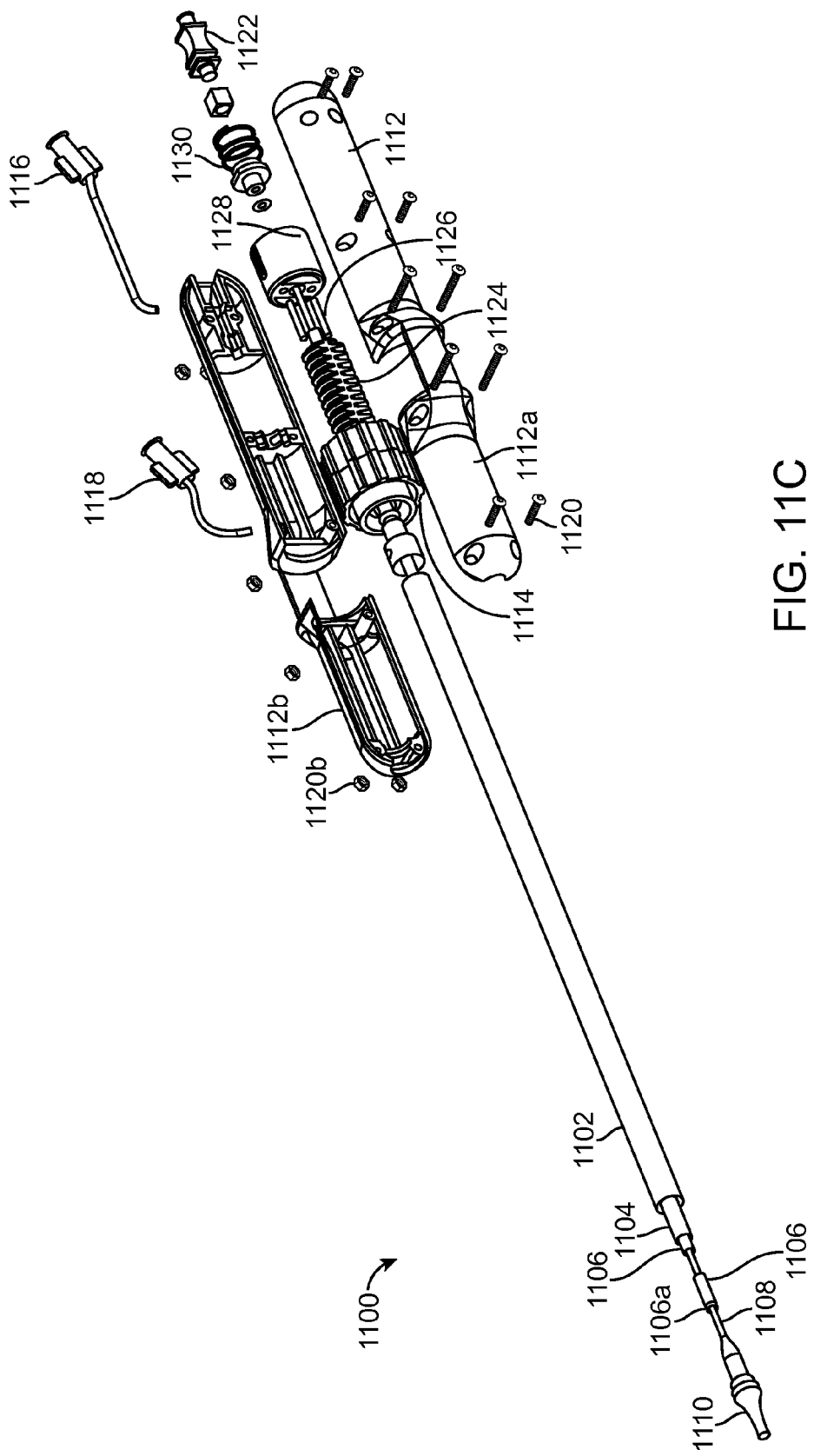

FIG. 11C is a partial exploded view of the delivery system 1100 and more clearly illustrates the components in the handle 1112 and how they interact. The handle 1112 includes a housing having two halves 1112a, 1112b which hold all the components. The handle is preferably held together with screws 1120 and nuts 1120b, although it may also be sealed using other techniques such as a press fit, snap fit, adhesive bonding, ultrasonic welding, etc. Rotation of actuator wheel 1114 is translated into linear motion of threaded insert 1124. The outer sheath catheter shaft 1102 is coupled to the threaded insert 1124, therefore rotation of actuator wheel 1114 in one direction will advance the sheath catheter shaft 1102, and rotation in the opposite direction will retract the sheath catheter shaft 1102. Further rotation of actuator wheel 1114 retracts threaded insert 1124 enough to bump into pins 1126 which are coupled to insert 1128, thereby also moving insert 1128. The bell catheter shaft 1106 is coupled to insert 1128, therefore further rotation of the actuator wheel 1114 will move the outer shaft 1102 and also move the bell catheter shaft 1106. Rotation of the actuator wheel in the opposite direction advances the sheath and threaded insert 1124 disengages from pins 1126. Spring 1130 returns insert 1128 to its unbiased position, thereby returning the bell catheter shaft to its unbiased position.

Any of the prosthetic cardiac valves disclosed herein may be carried by delivery system 1100. The atrial skirt, annular skirt, anterior tabs, posterior tab and ventricular skirt are loaded over the bell catheter shaft and disposed under the outer sheath catheter shaft 1102. The ventricular skirt is loaded proximally so that it is closest to the handle 1112 and the atrial skirt is loaded most distally so it is closest to the tip 1110. Therefore, retraction of outer sheath catheter shaft 1102 plays a significant part in controlling deployment of the prosthetic cardiac valve. The atrial skirt therefore expands first when the outer sheath catheter is retracted. The prosthetic valve commissures may be coupled with a hub 1106a on the distal portion of hub catheter 1106 and then the bell catheter shaft is disposed thereover, thereby releasably engaging the commissures with the delivery catheter. Once other portions of the prosthetic cardiac valve have expanded, the commissures may be released.

Figure 11D:
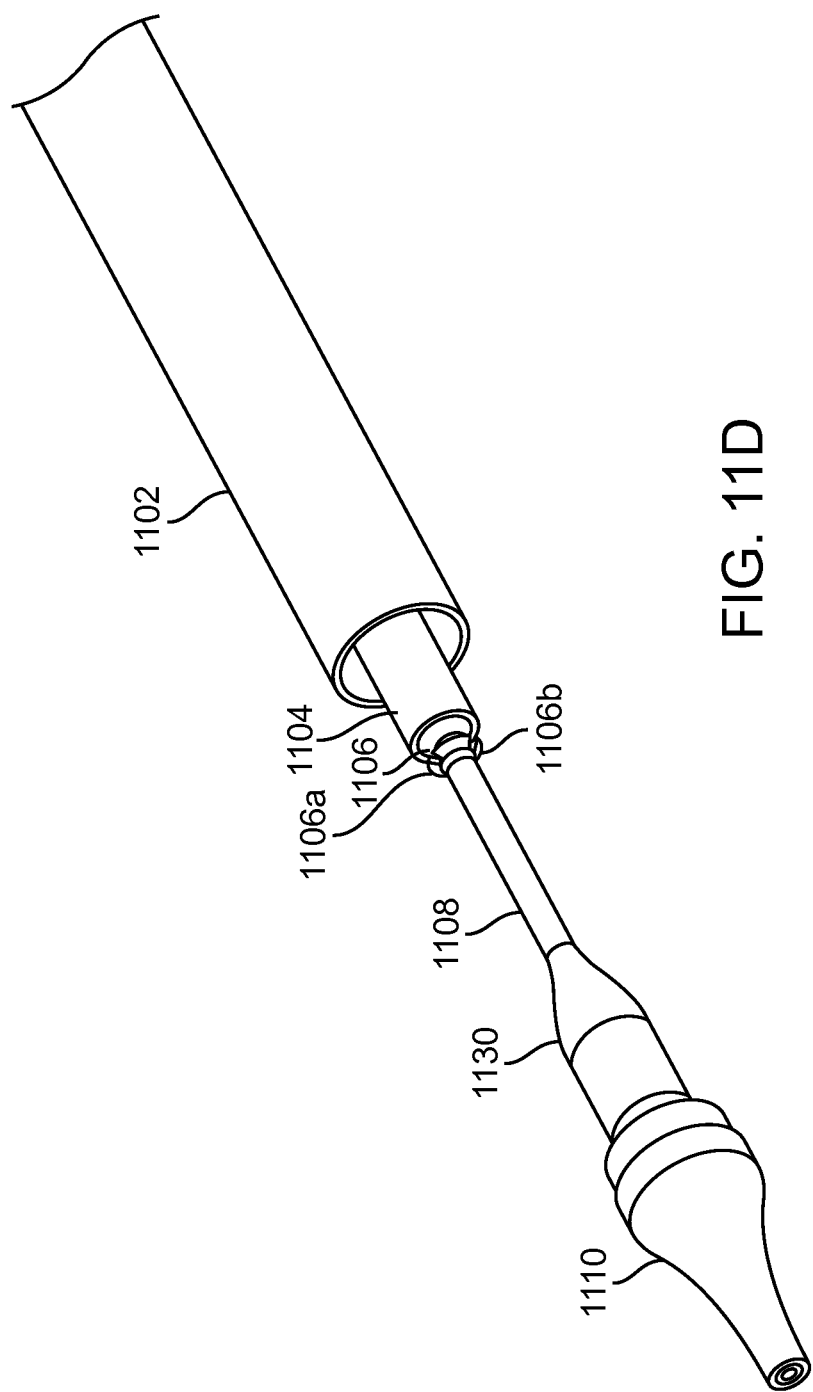

FIG. 11D highlights the distal portion of the delivery system 1100. Outer sheath catheter shaft 1102 advances and retracts relative to bell catheter shaft 1104 which is slidably disposed in the outer sheath catheter shaft 1102. Hub catheter shaft 1106 is shown slidably disposed in bell catheter shaft 1104 and with bell catheter shaft 1104 retracted so as to expose the hub 1106a having slots 1106b that hold the prosthetic valve commissures. Inner guidewire catheter shaft 1108 is the innermost shaft and has a tapered conical section 1130 which provides a smooth transition for the prosthetic valve and prevents unwanted bending or buckling of the prosthetic cardiac valve frame. Tissue penetrating tip 1110 is adapted to penetrate tissue, especially in a cardiac transapical procedure.

Delivery Method. A number of methods may be used to deliver a prosthetic cardiac valve to the heart. Exemplary methods of delivering a prosthetic mitral valve may include a transluminal delivery route which may also be a transseptal technique which crosses the septum between the right and left sides of the heart, or in more preferred embodiments, a transapical route may be used such as illustrated in FIGS. 12A-12L. The delivery device previously described above may be used to deliver any of the embodiments of prosthetic valves described herein, or other delivery devices and other prosthetic valves may also be used, such as those disclosed in U.S. patent application Ser. No. 13/096,572, previously incorporated herein by reference. However, in this preferred exemplary embodiment, the prosthetic cardiac valve of FIG. 6 is used so that the anterior tabs deploy first, followed by the posterior tab, and then the ventricular skirt.

Figure 12A:
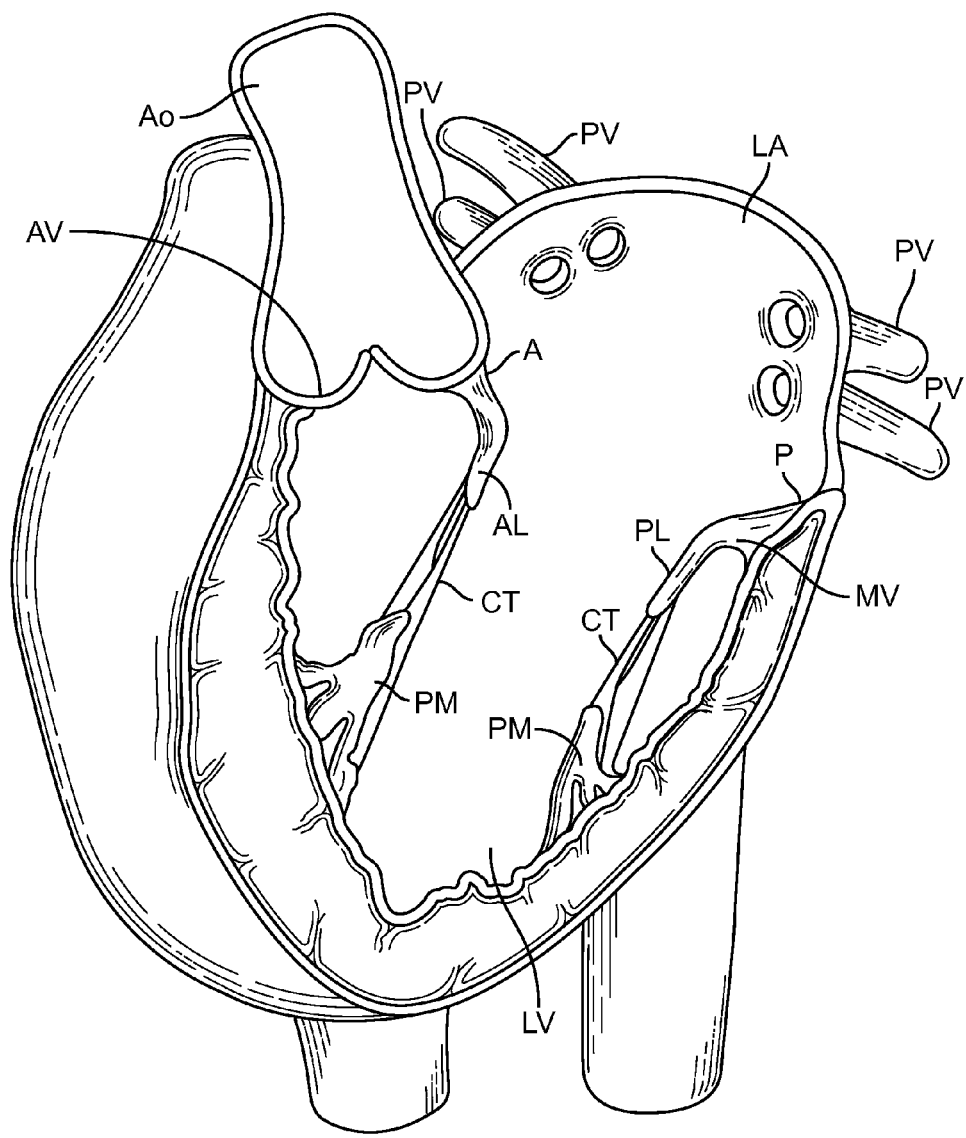
FIGS. 12A-12L illustrate an exemplary method of implanting a prosthetic cardiac valve.

FIG. 12A illustrates the basic anatomy of the left side of a patient's heart including the left atrium LA and left ventricle LV. Pulmonary veins PV return blood from the lungs to the left atrium and the blood is then pumped from the left atrium into the left ventricle across the mitral valve MV. The mitral valve includes an anterior leaflet AL on an anterior side A of the valve and a posterior leaflet PL on a posterior side P of the valve. The leaflets are attached to chordae tendineae CT which are subsequently secured to the heart walls with papillary muscles PM. The blood is then pumped out of the left ventricle into the aorta Ao with the aortic valve AV preventing regurgitation.

Figure 12B:
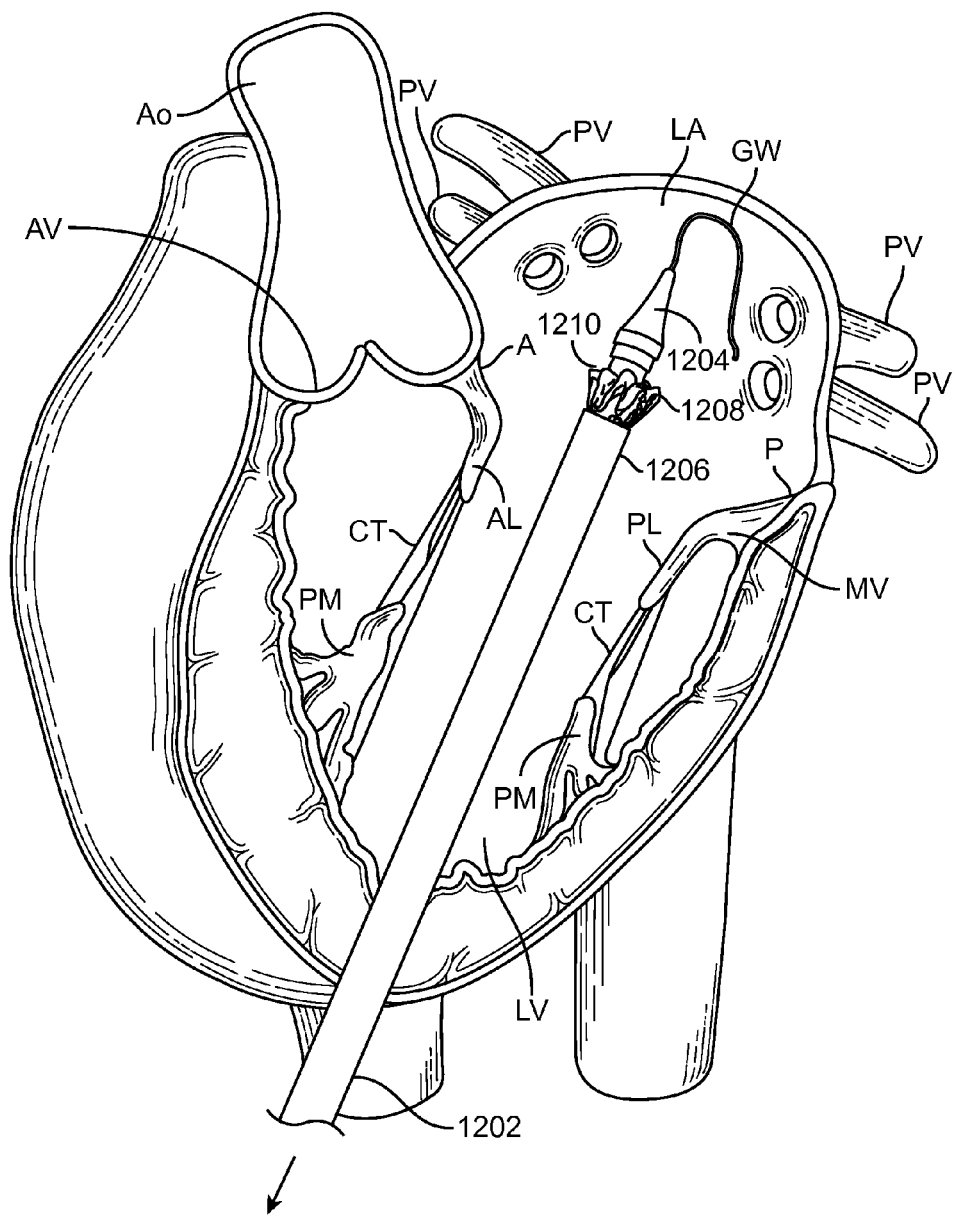
Figure 12C:
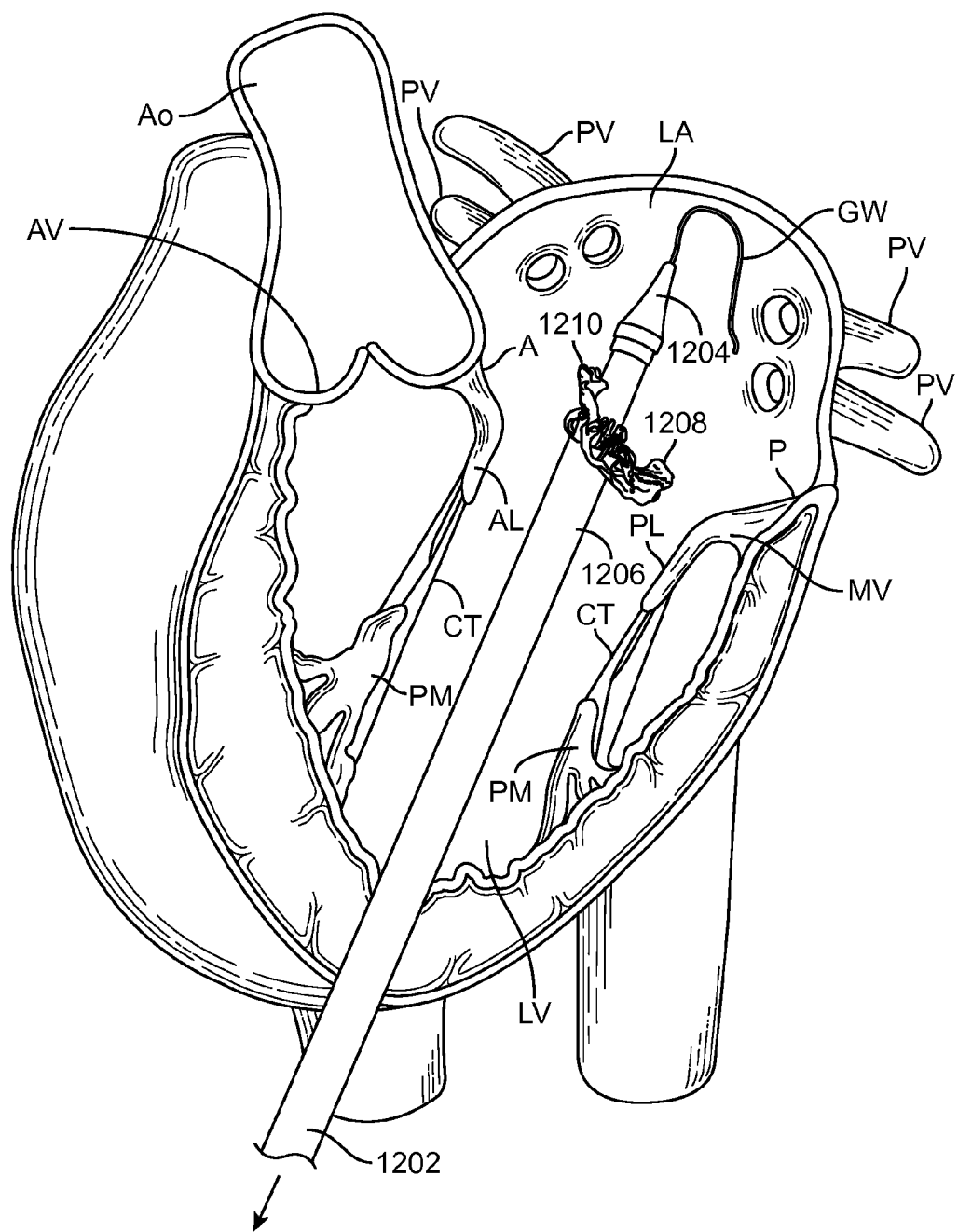
Figure 12D:
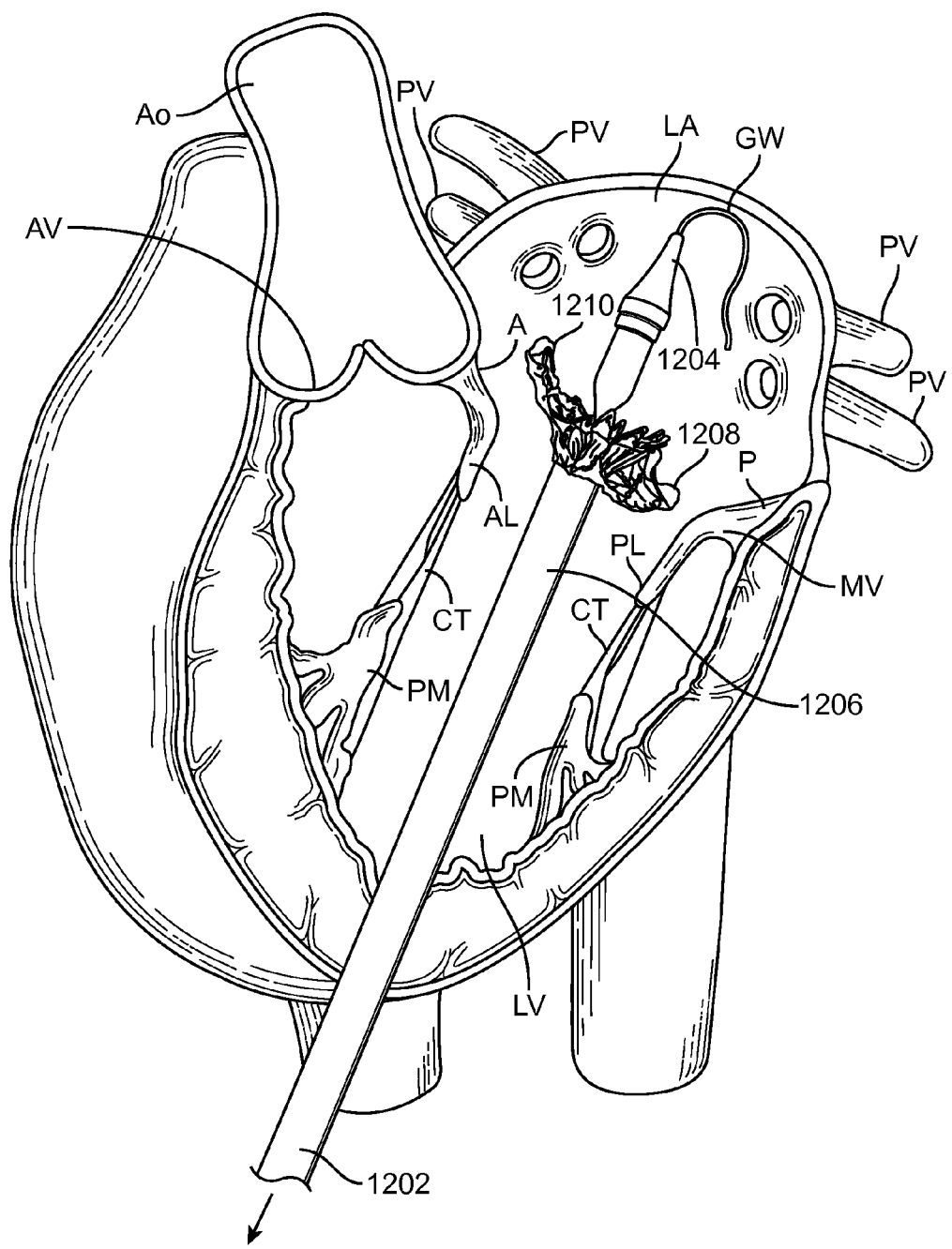

FIG. 12B illustrates transapical delivery of a delivery system 1202 through the apex of the heart into the left atrium LA via the left ventricle LV. The delivery system 1202 may be advanced over a guidewire GW into the left atrium, and a tissue penetrating tip 1204 helps the delivery system pass through the apex of the heart by dilating the tissue and forming a larger channel for the remainder of the delivery system to pass through. The delivery catheter carries prosthetic cardiac valve 1208. Once the distal portion of the delivery system has been advanced into the left atrium, the outer sheath 1206 may be retracted proximally (e.g. toward the operator) thereby removing the constraint from the atrial portion of the prosthetic valve 1208. This allows the atrial skirt 1210 to self-expand radially outward. In FIG. 12C, as the outer sheath is further retracted, the atrial skirt continues to self-expand and peek out, until it fully deploys as seen in FIG. 12D. The atrial skirt may have a cylindrical shape or it may be D-shaped as discussed above with a flat anterior portion and a cylindrical posterior portion so as to avoid interfering with the aortic valve and other aspects of the left ventricular outflow tract. The prosthesis may be oriented and properly positioned by rotating the prosthesis and visualizing the alignment element previously described. Also, the prosthetic cardiac valve may be advanced upstream or downstream to properly position the atrial skirt. In preferred embodiments, the atrial skirt forms a flange that rests against a superior surface of the mitral valve and this anchors the prosthetic valve and prevents it from unwanted movement downstream into the left ventricle.

Figure 12E:
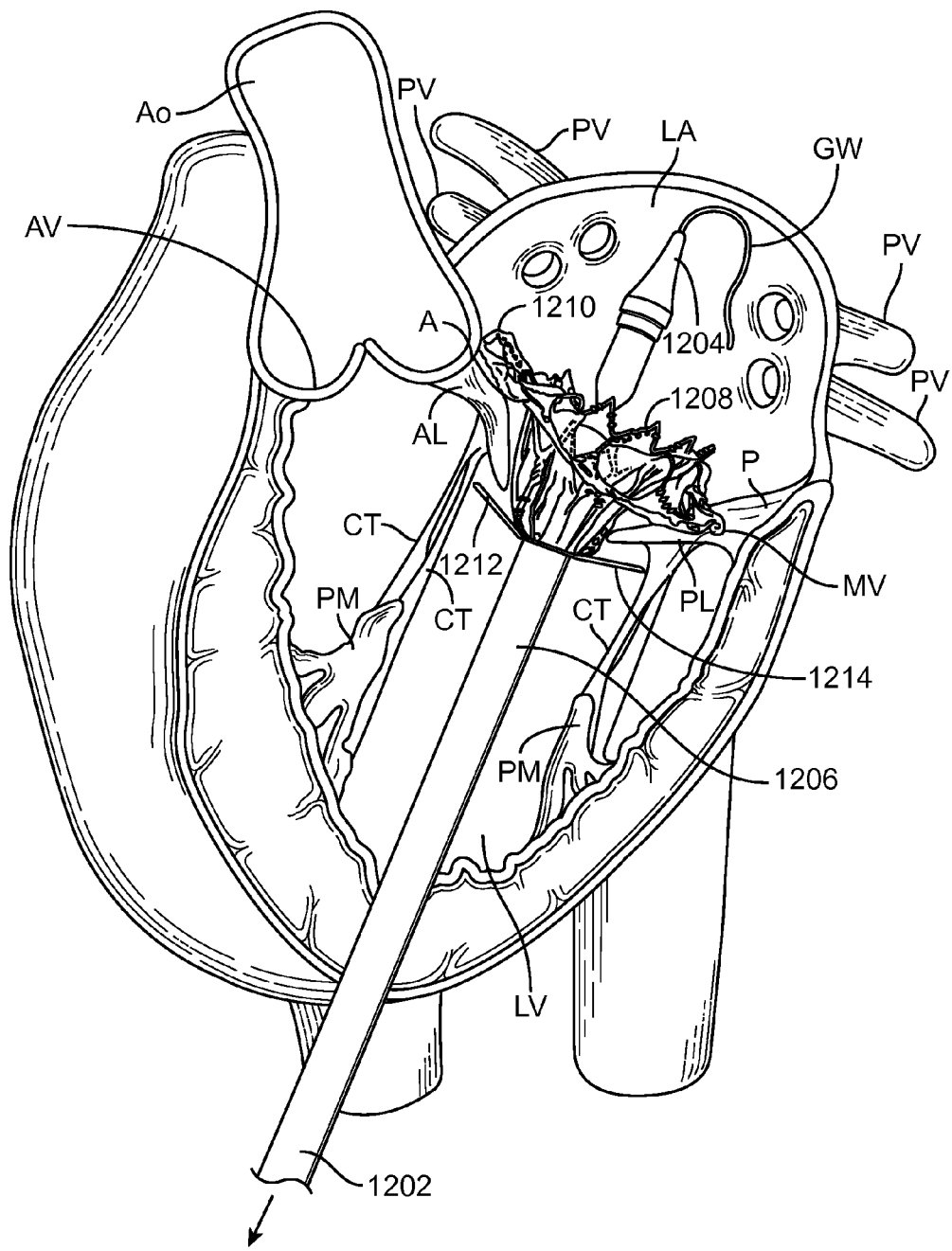
Figure 12F:
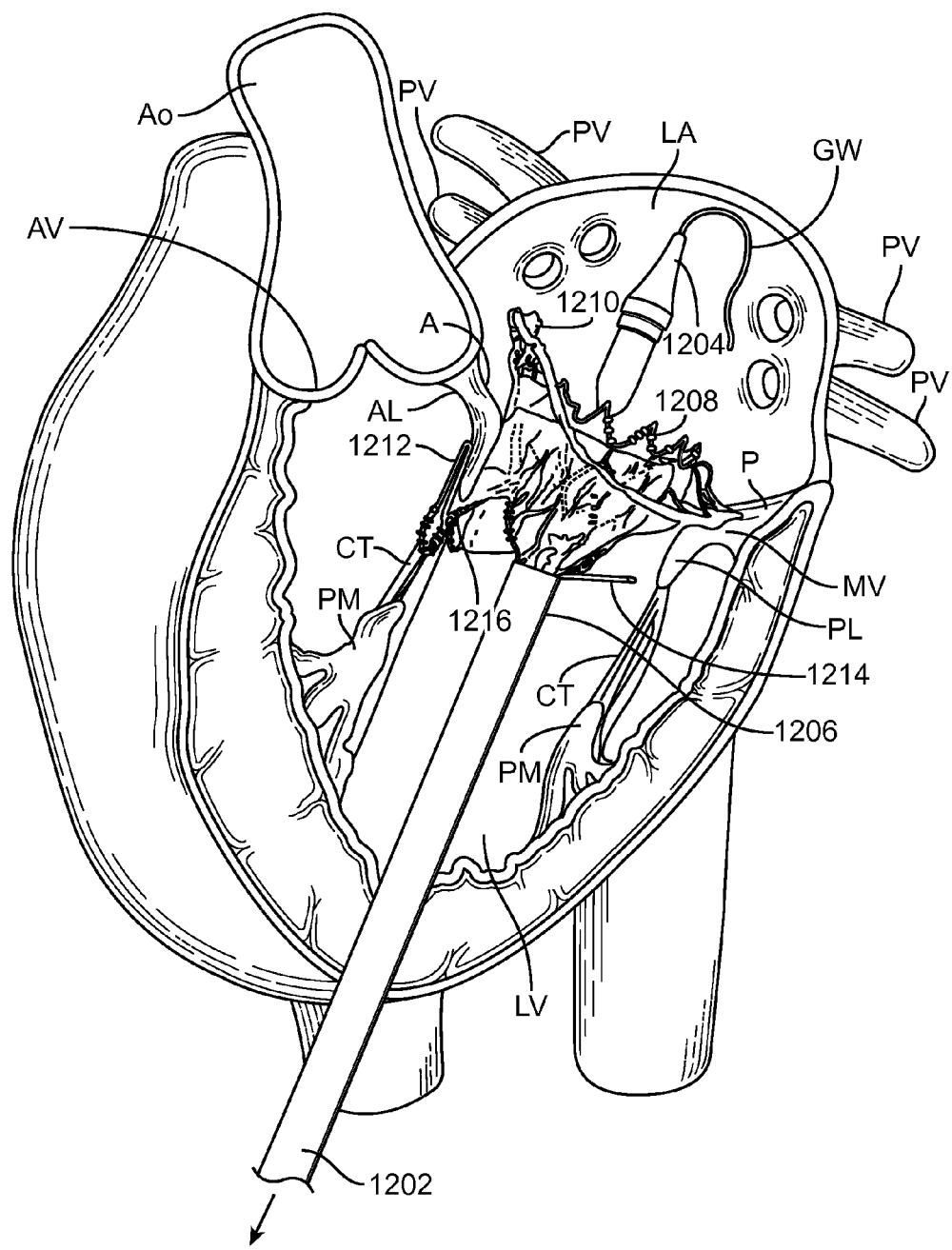

As the outer sheath 1206 continues to be proximally retracted, the annular region of the prosthetic cardiac valve self-expands next into engagement with the valve annulus. The annular region also preferably has the D-shaped geometry, although it may also be cylindrical or have other geometries to match the native anatomy. In FIG. 12E, retraction of sheath 1206 eventually allows both the anterior 1212 and posterior 1214 tabs to partially self-expand outward preferably without engaging the anterior or posterior leaflets or the chordae tendineae. In this embodiment, further retraction of the outer sheath 1206 then allows both the anterior tabs 1212 (only one visible in this view) to complete their self-expansion so that the anterior leaflet is captured between an inner surface of each of the anterior tabs and an outer surface of the ventricular skirt 1216, as illustrated in FIG. 12F. The posterior tab 1214 remains partially open, but has not completed its expansion yet. Additionally, the tips of the anterior tabs also anchor into the left and right fibrous trigones of the mitral valve, as will be illustrated in greater detail below.

Figure 12G:
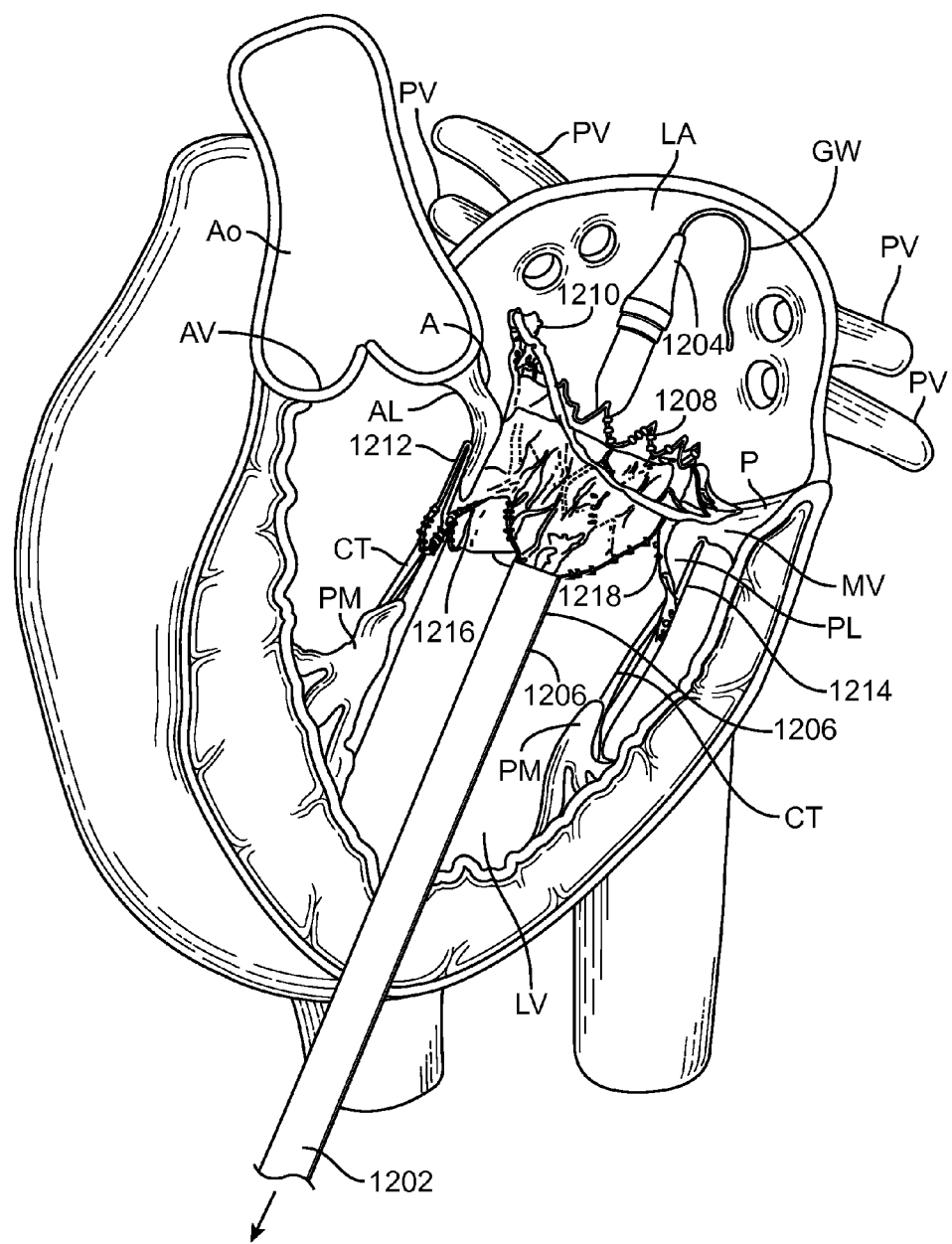
Figure 12H:
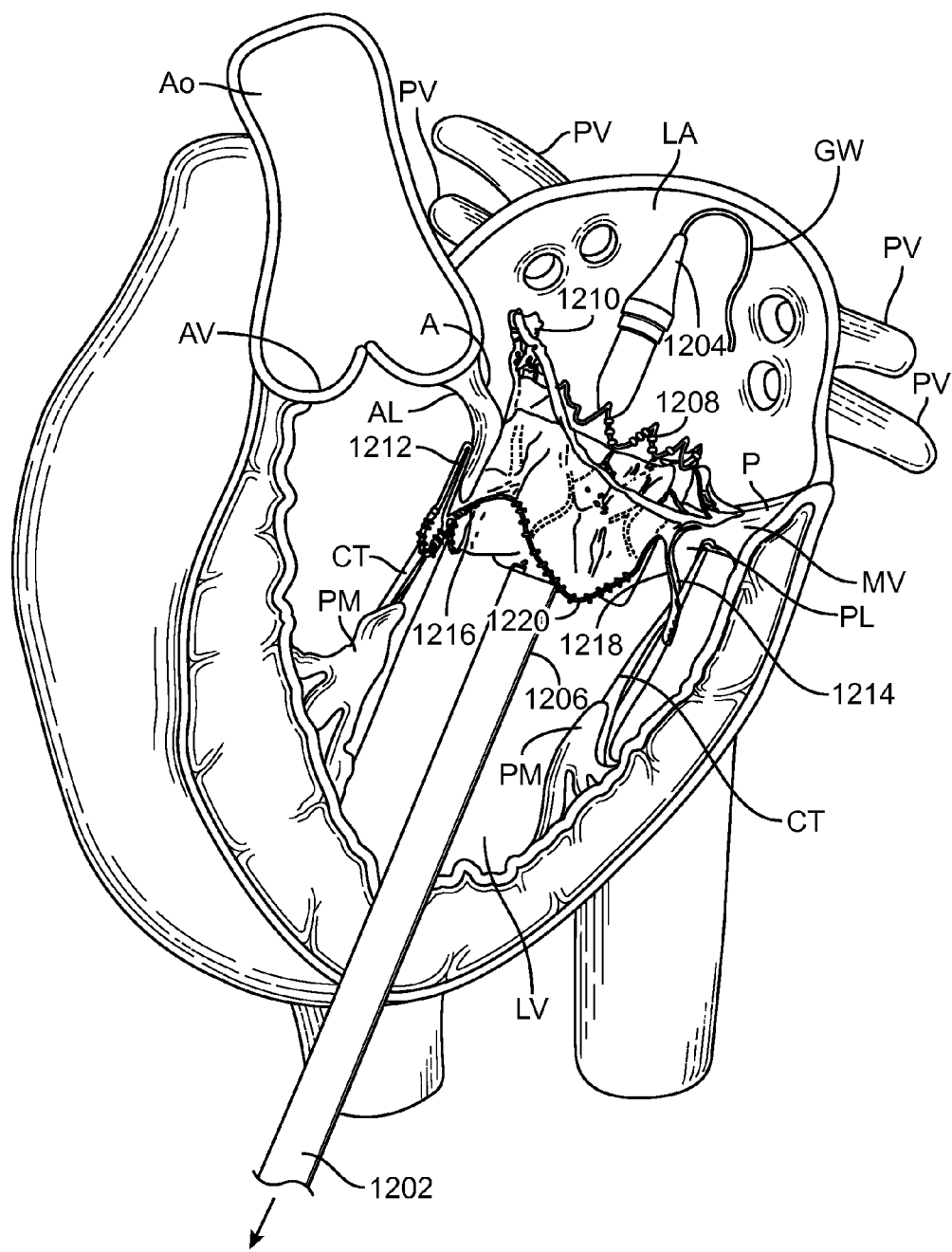

In FIG. 12G, further retraction of the outer sheath 1206 then releases the constraints from the posterior tab 1214 allowing it to complete its self-expansion, thereby capturing the posterior leaflet PL between an inner surface of the posterior tab 1214 and an outer surface of the ventricular skirt 1218. In FIG. 12H, the sheath is retracted further releasing the ventricular skirt 1220 and allowing the ventricular skirt 1220 to radially expand outward, further capturing the anterior and posterior leaflets between the outer surface of the ventricular skirt and their respective anterior or posterior tabs. Expansion of the ventricular skirt also pushes the anterior and posterior leaflets outward, thereby ensuring that the native leaflets do not interfere with any portion of the prosthetic valve or the prosthetic valve leaflets. The prosthetic valve is now anchored in position above the mitral valve, along the annulus, to the valve leaflets, and below the mitral valve, thereby securing it in position.

Figure 12I:
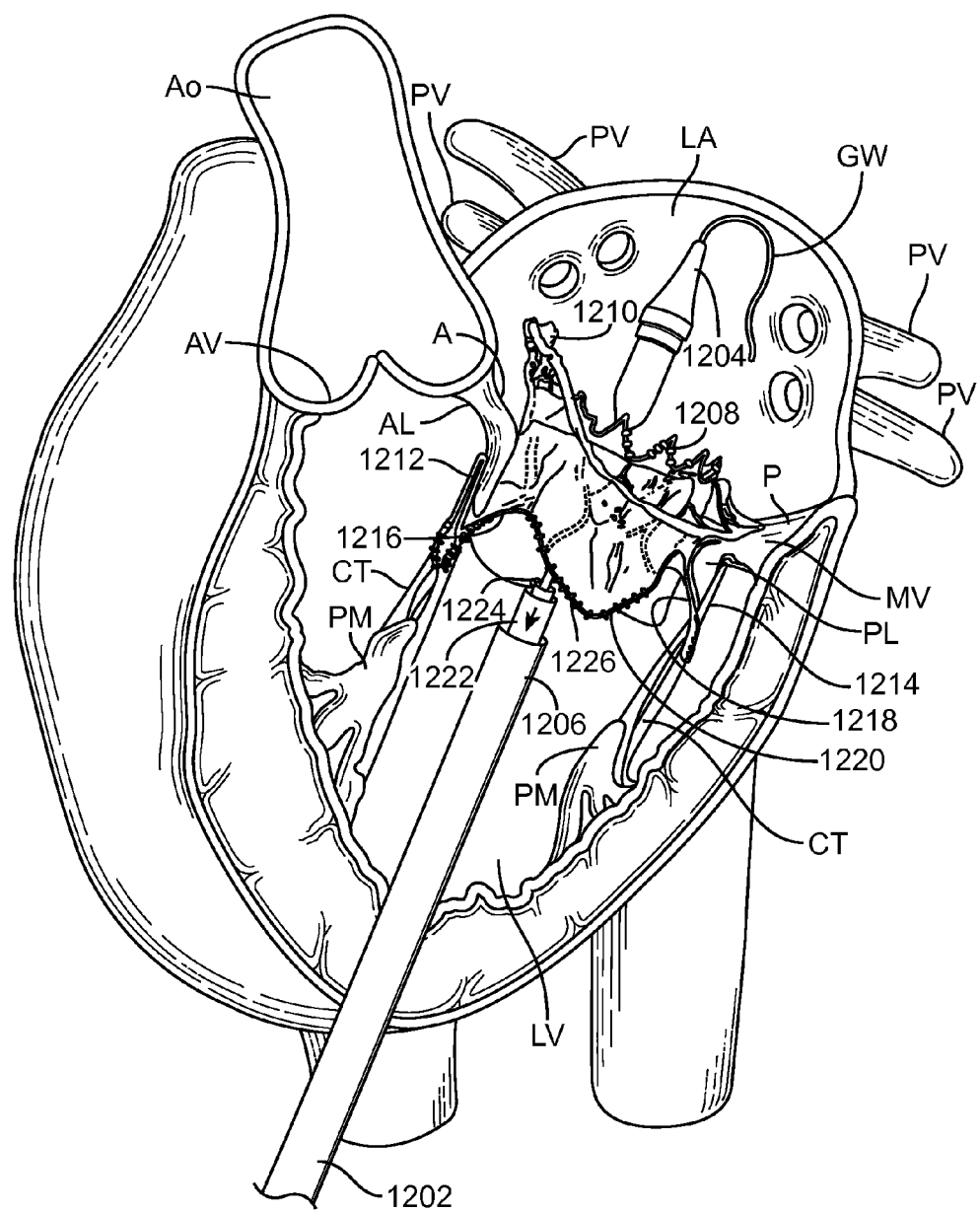
Figure 12J:
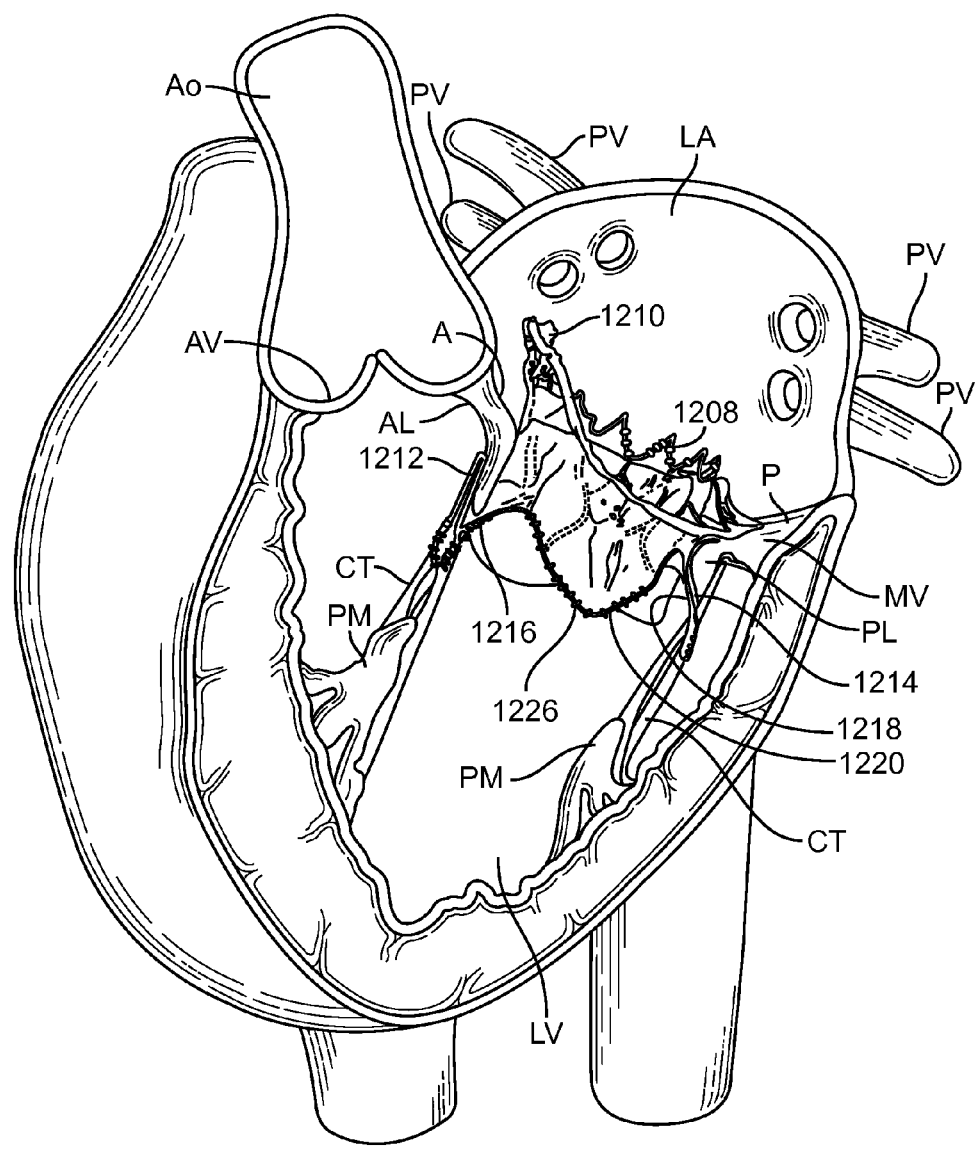

Further actuation of the delivery device now retracts the outer sheath 1206 and the bell catheter shaft 1222 so as to remove the constraint from the hub catheter 1224, as illustrated in FIG. 12I. This permits the prosthetic valve commissures 1226 to be released from the hub catheter, thus the commissures expand to their biased configuration. The delivery system 1202 and guidewire GW are then removed, leaving the prosthetic valve 1208 in position where it takes over for the native mitral valve, as seen in FIG. 12J.

Figure 12K:
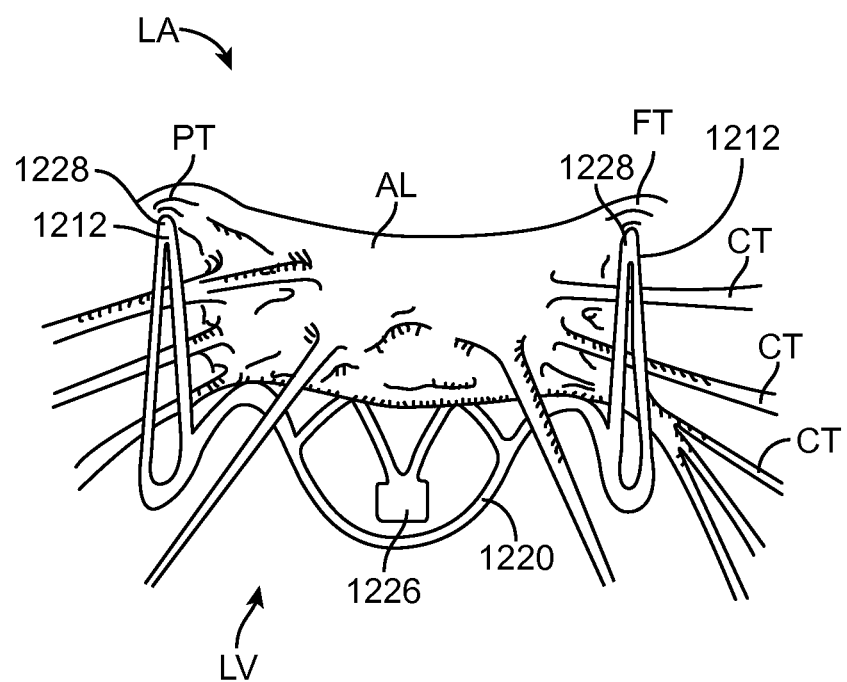
Figure 12L:
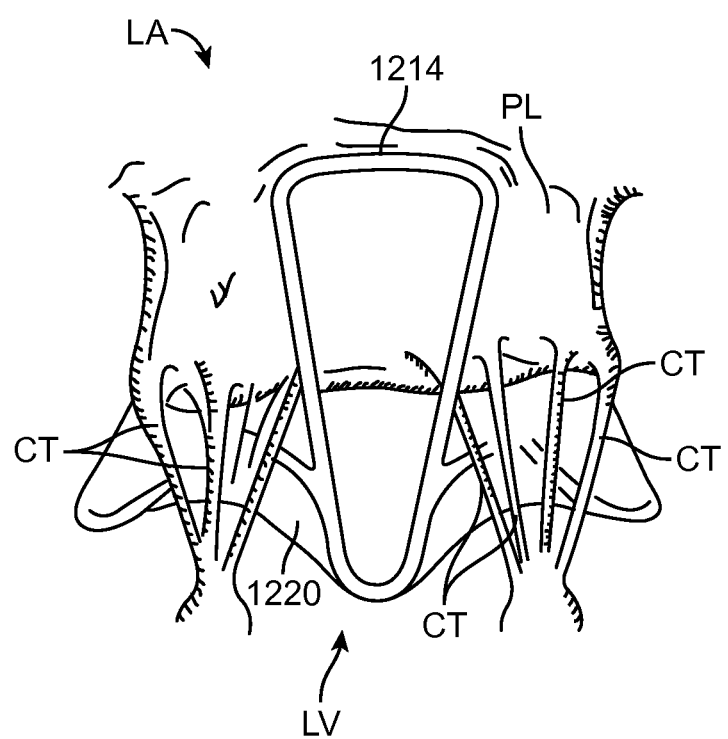

FIGS. 12K and 12L highlight engagement of the anterior and posterior tabs with the respective anterior and posterior leaflets. In FIG. 12K, after anterior tabs 1212 have been fully expanded, they capture the anterior leaflet AL and adjacent chordae tendineae between an inside surface of the anterior tab and an outer surface of the ventricular skirt 1220. Moreover, the tips 1228 of the anterior tabs 1212 are engaged with the fibrous trigones FT of the anterior side of the mitral valve. The fibrous trigones are fibrous regions of the valve thus the anterior tabs further anchor the prosthetic valve into the native mitral valve anatomy. One anterior tab anchors into the left fibrous trigone, and the other anterior tabs anchors into the right fibrous trigone. The trigones are on opposite sides of the anterior side of the leaflet. FIG. 12L illustrates engagement of the posterior tab 1214 with the posterior leaflet PL which is captured between an inner surface of the posterior tab and an outer surface of the ventricular skirt 1220. Additionally, adjacent chordae tendineae are also captured between the posterior tab and ventricular skirt.

FIGS. 13A-13L illustrate another exemplary embodiment of a delivery method. This embodiment is similar to that previously described, with the major difference being the order in which the prosthetic cardiac valve self-expands into engagement with the mitral valve. Any delivery device or any prosthetic cardiac valve disclosed herein may be used, however in preferred embodiments, the embodiment of FIG. 7 is used. Varying the order may allow better positioning of the implant, easier capturing of the valve leaflets, and better anchoring of the implant. This exemplary method also preferably uses a transapical route, although transseptal may also be used.

Figure 13A:
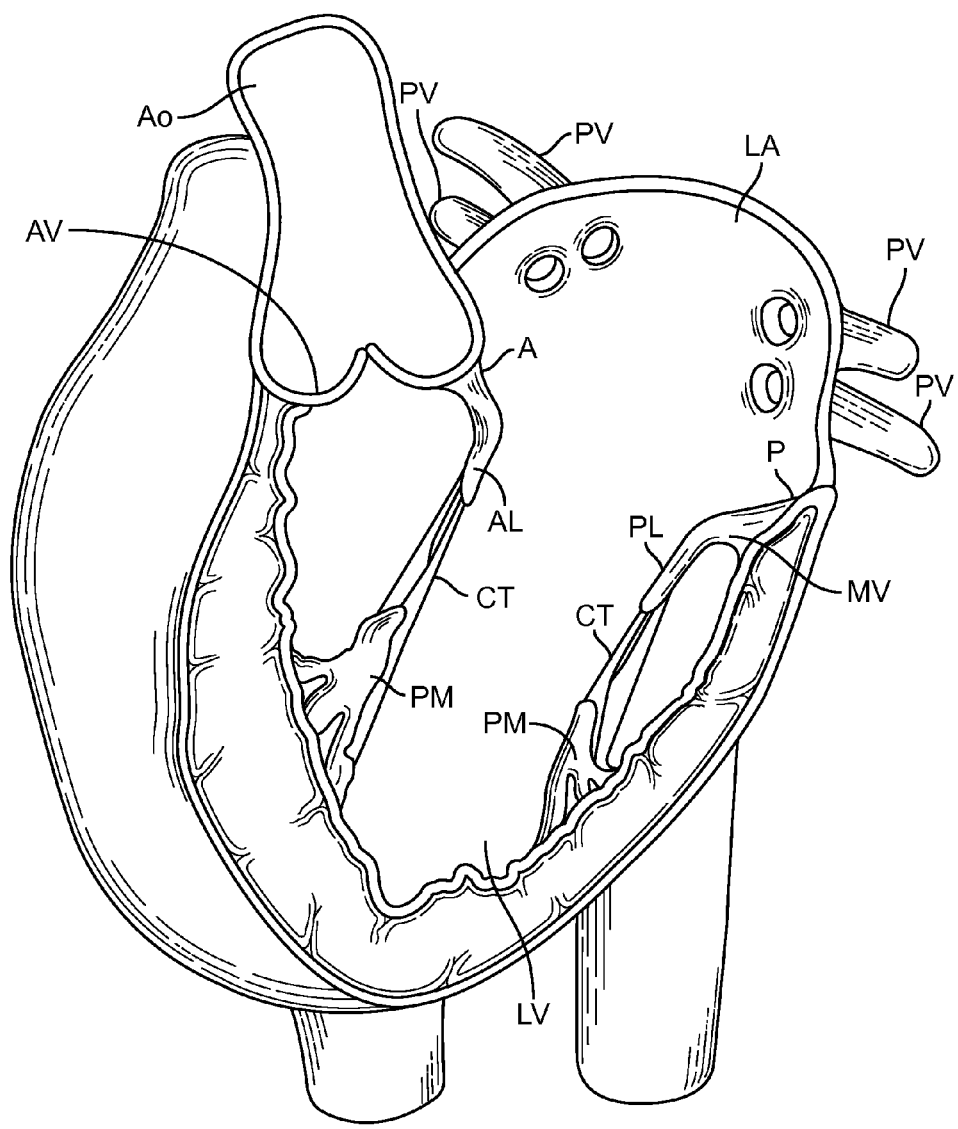
FIGS. 13A-13L illustrate another exemplary method of implanting a prosthetic cardiac valve.

FIG. 13A illustrates the basic anatomy of the left side of a patient's heart including the left atrium LA and left ventricle LV. Pulmonary veins PV return blood from the lungs to the left atrium and the blood is then pumped from the left atrium into the left ventricle across the mitral valve MV. The mitral valve includes an anterior leaflet AL on an anterior side A of the valve and a posterior leaflet PL on a posterior side P of the valve. The leaflets are attached to chordae tendineae CT which are subsequently secured to the heart walls with papillary muscles PM. The blood is then pumped out of the left ventricle into the aorta AO with the aortic valve AV preventing regurgitation.

Figure 13B:
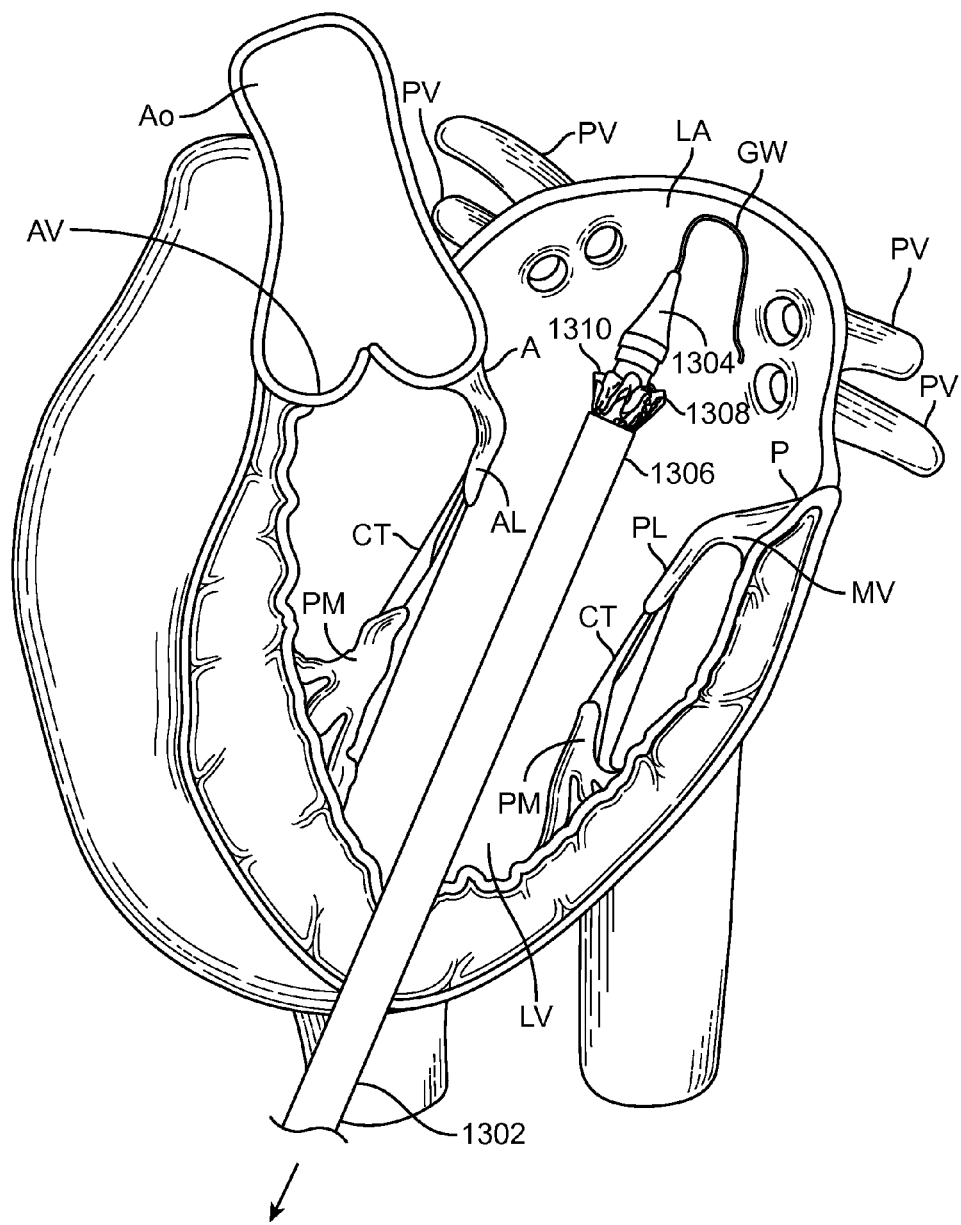
Figure 13C:
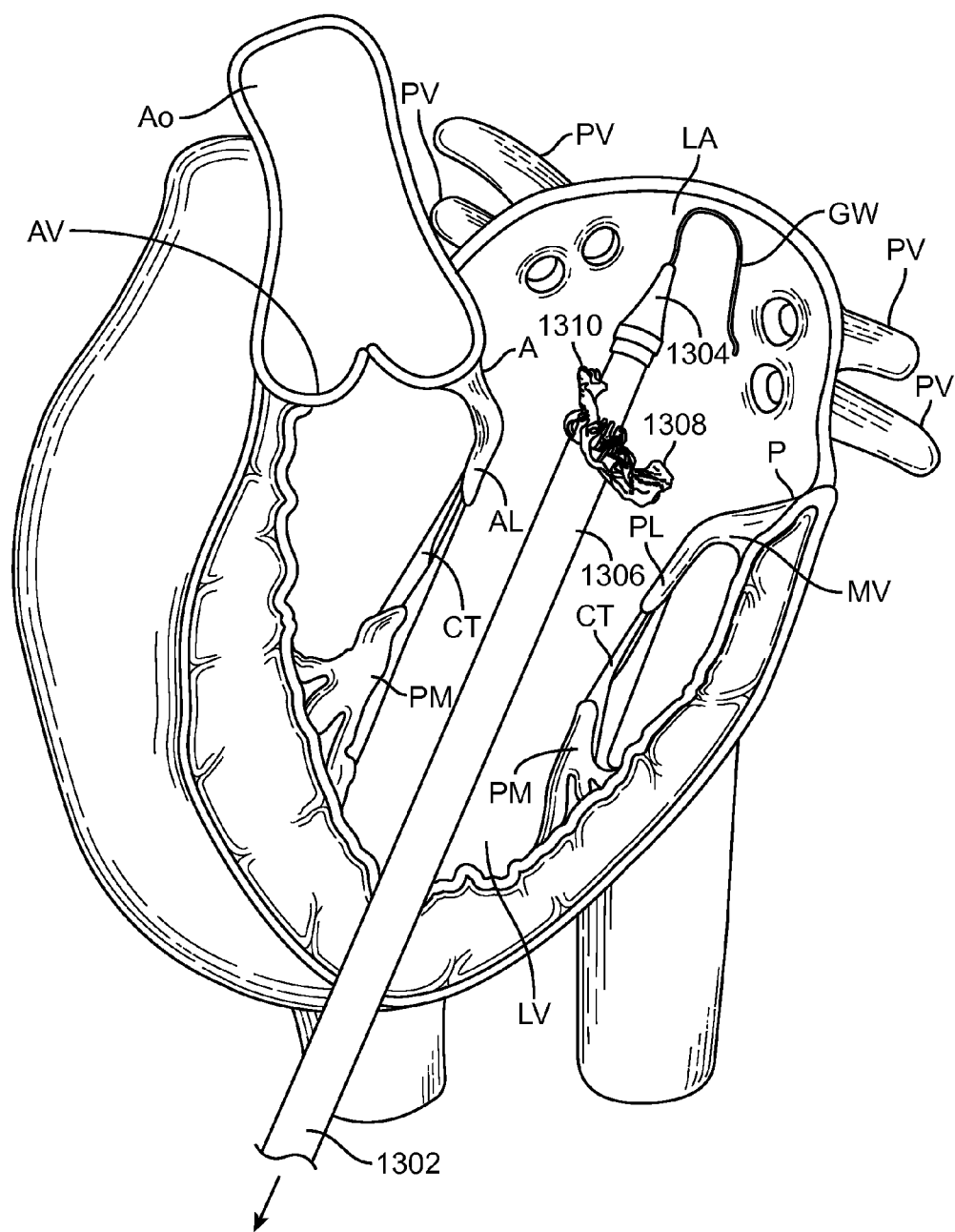
Figure 13D:
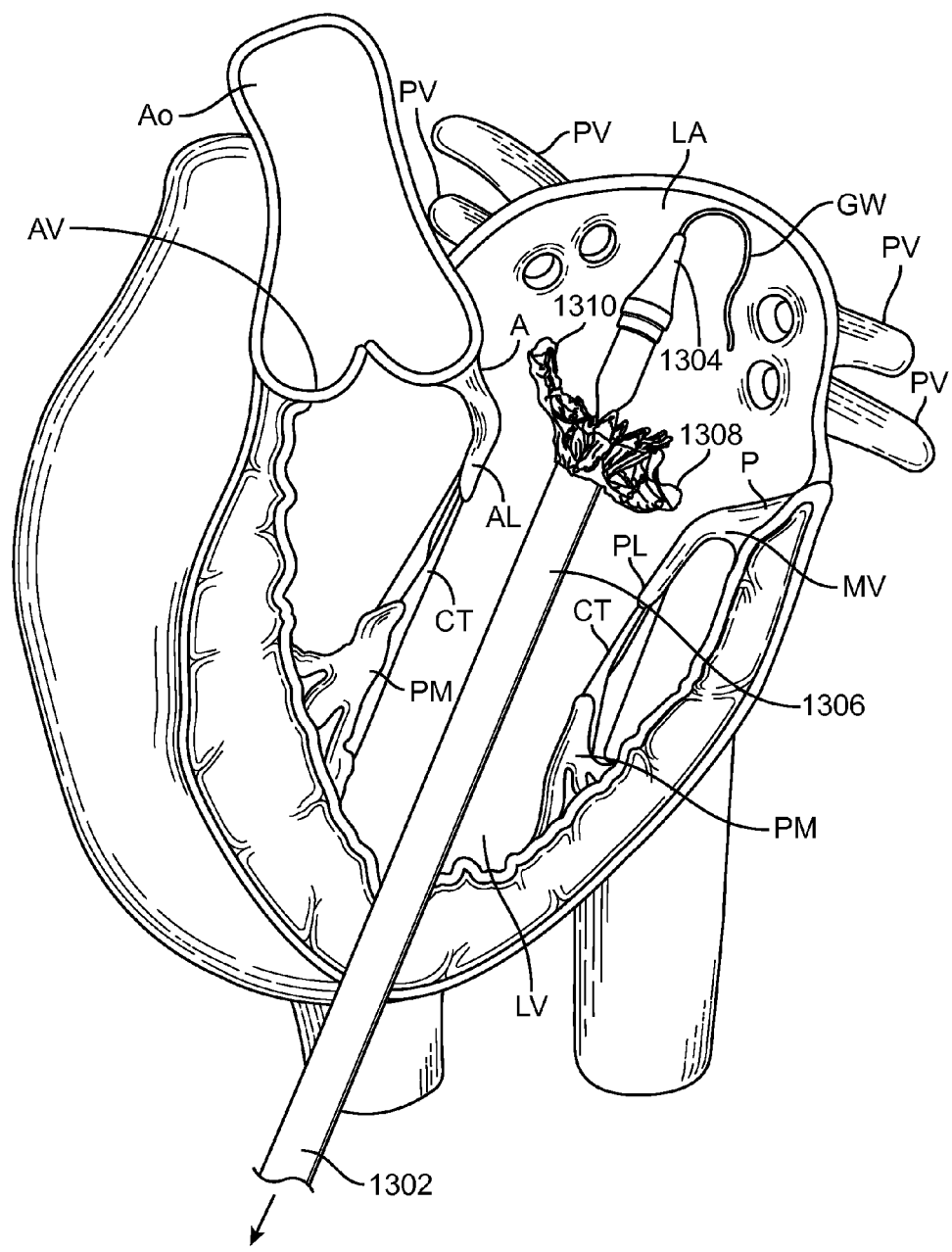

FIG. 13B illustrates transapical delivery of a delivery system 1302 through the apex of the heart into the left atrium LA via the left ventricle LV. The delivery system 1302 may be advanced over a guidewire GW into the left atrium, and a tissue penetrating tip 1304 helps the delivery system pass through the apex of the heart by dilating the tissue and forming a larger channel for the remainder of the delivery system to pass through. The delivery catheter carries prosthetic cardiac valve 1308. Once the distal portion of the delivery system has been advanced into the left atrium, the outer sheath 1306 may be retracted proximally (e.g. toward the operator) thereby removing the constraint from the atrial portion of the prosthetic valve 1308. This allows the atrial skirt 1310 to self-expand radially outward. In FIG. 13C, as the outer sheath is further retracted, the atrial skirt continues to self-expand and peek out, until it fully deploys as seen in FIG. 13D. The atrial skirt may have a cylindrical shape or it may be D-shaped as discussed above with a flat anterior portion and a cylindrical posterior portion so as to avoid interfering with the aortic valve and other aspects of the left ventricular outflow tract. The prosthesis may be oriented and properly positioned by rotating the prosthesis and visualizing the alignment element previously described. Also, the prosthetic cardiac valve may be advanced upstream or downstream to properly position the atrial skirt. In preferred embodiments, the atrial skirt forms a flange that rests against a superior surface of the mitral valve and this anchors the prosthetic valve and prevents it from unwanted movement downstream into the left ventricle.

Figure 13E:
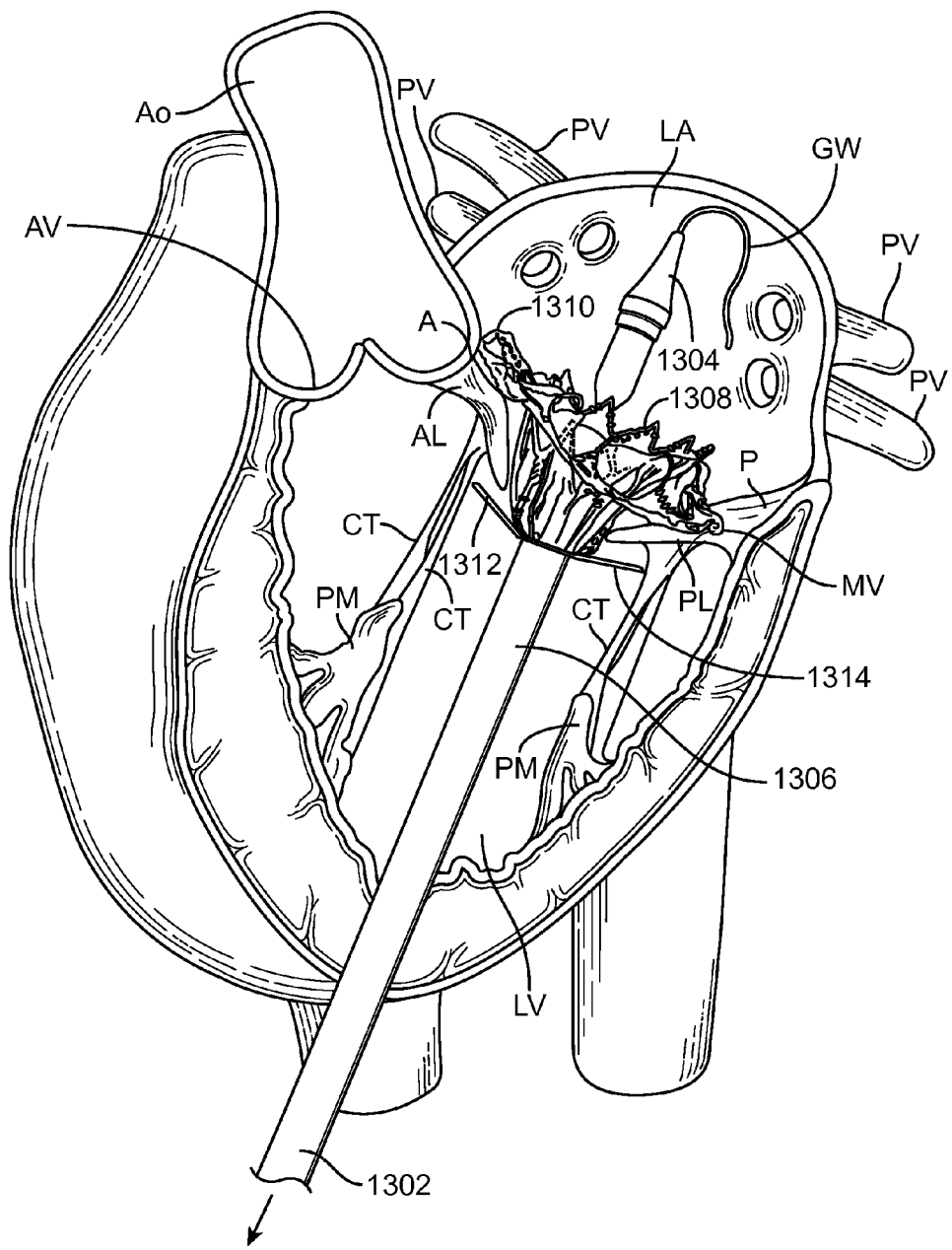
Figure 13F:
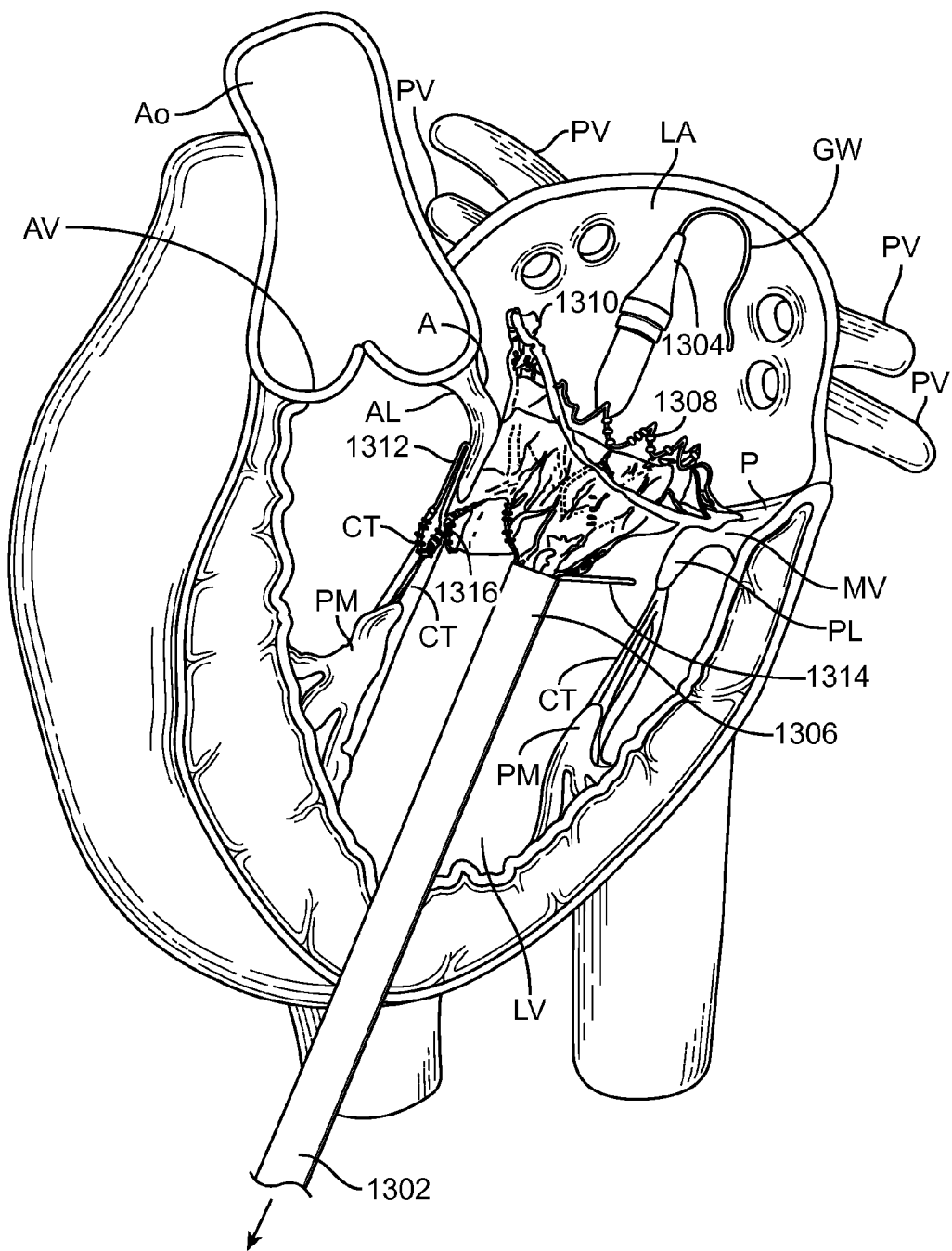

As the outer sheath 1306 continues to be proximally retracted, the annular region of the prosthetic cardiac valve self-expands next into engagement with the valve annulus. The annular region also preferably has the D-shaped geometry, although it may also be cylindrical or have other geometries to match the native anatomy. In FIG. 13E, retraction of sheath 1306 eventually allows both the anterior 1312 and posterior 1314 tabs to partially self-expand outward preferably without engaging the anterior or posterior leaflets or the chordae tendineae. In this embodiment, further retraction of the outer sheath 1306 then allows both the anterior tabs 1312 (only one visible in this view) to complete their self-expansion so that the anterior leaflet is captured between an inner surface of each of the anterior tabs and an outer surface of the ventricular skirt 1316, as illustrated in FIG. 13F. The posterior tab 1214 remains partially open, but has not completed its expansion yet. Additionally, the tips of the anterior tabs also anchor into the left and right fibrous trigones of the mitral valve, as will be illustrated in greater detail below.

Figure 13G:
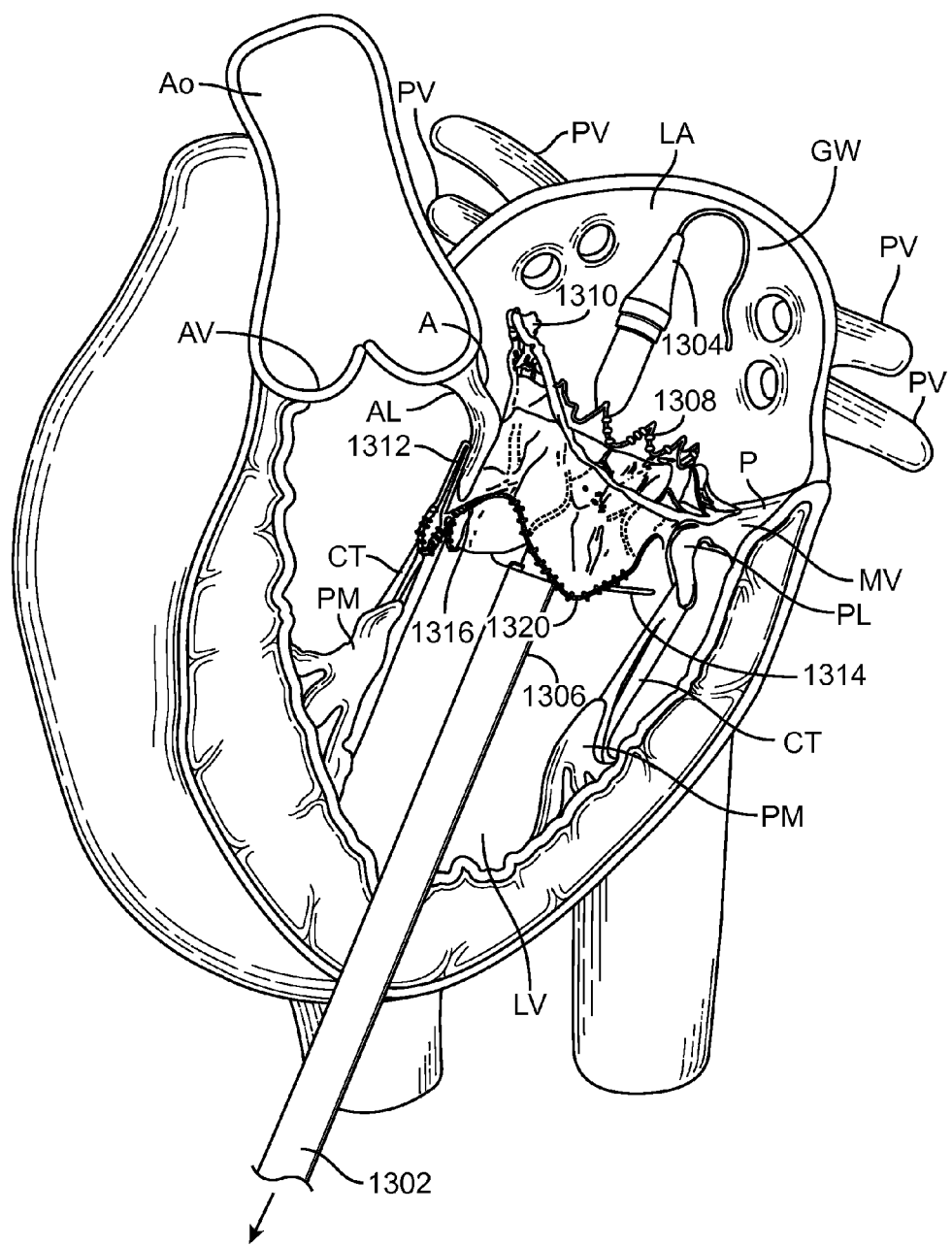
Figure 13H:
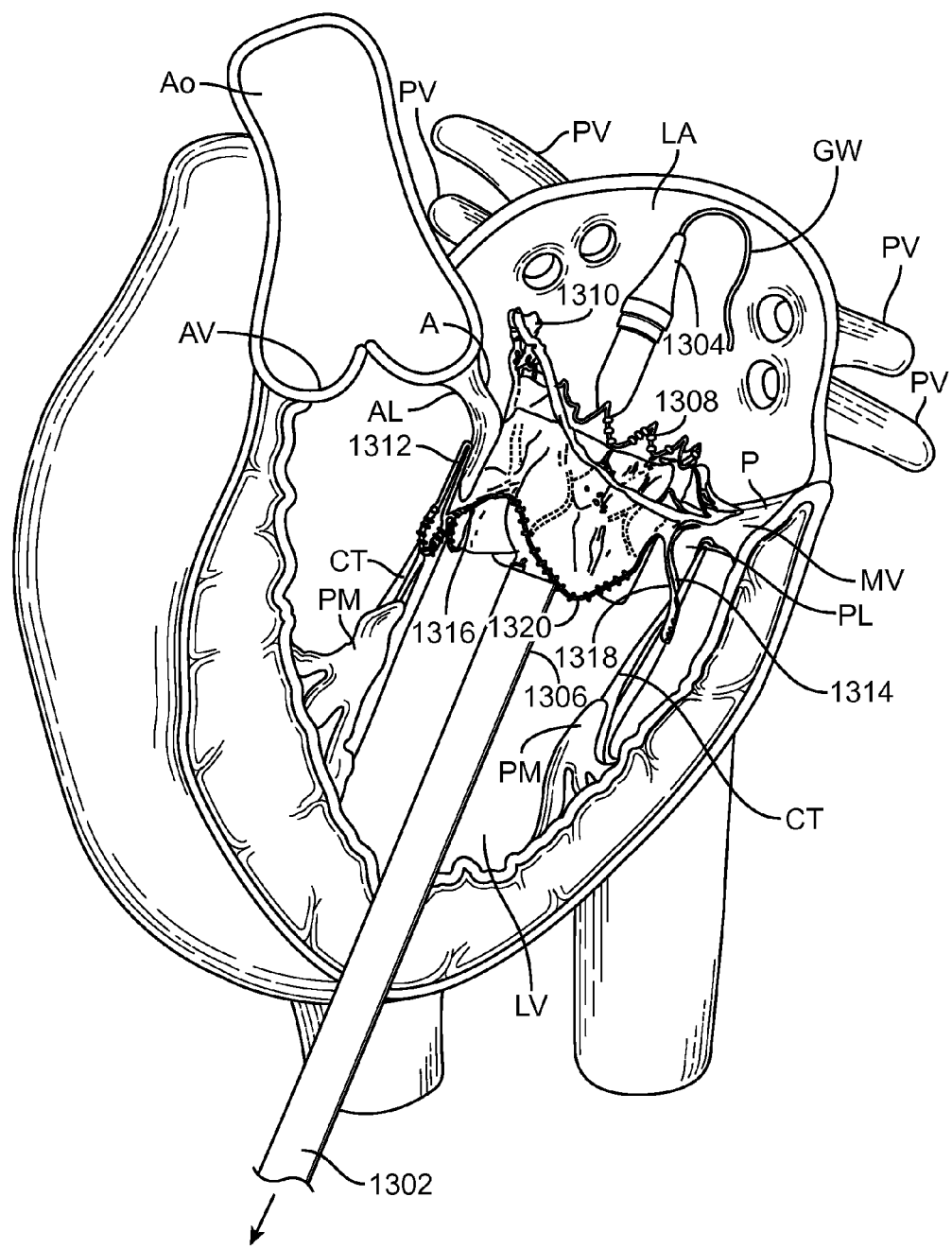

In FIG. 13G, further retraction of the outer sheath 1306 then releases the constraint from the ventricular skirt 1320 allowing the ventricular skirt to radially expand. This then further captures the anterior leaflets AL between the anterior tab 1312 and the ventricular skirt 1316. Expansion of the ventricular skirt also pushes the anterior and posterior leaflets outward, thereby ensuring that the native leaflets do not interfere with any portion of the prosthetic valve or the prosthetic valve leaflets. Further retraction of sheath 1306 as illustrated in FIG. 13H releases the constraint from the posterior tab 1314 allowing it to complete its self-expansion, thereby capturing the posterior leaflet PL between an inner surface of the posterior tab 1314 and an outer surface of the ventricular skirt 1318. The prosthetic valve is now anchored in position above the mitral valve, along the annulus, to the valve leaflets, and below the mitral valve, thereby securing it in position.

Figure 13I:
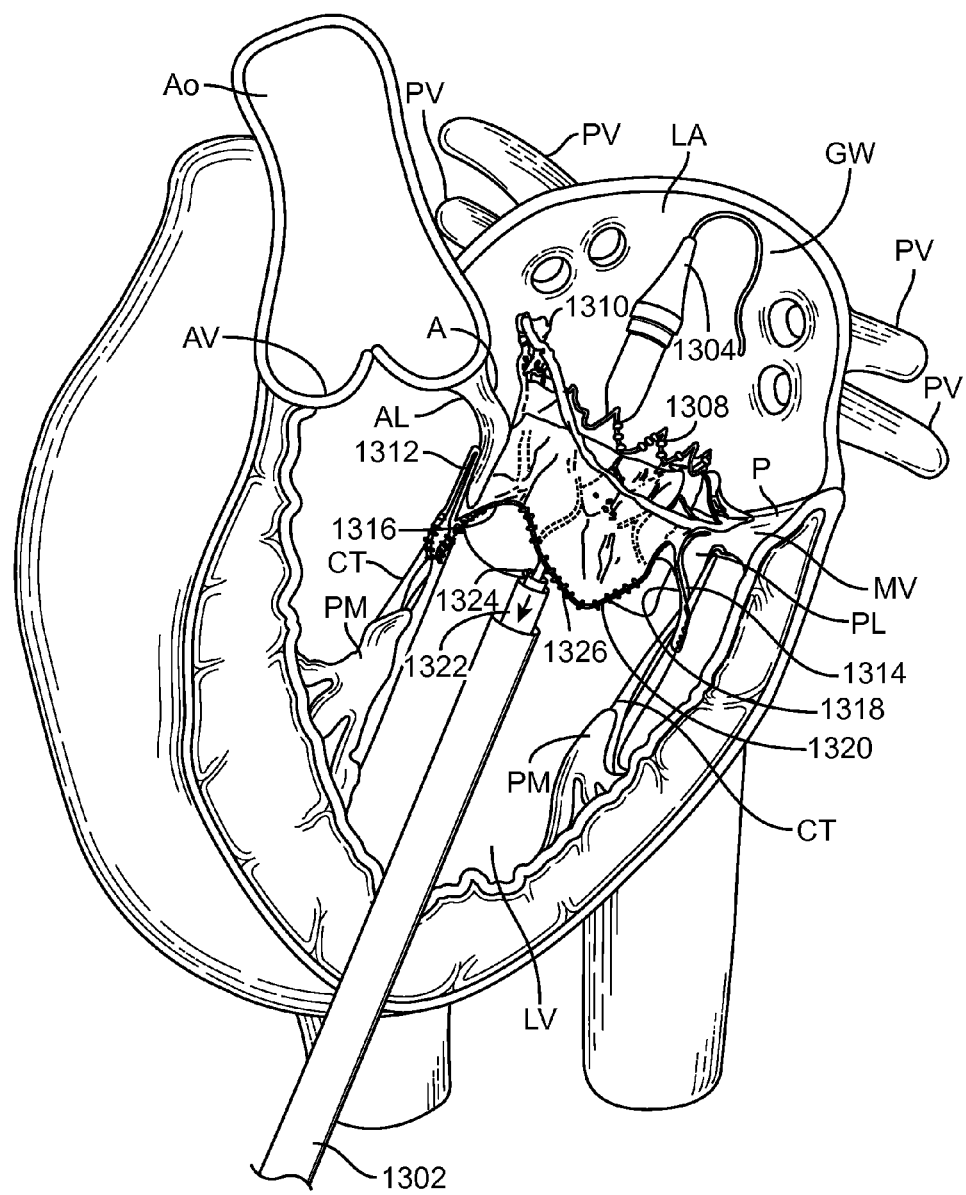
Figure 13J:
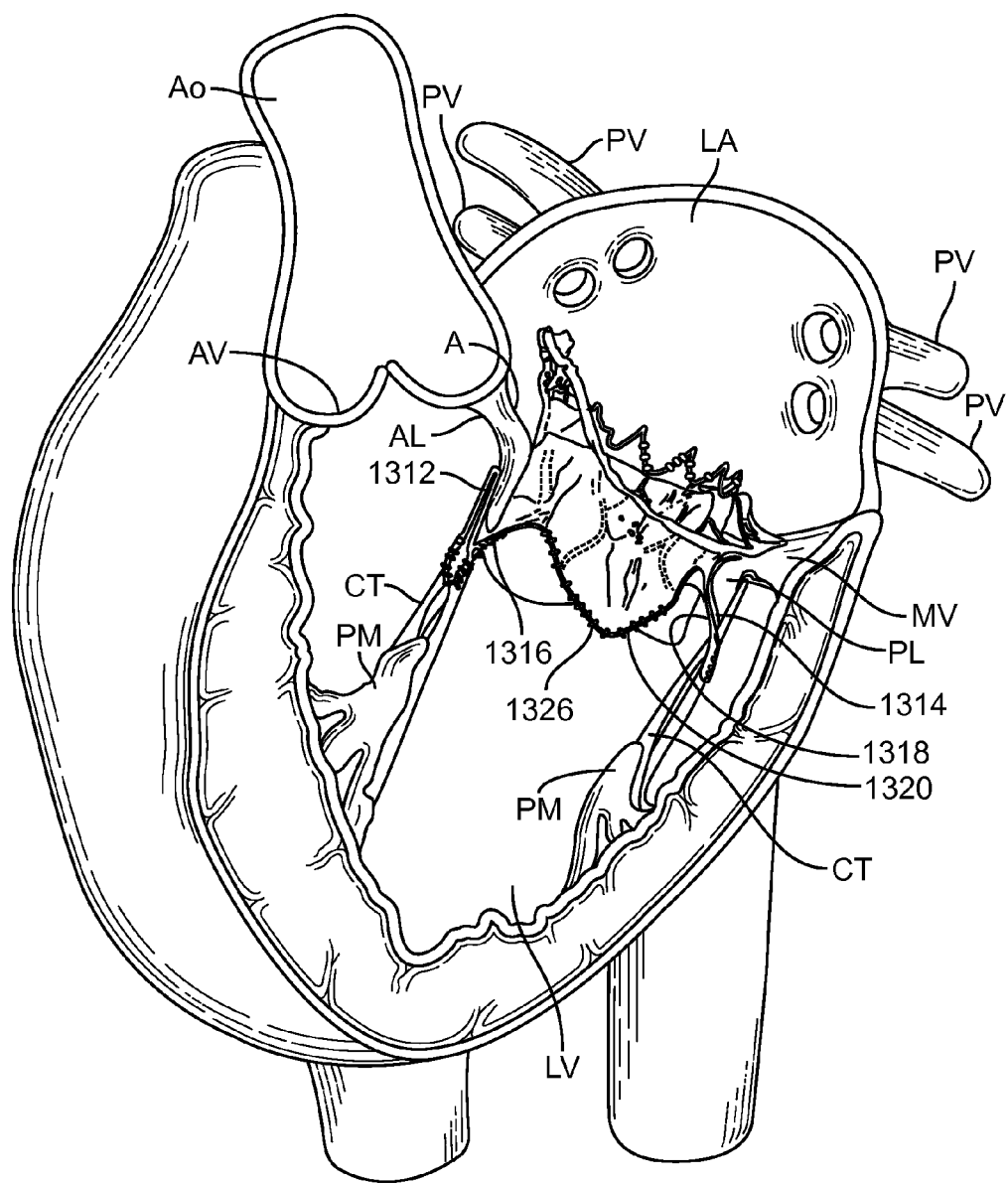

Further actuation of the delivery device now retracts the outer sheath 1306 and the bell catheter shaft 1322 so as to remove the constraint from the hub catheter 1324, as illustrated in FIG. 13I. This permits the prosthetic valve commissures 1326 to be released from the hub catheter, thus the commissures expand to their biased configuration. The delivery system 1302 and guidewire GW are then removed, leaving the prosthetic valve 1308 in position where it takes over for the native mitral valve, as seen in FIG. 13J.

Figure 13K:
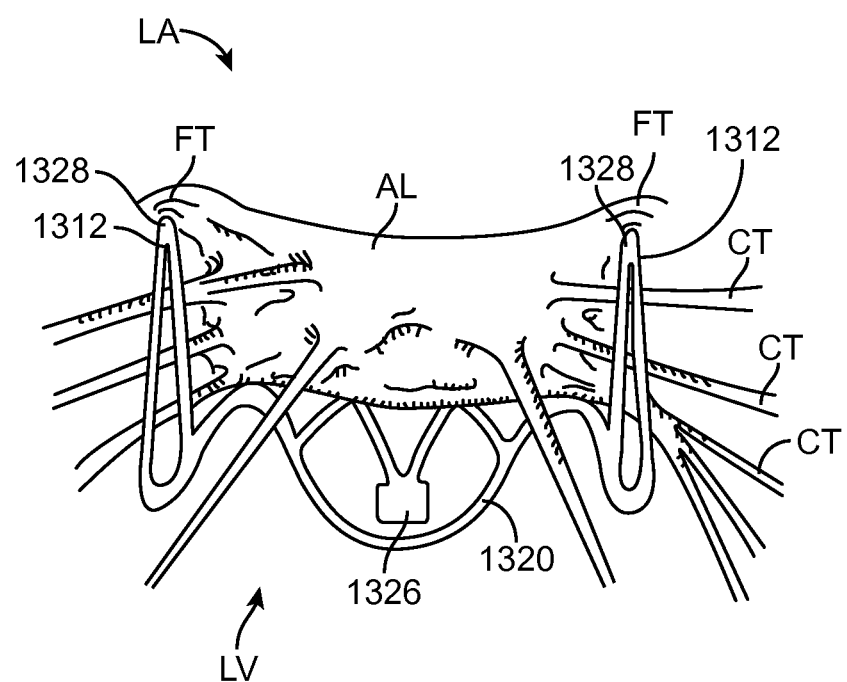
Figure 13L:
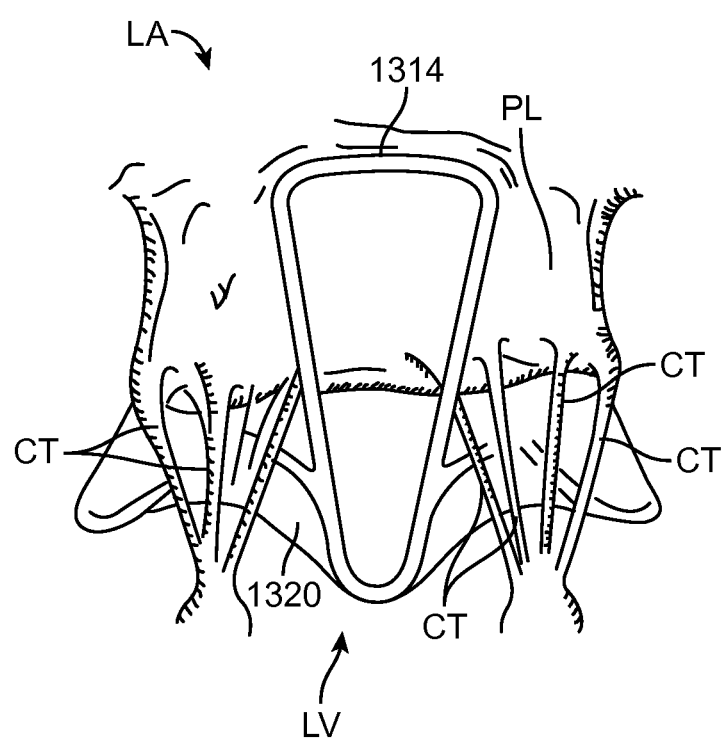

FIGS. 13K and 13L highlight engagement of the anterior and posterior tabs with the respective anterior and posterior leaflet. In FIG. 13K, after anterior tabs 1312 have been fully expanded, they capture the anterior leaflet AL and adjacent chordae tendineae between an inside surface of the anterior tab and an outer surface of the ventricular skirt 1320. Moreover, the tips 1328 of the anterior tabs 1312 are engaged with the fibrous trigones FT of the anterior side of the mitral valve. The fibrous trigones are fibrous regions of the valve thus the anterior tabs further anchor the prosthetic valve into the native mitral valve anatomy. One anterior tab anchors into the left fibrous trigone, and the other anterior tabs anchors into the right fibrous trigone. The trigones are on opposite sides of the anterior side of the leaflet. FIG. 13L illustrates engagement of the posterior tab 1314 with the posterior leaflet PL which is captured between an inner surface of the posterior tab and an outer surface of the ventricular skirt 1320. Additionally, adjacent chordae tendineae are also captured between the posterior tab and ventricular skirt.

Tab Covering. In the exemplary embodiments described above, the tabs (anterior trigonal tabs and posterior ventricular tab) are generally narrow and somewhat pointy. The embodiment previously described with respect to FIG. 8 includes a horizontal strut on the posterior tab that helps distribute force across a greater area and thereby reduces trauma to the tissue. FIGS. 14A-14D illustrate another embodiment that is preferably used with the anterior trigonal tabs to help reduce trauma. It may also be used with the posterior tab if desired.

Figure 14A:
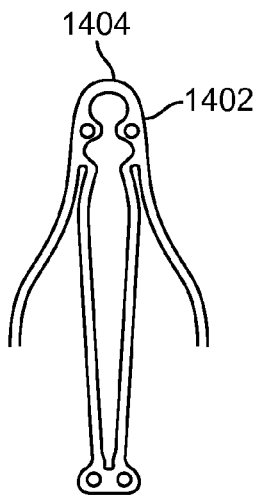
FIGS. 14A-14D illustrate an exemplary embodiment of a tab covering.
Figure 14B:
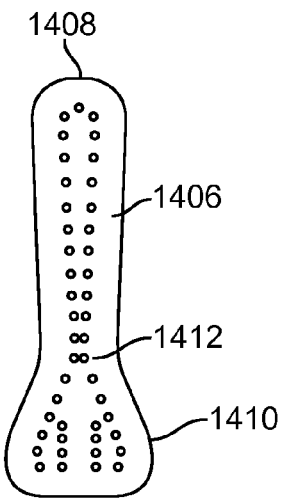
Figure 14C:
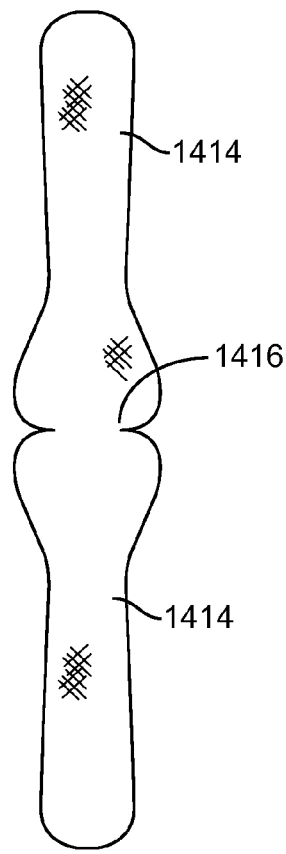
Figure 14D:
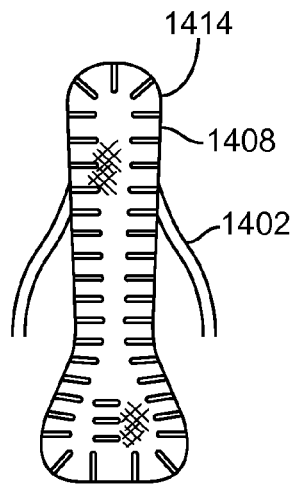

FIG. 14A illustrates an anterior trigonal tab 1402 having a tip 1404. This tip can be narrow and pointy and thereby induce tissue trauma when deployed into the tissue. Therefore, in some embodiments, it may be desirable to place a cover over the tip to help reduce tissue trauma. FIG. 14B illustrates a polymer tab 1406 that may be attached to the trigonal tab 1402. In other embodiments, the tab may be formed from other materials such as fabric, metals, or other materials known in the art. The polymer tab may be laser cut from a sheet of polymer and includes a long axial portion 1408 and an enlarged head region 1410. A plurality of suture holes 1412 may be pre-cut into the polymer tab 1406 and the holes are sized to receive suture material. Precut holes on the polymer tab may be aligned with pre-cut holes on the trigonal tab and then the polymer tab may be secured to the trigonal tab with sutures, adhesives, or other coupling techniques known in the art. A fabric cover 1414 having two symmetric halves separated by a hinged area 1416 is then wrapped around the polymer tab and attached to the polymer tab by sutures, thereby forming a shroud around the trigonal tab. The fabric may be Dacron, ePTFE, or any other biocompatible material known in the art. Thus, the cover increases the surface area of contact between the trigonal tabs and the tissue thereby reducing potential trauma and likelihood of piercing the heart wall. Additionally, the material may allow tissue ingrowth which further helps to anchor the prosthesis. Materials and dimensions are also selected in order to maintain the low profile of the device during delivery in the collapsed configuration.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A sequentially deployed prosthetic cardiac valve system, said system comprising:
    an outer sheath;
    a self-expanding frame disposed at least partially in the outer sheath, the self-expanding frame comprising a first end, a second end opposite the first end, an atrial region near the second end, and a ventricular region near the first end,
    wherein the self-expanding frame has an expanded configuration and a collapsed configuration, the expanded configuration adapted to engage heart tissue, and the collapsed configuration adapted to be delivered to a patient's heart;
    a self-expanding atrial skirt disposed in the atrial region;
    a self-expanding ventricular skirt disposed in the ventricular region, the self-expanding ventricular skirt having struts with a length;
    a self-expanding annular region disposed between the atrial region and the ventricular region;
    a first self-expanding anterior tab disposed on an anterior portion of the self-expanding frame in the ventricular region, the first self-expanding anterior tab having struts with a length shorter than the length of the struts in the ventricular skirt; and
    a self-expanding posterior tab on a posterior portion of the self-expanding frame in the ventricular region, the self-expanding posterior tab having struts with a length longer than the length of the struts in the ventricular skirt,
    wherein a portion of the first self-expanding anterior tab and a portion of the self-expanding posterior tab begin partially self-expanding concurrently and radially outward when the sheath is partially removed therefrom, and
    wherein the first anterior tab fully self-expands radially outward when the sheath is completely removed therefrom, and the first anterior tab fully self-expands before the posterior tab fully expands, and
    wherein the first anterior tab fully self-expands before the ventricular skirt fully self-expands radially outward.

2. The system of claim 1, wherein at least a portion of the atrial skirt is covered with tissue or a synthetic material.

3. The system of claim 1, wherein the atrial skirt has a collapsed configuration and an expanded configuration, the collapsed configuration adapted for delivery to the patient's heart, and the expanded configuration radially expanded relative to the collapsed configuration and adapted to lie over a superior surface of a patient's native mitral valve, thereby anchoring the atrial skirt against a portion of the left atrium.

4. The system of claim 1, wherein the atrial skirt comprises one or more radiopaque markers.

5. The system of claim 1, wherein the atrial skirt comprises a plurality of axially oriented struts connected together with a connector element, the plurality of interconnected struts forming a series of peaks and valleys.

6. The system of claim 1, wherein after self-expansion of the atrial skirt, the atrial skirt forms a flanged region adjacent the second end of the self-expanding frame.

7. The system of claim 1, wherein after self-expanding, the atrial skirt has an asymmetrically D-shaped cross-section having a substantially flat anterior portion, and a cylindrically shaped posterior portion.

8. The system of claim 1, further comprising an alignment element coupled to an anterior portion of the atrial skirt, wherein the alignment element is adapted to be aligned with an aortic root of the patient's heart and adapted to be disposed between two fibrous trigones of an anterior leaflet of a patient's mitral valve.

9. The system of claim 1, wherein at least a portion of the annular region is covered with tissue or a synthetic material.

10. The system of claim 1, wherein the annular region has a collapsed configuration and an expanded configuration, the collapsed configuration adapted for delivery to the patient's heart, and the expanded configuration radially expanded relative to the collapsed configuration and adapted to conform with and to engage an annulus of a patient's native mitral valve.

11. The system of claim 1, wherein after self-expanding, the annular region has an asymmetrically D-shaped cross-section having a substantially flat anterior portion, and a cylindrically shaped posterior portion.

12. The system of claim 1, wherein the annular region comprises a plurality of axially oriented struts connected together with a connector element, the plurality of interconnected struts forming a series of peaks and valleys.

13. The system of claim 12, wherein one or more of the plurality of axially oriented struts comprise one or more suture holes extending therethrough, the suture holes sized to receive a suture.

14. The system of claim 1, wherein at least a portion of the ventricular skirt is covered with tissue or a synthetic material.

15. The system of claim 1, wherein after self-expanding, the ventricular skirt comprises an asymmetrically D-shaped cross-section having a substantially flat anterior portion, and a cylindrically shaped posterior portion.

16. The system of claim 1, wherein the ventricular skirt has a collapsed configuration and an expanded configuration, the collapsed configuration adapted for delivery to the patient's heart, and the expanded configuration radially expanded relative to the collapsed configuration and adapted to displace native mitral valve leaflets radially outward.

17. The system of claim 1, wherein the first anterior tab has a tip portion adapted to engage a first fibrous trigone on a first side of an anterior leaflet of a patient's mitral valve, and wherein the first anterior tab is adapted to capture the anterior leaflet and adjacent chordae tendineae between the first anterior tab and an outer anterior surface of the ventricular skirt.

18. The system of claim 17, wherein the prosthetic cardiac valve further comprises a second self-expanding anterior tab disposed on the anterior portion of the self-expanding frame in the ventricular region, and wherein the second anterior tab has a tip portion adapted to engage a second fibrous trigone on a second side of the anterior leaflet of the patient's mitral valve opposite the first side of the anterior leaflet, and wherein the second anterior tab is adapted to capture the anterior leaflet and adjacent chordae tendineae between the second anterior tab and the outer anterior surface of the ventricular skirt.

19. The system of claim 18, further comprising a covering disposed over the first or the second anterior tab, the covering increasing contact surface area of the respective first or second anterior tab with the heart tissue.

20. The system of claim 19, wherein the covering comprises a fabric material disposed over a polymer tab that is coupled to the first or the second anterior tab.

21. The system of claim 1, wherein the posterior tab is adapted to being anchored over a posterior leaflet of the patient's mitral valve, such that the posterior tab is seated between the posterior leaflet and a ventricular wall of a patient's heart.

22. The system of claim 1, wherein the struts of the posterior tab comprise a plurality of struts, wherein adjacent struts are coupled together to form a plurality of expandable hinged joints, and wherein upon radial expansion of the posterior tab, the plurality of struts move away from one another thereby opening the hinged joints and forming an elongate horizontal section which allows engagement and anchoring of the posterior tab with a sub-annular region of the mitral valve between the posterior leaflet and the ventricular wall.

23. The system of claim 1, wherein the ventricular skirt further comprises a plurality of barbs coupled thereto, the plurality of barbs adapted to anchor the ventricular skirt into heart tissue.

24. The system of claim 1, wherein the struts of the ventricular skirt comprise a plurality of struts connected together with a connector element, the plurality of interconnected struts forming a series of peaks and valleys.

25. The system of claim 24, wherein one or more of the struts of the ventricular skirt comprise one or more suture holes extending therethrough, the suture holes sized to receive a suture.

26. The system of claim 1, further comprising a plurality of prosthetic valve leaflets, each of the leaflets having a first end and a free end, wherein the first end is coupled with the self-expanding frame and the free end is opposite of the first end, wherein the prosthetic valve leaflets have an open configuration in which the free ends of the prosthetic valve leaflets are disposed away from one another to allow antegrade blood flow therepast, and a closed configuration in which the free ends of the prosthetic valve leaflets engage one another and substantially prevent retrograde blood flow therepast.

27. The system of claim 26, wherein the plurality of prosthetic valve leaflets form a tricuspid valve.

28. The system of claim 26, wherein at least a portion of one or more of the prosthetic valve leaflets comprises tissue or a synthetic material.

29. The system of claim 26, wherein one or more of the prosthetic valve leaflets comprise a commissure post having a commissure tab, the commissure tab adapted to be releasably engaged with a delivery device.

30. The system of claim 1, wherein the prosthetic cardiac valve carries a therapeutic agent, the therapeutic agent is adapted to being eluted therefrom.

31. The system of claim 1, wherein the atrial skirt completely self-expands before the first anterior tab self-expands.

32. The system of claim 1, wherein the atrial skirt completely self-expands before the posterior tab self-expands.

* * * * *